(12) United States Patent
Bock et al.

(10) Patent No.: US 7,482,139 B2
(45) Date of Patent: Jan. 27, 2009

(54) VARIANTS OF ANTITHROMBIN III

(75) Inventors: Susan C. Bock, Salt Lake City, UT (US); Adrian N. Hobden, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 10/516,662

(22) PCT Filed: Jun. 2, 2003

(86) PCT No.: PCT/US03/17506

§ 371 (c)(1),
(2), (4) Date: Mar. 13, 2006

(87) PCT Pub. No.: WO03/101398

PCT Pub. Date: Dec. 11, 2003

(65) Prior Publication Data

US 2006/0259987 A1     Nov. 16, 2006

Related U.S. Application Data

(60) Provisional application No. 60/384,599, filed on May 31, 2002.

(51) Int. Cl.
*C12P 21/06* (2006.01)
*C07K 14/00* (2006.01)
*C07H 17/00* (2006.01)

(52) U.S. Cl. ............... 435/69.1; 536/23.1; 530/350; 514/2

(58) Field of Classification Search ............ 530/350; 536/23.1; 435/69.1, 325; 514/2
See application file for complete search history.

(56) References Cited

U.S. PATENT DOCUMENTS

| | | | |
|---|---|---|---|
| 5,204,253 A | 4/1993 | Sanford et al. | 435/459 |
| 5,420,252 A | 5/1995 | Kato et al. | 530/393 |
| 5,618,713 A | 4/1997 | Zettlemeissl et al. | 435/226 |
| 5,700,663 A | 12/1997 | Zettlemeissl et al. | 435/69.6 |
| 5,843,705 A | 12/1998 | DiTullio et al. | 800/7 |
| 6,878,813 B2 * | 4/2005 | Bock et al. | 530/393 |

FOREIGN PATENT DOCUMENTS

| | | |
|---|---|---|
| EP | 0 568 833 A1 | 8/1993 |
| WO | WO 90/09737 | 7/1990 |
| WO | WO 91/00291 | 1/1991 |
| WO | WO 95/05853 | 3/1995 |
| WO | WO 99/58098 | 11/1999 |

OTHER PUBLICATIONS

Theunissen et al. 1993; J. Biol. Chem. 268(12): 9035-9040.*

Backovic and Gettins, "Insight into residues critical for antithrombin function from an expanded database of sequences that includes frog, turtle and ostrich antithrombins." J. Proteome Res. 2002 1:367-373.

Bayston et al. "Familial overexpression of beta antithrombin caused by an Asn135Thr substitution." Blood 1999 93:4242-7.

Bick et al. "Antithrombin III patterns in disseminated intravascular coagulation." Am. J. Clin. Pathol. 1980 73(4):577-83.

Blauhut et al. "Substitution of antithrombin III in shock and DIC: a randomized study." Thromb. Res. 1985 39(1):81-9.

Bock et al., "Cleaved and inactivated antithrombin III in bronchoalveolar lavage (BAL) samples from acute respiratory distress (ARDS) and at-risk for ARDS patents," Proteases/Antiproteases, seminar, Amer. J. Respir. Crit. Care Med., 2001, A63. (Poster Abstract).

Bock et al. "Cloning and expression of the cDNA for human antithrombin III." Nucleic Acids Res. 1982 10(24):8113-25.

Brennan et al. "Physiological variant of antithrombin-III lacks carbohydrate sidechain at Asn 135." FEBS Lett. 1987 219(2):431-6.

Buller and Cate, "Acquired antithrombin III deficiency: laboratory diagnosis, incidence, clinical implications, and treatment with antithrombin III concentrate." Am. J. Med. 1989 87(3B):44S-48S.

Carlson et al. "Comparison of the behavior in vivo of two molecular forms of antithrombin III." Biochem. J. 1985 225:557-64.

Carrell and Owen, "Plakalbumin, alpha 1-antitrypsin, antithrombin and the mechanism of inflammatory thrombosis." Nature. 1985 317(6039):730-2.

Cohen et al. "In vivo inactivation of antithrombin III is promoted by heparin during cardiopulmonary bypass." J. Invest. Surg. 1992 5:45-9.

Cunningham et al. "Development of an elastase-resistant antithrombin through mutagenesis at P4." Blood. 1995 86(10 Supp.):375A. (Abstract).

Cunningham et al. "Impact of mutations at the P4 and P5 position on the reation of antithrombin with thrombin and elastase." Thromb. Res. 1997 88(2):171-81.

Damus and Wallace, "Immunologic measurement of antithrombin III-heparin cofactor and alpha2 macroglobulin in disseminated intravascular coagulation and hepatic failure coagulopathy." Thromb Res. 1975 6(1):27-38.

deAgostini et al. "Localization of anticoagulantly active heparan sulfate proteoglycans in vascular endothelium: Antithrombin binding on cultured endothelial cells and perfused rat aorta." J. Cell Biol. 1990 111:1293-1304.

Delsharnmar et al. "Abnormal proteolysis (DIC)—successful treatment with antithrombin III concentrate and a concentrate containing F XIII and native von Willebrand factor." J. Intern. Med. 1989 225(1):21-7.

Dickneite and Paques, "Reduction of mortality with antithrombin III in septicemic rats: a study of *Klebsiella pneumoniae* induced sepsis." Thromb Haemost. 1993 69(2):98-102.

Dunzendorfer et al. "Cell-surface heparan sulfate proteoglycanmediatedregulation of human neutrophil migration by the serpin antithrombin III." Blood 2001 97:1079-85.

(Continued)

*Primary Examiner*—Karen Cochrane Carlson
(74) *Attorney, Agent, or Firm*—Ballard Spahr Andrews & Ingersoll, LLP

(57) ABSTRACT

Disclosed are compositions and methods related to variant antithrombin III molecules.

16 Claims, 9 Drawing Sheets

OTHER PUBLICATIONS

Emerson et al. "Efficacy of antithrombin III supplemtation in animal models of fulminant *Eschericia coli* endotoxemia or bacteremia." Am. J. Med. 1989 87:27S-33S.

Emerson et al. "Protection against disseminated intravascular coagulation and death by antithrombin-III in the *Escherichia coli* endotoxemic rat." Circ Shock. 1987 21(1):1-13.

Ersdal-Badju et al. "Elimination of glycosylation heterogeneity affecting heparin affinity of recombinant human antithrombin III by expression of a beta-like variant in baculovirusinfected insect cells." Biochem. J. 1995 310:323-30.

Fourrier et al. "Double-blind, placebo-controlled trial of antithrombin III concentrates in septic shock with disseminated intravascular coagulation." Chest. 1993 104(3):882-8.

Franzen et al. "Structural studies on the carbohydrate portion of human antithrombin III." J. Biol. Chem. 1980 255(11):5090-3.

Frebelius et al. "Thrombin inhibition by antithrombin III on the subendothelium is explained by the isoform AT-beta." Thromb. Vasc. Biol. 1996 16:1292-7.

Hedin et al. "Antithrombin III inhibits thrombin-induced proliferation in human arterial smooth muscle cells." Arterioscler Thromb. 1994 14(2):254-60.

Hellgren et al. "Antithrombin III concentrate as adjuvant in DIC treatment. A pilot study in 9 severely ill patients." Thromb Res. 1984 35(4):459-66.

Hellgren et al. "Blood coagulation and fibrinolytic factors and their inhibitors in critically ill patients." Intensive Care Med. 1984 10(1):23-8.

Hoffmann et al. "Antithrombin effects on endotoxin-induced microcirculatory disorders are mediated mainly by its interaction with microvascular endothelium." Crit. Care Med. 2002 30:218-25.

Ishiguro, K. et al. "Complete antithrombin deficiency in mice results in embryonic lethality." J. Clin. Invest. 2000 106(7):873-878.

Jairajpuri et al. "Elimination of P1 arginine-393 interaction with underlying glutamic acid-255 partially activates antithrombin III for thrombin inhibition but not factor Xa inhibition." J. Biol. Chem. 2002 277:24460-5.

Jochum et al. "Effect of human granulocytic elastase on isolated human antithrombin III." Hoppe Seylers Z Physiol Chem. 1981 362(2):103-12.

Jochum, "Influence of high-dose antithrombin concentrate therapy on the release of cellular proteinases, cytokines, and soluble adhesion molecules in acute inflammation." Semin Hematol. 1995 32(4 Suppl 2):19-32.

Jordan et al. "Heparin promotes the inactivation of antithrombin by neutrophil elastase." Science. 1987 237(4816):777-9.

Jordan, "Antithrombin in vertebrate species: conservation of the heparin-dependent anticoagulant mechanism," Arch. Biochem. Biophys. 1983 227(2):587-95.

Kato et al. "Recombinant antithrombin III mutations with enhanced antithrombin activity without heparin." 69th Scientific Sessions, Abstract 4336, 1996 94:8 Supp., p. I-741. (Abstract).

Kocsis et al. "Heparin-coated stents." J. Long-Term Effects of Medical Implants. 2000 10:19-45.

Kurachi et al. "Inhibition of bovine factor IXa and factor Xabeta by antithrombin III." Biochemistry. 1976 15(2):373-7.

Lammle et al. "Plasma prekallikrein, factor XII, antithrombin III, C1(-)-inhibitor and alpha 2-macroglobulin in critically ill patients with suspected disseminated intravascular coagulation (DIC)." Am. J. Clin. Pathol. 1984 82(4):396-404.

Lawson et al. "Complex-dependent inhibition of factor VIIa by antithrombin III and heparin." J. Biol. Chem. 1993 268(2):767-70.

Mammen et al. "Human antithrombin concentrates and experimental disseminated intravascular coagulation." Semin. Thromb. Hemost. 1985 11(4):373-83.

Mant et al. "Haemorrhagic complications of heparin therapy." Lancet. 1977 1(8022):1133-5.

Marcum et al. "Microvascular heparin-like species with anticoagulant activity." Am. J. Physiol. 1983 245(5 Pt 1):H725-33.

Minnema et al. "Recombinant human antithrombin III improves survival and attenuates inflammatory responses in baboons lethally challenged with *Escherichia coli*." Blood. 2000 95(4):1117-23.

Mizuochi et al. "Structural studies of the carbohydrate moiety of human antithrombin III." Arch. Biochem. Biophys. 1980 203(1):458-65.

Nakajima et al., "Mapping the extended substrate binding site of cathepsin G and human leukocyte elastase," J. Biol. Chem. 1979 254:4027.

Nuijens et al. "Plasma elastase alpha 1-antitrypsin and lactoferrin in sepsis: evidence for neutrophils as mediators in fatal sepsis." J. Lab. Clin. Med. 1992 119(2):159-68.

O'Reilley et al. "Antiangiogenic activity of the cleaved conformation of the serpin antithrombin." Science. 1999 285(5435):1926-8.

Oelschläger et al. "Antithrombin III inhibits nuclear factor kappa B activation in human monocytes and vascular endothelial cells." Blood 2002 99:4015-20.

Olson et al. "Identification of critical molecular interactions mediating heparin activation of antithrombin. Implications for the design of improved heparin anticoagulants." Trends Cardiovasc. Med. 2002 12:198-205.

Olson et al. "Role of the antithrombin-binding pentasaccharide in heparin acceleration of antithrombin-proteinase reactions. Resolution of the antithrombin conformational change contribution to heparin rate enhancement." J. Biol. Chem. 1992 267(18):12528-38.

Ostrovsky et al. "Antithrombin III prevents and rapidly reverses leukocyte recruitment in ischemia/reperfusion." Circulation. 1997 96(7):2302-10.

Owen et al. "P1 variant antithrombins Glasgow (393 Arg to His) and Pescara (393 Arg to Pro) have increased heparin affinity and are resistant to catalytic cleavage by elastase. Implications for the heparin activation mechanism." FEBS Lett. 1991 280(2):216-20.

Petersen et al., Primary structure of antithrombin III (heparin cofactor)—partial homology between α1-antitrypsin and antithrombin-III. The Physiological Inhibitors of Coagulation and Fibrinolysis, Elsevier/North Holland Biomedical Press. 1979 pp. 43-54.

Peterson and Blackburn, "Isolation and characterization of an antithrombin III variant with reduced carbohydrate content and enhanced heparin binding." J. Biol. Chem. 1985 260(1):610-5.

Picard and Bock, "Rapid and efficient one-tube PCR-based mutagenesis method." Methods in Mol. Biol. vol. 67, PCR Cloning Protocols. From moluclar cloning to genetic engineering. B.A. White Humana Press, Totowa, NJ, 1996, 183-8.

Picard et al. "A rapid and efficient one-tube PCR-based mutagenesis technique using Pfu DNA polymerase." Nucleic Acid Res. 1994 22(13):2587-91.

Picard et al. "Partial glycosylation of antithrombin III asparagine-135 is caused by the serine in the third position of its N-glycosylation consensus sequence and is responsible for production of the beta-antithrombin III isoform with enhanced heparin affinity." Biochemistry. 1995 34(26):8433-40.

Rao et al. "Binding of factor VIIa to tissue factor permits rapid antithrombin III/heparin inhibition of factor VIIa." Blood. 1993 81(10):2600-7.

Rosenberg and Damus, "The purification and mechanism of action of human antithrombin-heparin cofactor." J. Biol. Chem. 1973 248(18):6490-505.

Rosenberg, "Chemistry of the hemostatic mechanism and its relationship to the action of heparin." Fed. Proc. 1977 36(1):10-8.

Rothenburger et al. "Treatment of thrombus formation associated with theMicroMed DeBakey VAD using recombinant tissue plasminogen activator." Circulation 2002 106(suppl I): I-189-92.

Ruf and Mueller, "Tissue factor in cancer angiogenesis and metastasis." Curr. Opin. Hematol. 1996 3(5):379-84.

Seitz et al. "Participation and interactions of neutrophil elastase in haemostatic disorders of patients with severe infections." Eur. J. Haematol. 1987 38(3):231-40.

Stephens et al. "Site directed mutagenesis of the reactive center (serine 394) of antithrombin III." J. Biol. Chem. 1988 263(31):15849-52.

Tani et al. "Thrombin enhances lung fibroblast proliferation in bleomycin-induced pulmonary fibrosis." Am. J. Respir. Cell Mol. Biol. 1991 5(1):34-40.

Tejada, M.L. and Deeley, R.G. "Cloning of an avian antithrombin: developmental and hormonal regulation of expression." Thromb. Haemost. 1995 73(4):654-661.

Turk et al. "The oligosaccharide side chain on Asn-135 of alpha-antithrombin, absent in beta-antithrombin, decreases the heparin affinity of the inhibitor by affecting the heparin-induced conformational change." Biochemistry. 1997 36(22):6682-91.

Uchiba et al. "Antithrombin III (AT III) prevents LPS-induced pulmonary vascular injury: novel biological activity of AT III." Semin. Thromb. Hemost. 1997 23(6):583-90.

van Boven and Lane, "Antithrombin and its inherited deficiency states." Semin. Hematol. 1997 34(3):188-204.

Varga et al. "Infectious entry pathway of adenovirus type 2." J. Virol. 1991 65(11):6061-70.

Vinazzer, "Antithrombin III in shock and disseminated intravascular coagulation." Clin. Appl. Thrombosis/Hemostasis. 1995 1:62-5.

Warren et al. "High-dose antithrombin III in severe sepsis: a randomized controlled trial." JAMA. 2001 286(15):1869-78.

Witmer and Hatton, "Antithrombin III-beta associates more readily than antithrombin III-alpha with uninjured and de-endothelialized aortic wall in vitro and in vivo." Arteriosclerosis and Thrombosis. 1991 11:530-9.

Wolff et al. "Direct gene transfer into mouse muscle in vivo." Science. 1990 247(4949 Pt 1):1465-8.

Zendehrouh, Ph.D. Dissertation, "Novel proteinase inhibitors for use in treatment of sepsis." Temple Univ. School of Medicine, publically available at the University of Michigan dissertation archive in 1999.

* cited by examiner

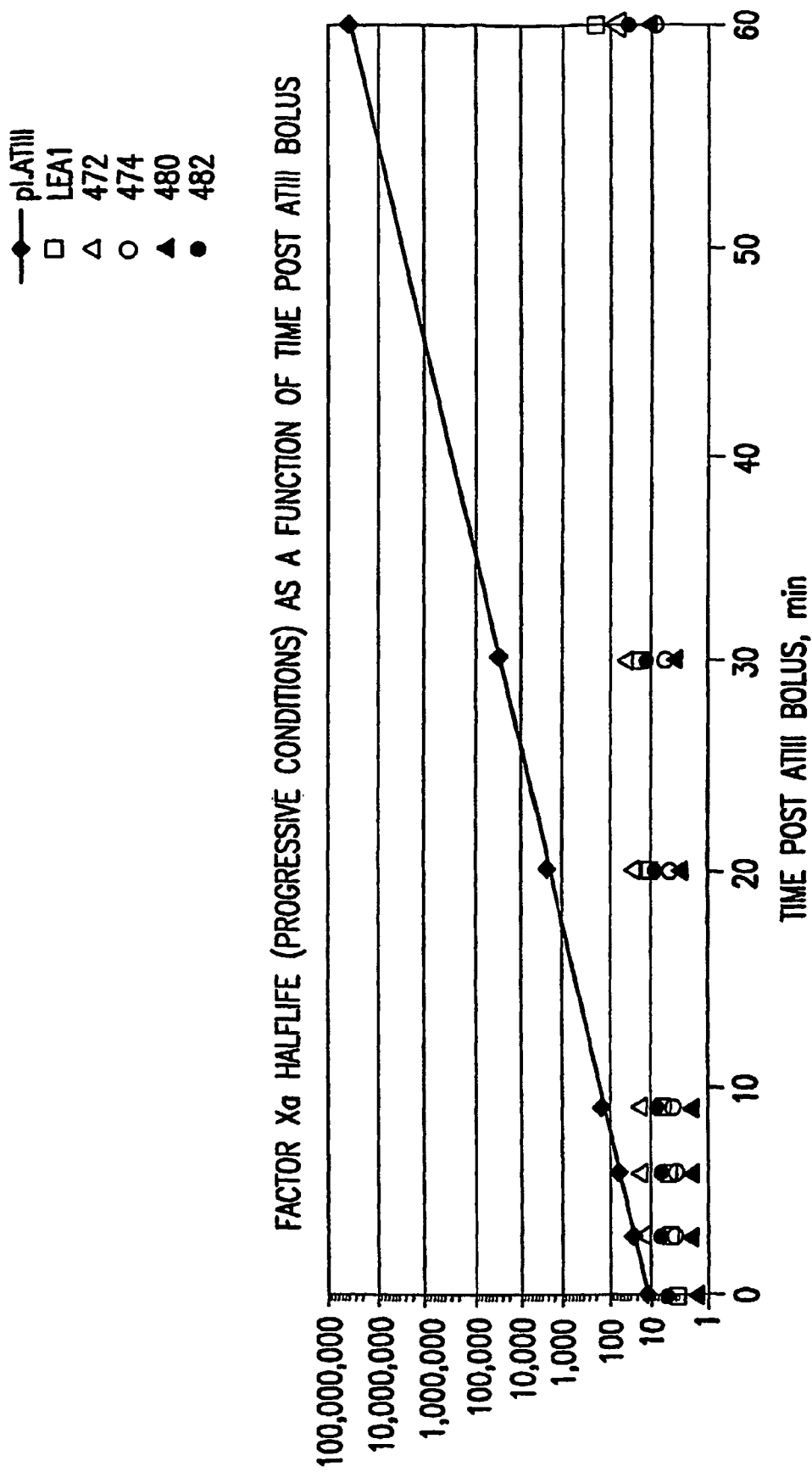

VARIANTS OF ANTITHROMBIN III

I. CROSS REFERENCE TO RELATED APPLICATIONS

This application claims priority to U.S. Provisional Application No. 60/384,599, filed May 31, 2002, for "Variants of Anti-Thrombin III," which is hereby incorporated herein by reference in its entirety.

II. BACKGROUND OF THE INVENTION

ATIII is a major inhibitor of enzymes in the coagulation cascade, including thrombin (Rosenberg and Damus, (1973) *J. Biol. Chem.*, 248, 6490-6505) and factor Xa (fXa) (Kurachi et al., (1976) *Biochemistry*, 15, 373-377). Many hereditary mutations in ATIII have been identified that promote hypercoagulability because of unchecked activity of the coagulation enzymes (Reviewed in van Boven and Lane, (1997) *Semin. Hematol.*, 34, 188-204). Acquired deficiencies of ATIII can also occur with negative repercussions on hemostasis, as for example during septic disseminated intravascular coagulopathy (DIC) (Bick et al., (1980) *Am. J. Clin. Path.*, 73, 577-583); (Buller and Cate, (1989) *Am. J. Med.*, 87, 44S-48S); (Damus and Wallace, (1989) *Thromb. Res.*, 6, 27); (Hellgren et al., (1984) *Intensive Care Med.*, 10, 23-28); (Lammle et al., (1984) *Am J Clin Patlhol*, 82, 396-404); (Mammen et al., (1985) *Semin. Thromb. Hemost.*, 11, 373-383). In contrast, hemorrhage resulting from excess inhibition of blood coagulation by ATIII can occur in the presence of pharmaceutical heparin, which is frequently used to treat and prevent hypercoagulable states (Mant et al., (1977) *Lancet*, 1, 1133-1135).

ATIII is regulated in part by elastases and proteases that cleave ATIII (Jochum et al., (1981) *Hoppe-Seyler's Z. Physiol. Chem.* 362, 103-112; Carrell and Owen, (1985) *Nature*, 317, 730-732; Jordan et al., (1987) *Science*, 237, 777-779; Mast et al., (1991) *J. Biol. Chem.* 266, 15810-15816), preventing ATIII from inhibiting thrombin, factor Xa, and other activated coagulation factor targets.

III. SUMMARY OF THE INVENTION

In accordance with the purposes of this invention, as embodied and broadly described herein, this invention, in one aspect, relates to variants of antithrombin III.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

IV. BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 shows the enzymatic halflife of thrombin in the vicinity of an inflammatory locus as a function of the time post bolus infusion of plasma ATIII or the model NR-ATIIIs. The thrombin enzymatic halflife is plotted on a log scale. Similar plots can be generated for progressive and heparin cofactor dependent inhibition of other ATIII target enzymes (including the important common pathway target, factor Xa) by plasma-derived ATIII and model NR-ATIIIs.

FIG. 5A and FIG. 5B show the fXa halflife under progressive conditions as a function of time post ATIII bolus.

V. DETAILED DESCRIPTION

Figure 1:
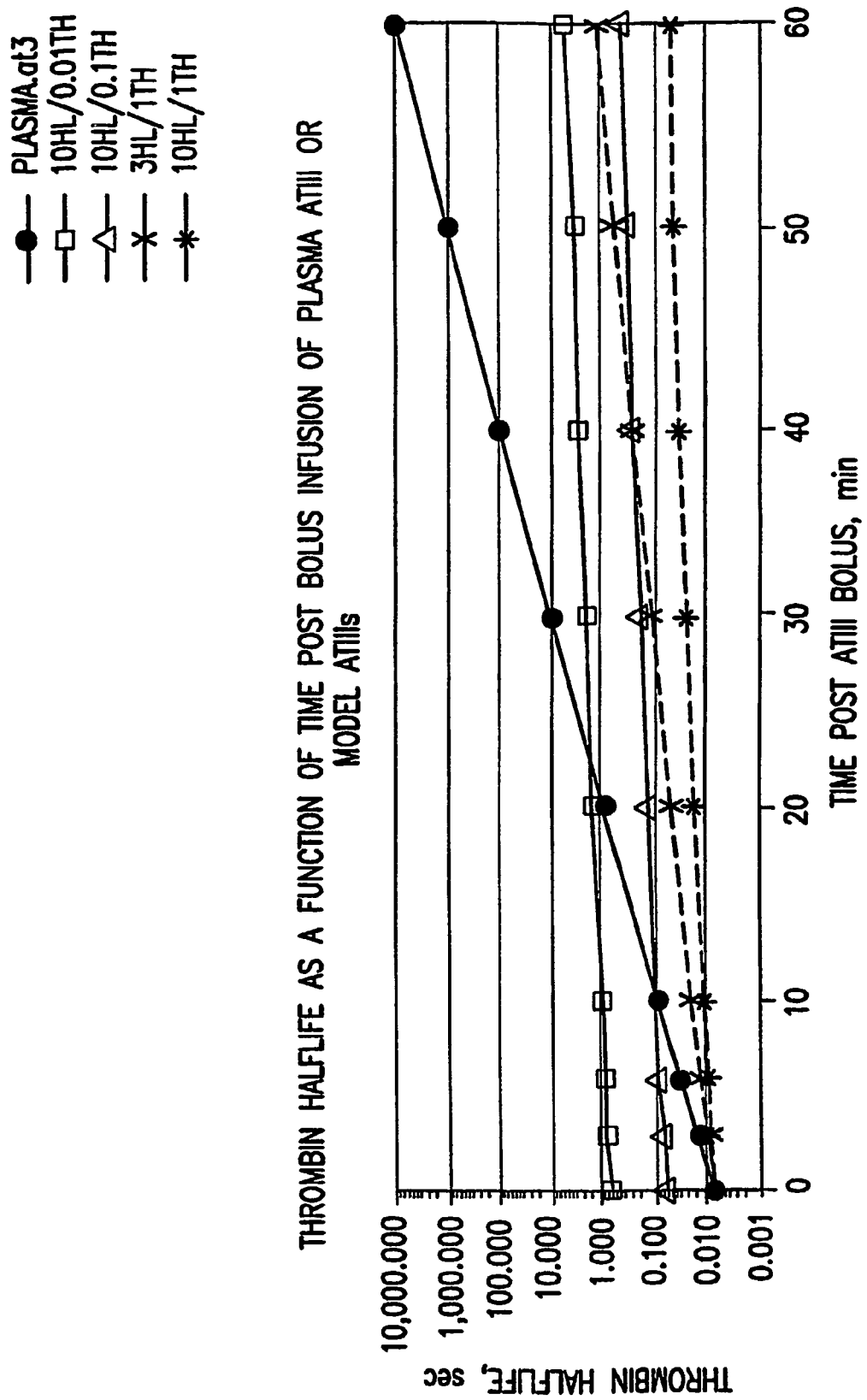

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

B. Compositions and Methods

Disclosed are compositions and methods related to variants of antithrombin III (ATIII). The disclosed compositions can have a variety of properties and characteristics that are desirable. ATIII is a glycoprotein that is widely recognized for its role in regulation of the blood coagulation cascade. For example, ATIII is responsible for inhibiting thrombin (Rosenberg and Damus, (1973) *J. Biol. Chem.*, 248, 6490-6505) and factor Xa (Kurachi et al., (1976) *Biochemistry*, 15, 373-377), which causes coagulation to be attenuated or shut down. In addition to its ability to regulate coagulation enzyme activity, ATE is known to have a variety of other activities including, anti-inflammatory properties (Minnema et al., (2000) *Blood*, 95, 1117-1123), anti-proliferative properties (Tani et al., (1991) *Am. J. Respir. Cell Mol. Biol.*, 5, 34-40) and anti-angiogenic properties (O'Reilley et al., (1999), *Science*, 285, 1926-1928). There are numerous regulatory mechanisms for ATIII activity. For example, ATIII is inactivated by elastases, and IgG activated neutrophils (Jochum et al., (1981). *Hoppe-Seyler's Z. Physiol. Chem.*, 362, 103-112). This destroys ATIII proteinase inhibitor activity and prevents it from down regulating thrombin and factor Xa so that blood coagulation occurs. Some inherited mutations of ATIII promote hypercoagulability because of loss of regulation of the coagulation enzymes (see van Boven and Lane, Semin. Hematol., 34:1880294 (1997)). Disclosed are variants that have increased resistance to inactivation by neutrophil elastase, without eliminating antithrombin and/or anti factor Xa activity. Also disclosed are variants that retain observable levels of progressive and/or heparin-dependent anti-Xa activity but do not have observable levels of antithrombin activity. Also disclosed are variants that have enhanced levels of progressive and/or heparin-dependent anti-factor Xa activity compared to plasma-derived ATIII, but only similar or decreased levels of anti-thrombin activity. Also disclosed are variants that have enhanced levels of progressive and/or heparin-dependent anti-thrombin activity compared to plasma-derived ATIII, but only similar or decreased levels of anti-factor Xa activity.

C. Compositions

Disclosed are the components to be used to prepare the disclosed compositions as well as the compositions themselves and to be used within the methods disclosed herein. These and other materials are disclosed herein, and it is understood that when combinations, subsets, interactions, groups, etc. of these materials are disclosed that while specific reference to each various individual and collective combinations and permutation of these compounds may not be explicitly disclosed, each is specifically contemplated and described herein. For example, if a particular variant of ATIII is disclosed and discussed and a number of modifications that can be made to a number of molecules including the variant are discussed, specifically contemplated is each and every combination and permutation of the variant of ATIII and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. ATIII

ATIII is a 432 amino acid Mr 58000 plasma glycoprotein (Bock et al., (1982) *Nucleic Acids Res.*, 10, 8113-8125); (Petersen et al., (1979) *The Physiological Inhibitors of Coagulation and Fibrinolysis* (pp. 43-54): Elsevier/North Holland Biomedical Press) which not only inhibits thrombin and factor Xa, but also the serine proteinases preceding them in the intrinsic pathway (e.g., factor IXa, factor XIa, factor XIIa) (Rosenberg, (1977) *Fed. Proc.*, 36, 10-18) and the extrinsic pathway (factor VIIa-TF) (Lawson et al., (1993) *J. Biol. Chem.*, 268: 767-770); (Rao et al., (1993) Blood, 81: 2600-2607) of blood coagulation. Factor VIIa-TF has roles not only in coagulation and thrombosis, but is implicated in cancer angiogenesis and metastasis as well (Ruf and Mueller, (1996) *Curr. Opin. Hematol.*, 3: 379-84). ATIII also effects non-coagulant, thrombin-mediated pathways, such as thrombin-induced smooth muscle cell proliferation (Hedin et al., (1994) *Arterioscler. Thromb.*, 14: 254-260) and thrombin-mediated neutrophil extravasation (Ostrovsky et al., (1997) *Circulation*, 96: 2302-2310). Moreover, ATIII promotes endothelial release of prostacyclin (PG12), which inhibits leukocyte and platelet activation, and has vasodialator properties (Uchiba et al., (1997) *Seminars in Thrombosis and Hemostasis*, 23: 583-590).

Antithrombin is synthesized in the liver and secreted in the blood as two different isoforms (Peterson and Blackburn, (1985) *J. Biol. Chem.*, 260, 610-615). The predominant species (90%), alpha-ATIII, has four identical N-glycosidic-linked polysaccharide chains attached to asparagine residues 96, 135, 155, and 192 (Franzen et al., (1980) *J. Biol. Chem.*, 255, 5090-5093); (Mizuochi et al., (1980) *Arch. Biochem. Biophys.*, 203, 458-465). The minor beta-ATIII isoform (101%) lacks the oligosaccharide side chain on asparagine 135 (Brennan et al., (1987) *FEBS Lett.*, 219, 431-436). The beta-glycoform lacks a carbohydrate on Asn-135 because of inefficient glycosylation of its NXS consensus sequence (Picard et al., (1995) *Biochemistry*, 34, 8433-8440 and.

Beta-like antithrombines can be generated not only using mutations in the first position of the NXS sequence (U.S. Pat. Nos. 5,618,713 and 5,700,663), but also by introducing mutations at the third position. The mutations in the third position of the NXS/T consensus sequence are as effective as mutations made at the first position with respect to blocking glycosylation and increasing heparin affinity (Picard et al., (1995) *Biochemistry*, 34, 8433-8440) generating beta-like ATIIIs. For example, disclosed are ATIIIs which have the third position of the NXS/T sequence varied as well as mutations which, for example, retain anti-thrombin activity or anti-factor Xa activity while increasing reistance to elastase degradation.

The inhibitory activity of ATIII towards its target enzymes is enhanced by heparin (Rosenberg and Damus, (1973) *J. Biol. Chem.*, 248, 6490-6505) and vascular surface heparan sulfate proteoglycans (HSPGs) (Marcum et al., (1983) *Am. J. Physiol.*, 245: H725-733). The heparin binding property of antithrombin directs ATIII to sites where its target enzymes are generated, and potentiates its activity on these surfaces. Thus heparin upregulates the inhibitory activity of ATIII, and also spatially regulates it so that highest rates of thrombin factor Xa inhibition are achieved on heparan sulfate proteoglycan (HSPG)—containing vascular surfaces.

ATIII is negatively regulated in part by elastases and proteases that cleave ATIII, preventing ATIII from inhibiting thrombin and factor Xa. Human neutrophil elastase cleaves and inactivates ATIII (Jochum et al., (1981). *Hoppe-Seyler's Z. Physiol. Chem.*, 362, 103-112). The reported neutrophil elastase cleavage sites were after the P5-Val and P4-Ile (Carrell and Owen, (1985) *Nature*, 317, 730-732). Furthermore, Jordan and colleagues showed that elastase inactivation of ATIII was heparin dependent (Jordan et al., (1987) *Science*, 237, 777-779). It has been hypothesized that elevated elastase (Nuijens et al., (1992) *J. Lab. Clin. Med.*, 119, 159-168) is responsible for the inactivation of ATIII in sepsis (Seitz et al. (1987) *Eur. J. Haematol.*, 38, 231-240) and reduced antithrombin levels in septic disseminated intravascular coagulatno (DIC) (Bick et al., (1980) *Am. J. Clin. Path.*, 73, 577-583); (Buller and ten Cate, (1989) *Am. J. Med.*, 87, 44S-48S); (Damus and Wallace, (1989) *Thromb. Res.*, 6, 27); (Hellgren et al., (1984a) *Intensive Care Med.*, 10, 23-28); (Lammle et al., (1984) *Am J Clin Pathol*, 82, 396-404); (Mammen et al., (1985) *Semin. Thromb. Hemost.*, 11, 373-383). This acquired decrease in functional ATIII would contribute to the progression of DIC due to the inability to inhibit activated coagulation proteinases, ultimately leading to thrombin activation, fibrin formation and coagulation factor consumption. In addition, decreased regulation of thrombin may lead to increased expression of thrombin non-coagulant functions.

Several animal and human studies have suggested that ATIII concentrate therapy may be effective in reducing mortality rates of patients suffering from DIC. Using an endotoxemic rat model, (Emerson et al. (1987) *Am. J. Med.*, 87, 27S-33S) have shown that prophylactic ATIII treatment affords protection from the decline of hemostasis associated with septicemia complicated by DIC. ATIII treatment has also been found to be effective in reducing mortality and stabilizing hemostatic parameters when administered after the presence of DIC has been established in *Klebsiella pneumoniae*-induced septicemic rats (Dickneite and Paques, (1993) *Thromb. Haemost.*, 69, 98-102). Human studies of ATIII replacement therapy have also shown promising results. Patients with septic shock and DIC showed improved survival as well as improved hematologic characteristics and organ function parameters with ATIII substitution (Blauhut et al., (1985) *Thromb. Res.*, 39, 81-89); (Delsharnmar et al., (1989). *J. Intern. Med.*, 225, 21-27); (Fourrier et al., (1993) *Chest*, 104, 882-888); (Hellgren et al., (1984b) *Thromb. Res.*, 35, 459-466); (Jochum, (1995) *Semin. Hematol.*, 32, 19-32). Review of the various patient trials showed a survival rate ranging from 64-97% (combined, 76%) among those receiving ATIII replacement, compared to a survival range of 7.6-25% (combined, 19%) (Vinazzer, (1995) *Clin. Appl. Thrombosis/Hemostasis*, 1, 62-65). These studies showed promising responses to ATIII concentrates in the treatment of septic DIC. However, very large doses of ATIII were required (90-120 U/kg/day) (Fourrier et al., (1993) *Chest*, 104, 882-888); (Jochum, (1995) *Semin. Hematol.*, 32, 19-32) (See also Warren B L et al., "High-dose antithrombin III in severe sepsis: a randomized controlled trial." *JAMA*. 2001 17; 286(15):1869-78).

2. ATIII Cleavage

Originally, the term protease referred to enzymes that cleaved the peptide bonds of low molecular weight polypeptides, and the term proteinase referred to enzymes that cleaved the peptide bonds of higher molecular weight proteins. More recently, the distinction between these two terms has become blurred in practical usage. In accordance with modern usage, this application also uses the term protease to refer to an enzyme that cleaves peptide bonds of proteins.

There are a variety of proteases that cleave the reactive loop of ATIII without the production of stable inhibitory complexes. These proteases can potentiate the expression of thrombin and fXa enxymatic activity by cleaving and inactivating the primary inhibitor of these coagulation factors, antithrombin III. Human neutrophil elastase (HNE) can cleave and inactivate ATIII. The primary cleavage sites for HNE are in the ATIII reactive loop, and their location can be described using the standard nomenclature of Schechter and Berger (Schechter, I, and Berger, A. (1967) *Biochem. Biophys. Res. Commun.* 27:157-162, which is herein incorporated by reference at least for material related to ATIII cleavage and amino acid designations), wherein the amino acids of the reactive loop are referred to based on their location relative to the P1-P1' peptide bond that is cleaved by the thrombin or factor Xa during inhibitory complex formation. Residues amino terminal to this bond are designated P2, P3, etc, and those on C terminal to it are designated P2', P3', etc. HNE inactivates ATIII by cleavage after its P5-Val and P4-Ile residues (Carrell and Owen, (1985) Nature, 317, 730-732 which is herein incorporated by reference at least for material related to ATIII cleavage and amino acid desigantions).

Those of skill in the art understand that different allelic variants of ATIII and different species variants of ATIII for example, have an analogous site that is cleaved during inhibitory complex formation, and that this can readily be determined. Because the absolute position of this site in the numbered sequences of different ATIIIs may change, a standard nomencature is employed to designate the relationship of reactive loop amino acids to the point of cleavage during inhibitory complex formation. (Schechter, I, and Berger, A. 1967. Biochem. Biophys. Res. Commun. 27:157-162).

3. Heparin/HSPG Activation of ATIII

In the absence of activating cofactors, ATIII's are a less efficient inhibitor of the target enzymes. The basal rate of inhibition in the absence of cofactors is referred to as "progressive" activity. Second order rate constants for progressive ATIII inhibition of thrombin and factor Xa are typically in the $10^3$-$10^4$ $M^{-1}sec^{-1}$ range. These rates, however, typically are accelerated by a factor of more than a thousand (i.e. into the $10^6$-$10^7$ $M^{-1}sec^{-1}$ range) when certain kinds of sulfataed glycosaminoglycan cofactors (heparin or heparan sulfate proteoglycans (HSPG)) bind to ATIII. Heparin is a widely used pharmaceutical that has been administered as an anticoagulant since the 1940s, while heparan sulfate proteoglycans (HSPGs) serve as the physiological cofactor for ATIII. HSPGs anchored to the vessel wall and matrix present heparin-like molecules to circulating blood and serve to localize and activate ATIII on surfaces where coagulation enzymes are generated.

4. Variants of ATIII

It is understood that when variants are referred to, the variants designate specific properties dependent on the specific substitutions denoted, however, other substitutions, deletions, and/or insertions, for example, conservative substitutions, insertions, and/or deletions at positions other than the specifically denoted positions are also contemplated provided the variants retain the disclosed activities.

Disclosed are variants of ATIII that have desireable properties. Disclosed are variants of ATIII that have increased protease resistance but retain observable anti-thrombin and/or anti-fXa activities. Also disclosed are variants of ATIII that have increased protease resistance and increased anti-thrombin and/or anti-fXa activities. Disclosed are variants of ATIII that have increased protease resistance and retain greater observable anti-thrombin activity than observable anti-fXa activity. Disclosed are variants of ATIII that have increased protease resistance and retain greater observable anti-fXa activity than observable anti-thrombin and activity. Also disclosed are antithrombin variants that have a combined activity towards thrombin and fXa.

Disclosed are variants of ATIII that retain or have increased protease resistance and retain thrombin and/or fXa inhibition activities. Also disclosed are variants of ATIII that retain or have increased protease resistance and increased thrombin and/or fXa inhibition activities with respect to plasma ATIII.

Disclosed are variants of ATIII that retain or have increased protease resistance and retain greater thrombin inhibition activity than fXa inhibition activity. Disclosed are variants of ATIII that retain or have increased protease resistance and retain greater fXa inhibition activity than thrombin inhibition activity. Also disclosed are antithrombin variants that have a combined activity towards thrombin and/or fXa, as well as variants that have an increased combined activity to thrombin and/or fXa.

The combined activity takes into account the ATIII's resistance to proteases and its ability to complex with thrombin and/or fXa and continue to inhibit thrombin and/or fXa. The combined activity can be determined by the coupled assay disclosed in Example 2. The screening assay involves three steps corresponding to (1) treatment of the ATIII with protease(s), such as HNE and/or catG, or no enzyme, (2) formation of inhibitory complexes between active (uncleaved) ATIII molecules and thrombin or factor Xa, and (3) assay of uninhibited thrombin or factor Xa with a chromogenic substrate. The level of thrombin or factor Xa activity observed is related to the ability of the ATIII variant to form inhibitory complexes with thrombin or factor Xa and on its ability to resist cleavage and inactivation by hne or catG. This assay can be performed as described in Example 2. It is understood that this assay can be performed, for example, for thrombin activity alone, fXa activity alone, or a combination of the two activities.

The coupled assay provides a residual thrombin activity. This residual thrombin activity represents the amount of thrombin enzymatic activity that remains, typically after a 10 minute incubation with the ATIII or variant ATIII. The residual thrombin activity is quantified by taking the ratio of the residual thrombin activity after incubation with an ATIII to the residual thrombin activity after incubation with buffer. Thus, the lower the residual thrombin activity, the more inhibition of thrombin that has taken place by the ATIII. The residual thrombin inhibition activity can be calculated by subtracting the residual thrombin activity from 100 (100 represents a state of effectively no inhibition). It is understood that as variants of ATIII obtain better inhibitory activity, the timing of the reaction can be decreased, to for example, 9, 8, 7, 6, 5, 4, 3, 2, or 1 minute. For variants of ATIII having less inhibitory activity the incubation can be increased to, for example, 12, 14, 16, 18, 20, 25, 30, 45, or 60 minutes. One or more assays can be performed with different incubation times to obtain residual thrombin activities that fall between 1 and 100, and, for example, at least two times can be performed for a given ATIII so that it can be verified that the assay is being performed in the analytical range. One knows the assay is being performed in the analytical range when two different assays run with two different incubation times produce different residual thrombin activities.

Disclosed are ATIIIs that have a base thrombin inhibition activity of at least 5%, 10%, 15%, 20%, 25%, 30% 35%, 40%, 45%, 50%, 55%, 60%, 65%, 70%, 75%, 80%, 85%, 90%, 95%, 96%, 97%, 98%, and 99%. It is also understood that each individual ATIII variant discussed in the tables in the Examples also has a base thrombin inhibition activity which can be determined from the disclosed residual activities and each of these base thrombin inhibition activities is specifically disclosed herein. It is understood that these percentages of base thrombin activity can be calculated from a base residual thrombin activity obtained at any time which provides data in the analytical range of the assay, unless otherwise indicated.

The coupled assay provides a residual fXa activity. This residual fXa activity represents the amount of fXa enzymatic activity that remains, typically after a 10 minute incubation with the ATIII or variant ATIII. The residual fXa activity is quantified by taking the ratio of the residual fXa activity after incubation with an ATIII to the residual fXa activity after incubation with buffer. Thus, the lower the residual fXa activity, the more inhibition of fXa that has taken place by the ATIII. The residual fXa inhibition activity can be calculated by subtracting the residual fXa activity from 100 (100 represents a state of effectively no inhibition). It is understood that as variants of ATIII obtain better inhibitory activity, the timing of the reaction can be decreased, to for example, 9, 8, 7, 6, 5, 4, 3, 2, or 1 minute. For variants of ATIII having less inhibitory activity the incubation can be increased to, for example, 12, 14, 16, 18, 20, 25, 30, 45, or 60 minutes. One or more assays can be performed with different incubation times to obtain residual fXa activities that fall between 1 and 100, and, for example, at least two times can be performed for a given ATIII so that it can be verified that the assay is being performed in the analytical range. One knows the assay is being performed in the analytical range when two different assays run with two different incubation times produce different residual fXa activities.

Disclosed are ATIIIs that have a base fXa inhibition activity of at least 5%, 10%, 15%, 20%, 25%, 30% 35%, 40%, 45%, 50%, 55%, 60%, 65%, 70%, 75%, 80%, 85%, 90%, 95%, 96%, 97%, 98%, and 99%. It is also understood that each individual ATIII variant discussed in the tables in the Examples also has a base fXa inhibition activity which can be determined from the disclosed residual activities and each of these base fXa inhibition activities is specifically disclosed herein. It is understood that these percentages of base fXa inhibition activity can be calculated from a base residual fXa activity obtained at any time which provides data in the analytical range of the assay unless otherwise indicated.

For example, residual thrombin activity for LEAI 474 can be determined as follows. The data in Table 8 was produced as the coupled assay is disclosed herein. The residual thrombin activity for LEAI 474 for experiment number 11 would produce a thrombin inhibition activity following hne treatment of 100−11=91. LEAI 474 in experiment 11 also had a thrombin inhibition activity following catG treatment of 100−1=99. The residual fXa activity for LEAI 474 for experiment number 11 would produce a fXa inhibition activity in the presence of hne of 100−2=98. LEAI 474 in experiment 11 also had a inhibition activity in the presence of catG of 100−2=98.

The disclosed variant ATIIIs can also be characterized by predicting their effects on the half lives of their target enzymes. The predicted half life refers to the length of time that thrombin or fXa remain active in vivo following bolus injection of ATIIIs as described herein.

Disclosed are variant ATIIIs which according to their substrate and inhibitor properties lead to a predicted half life of thrombin and/or fXa enzymatic activity at 60 minutes after bolus administration that is greater than or equal to or less than or equal to or equal to 0.9, 0.8, 0.7, 0.6, 0.5, 0.4, 0.3, 0.2, 0.1, 0.05, 0.01, 0.001, 0.0001, 0.00001, 0.000001, 0.0000001, 0.00000001, or 0.000000001 of the half life following plasma ATIII administration as calculated using Equation 3 of Example 5. The substrate and inhibitor properties can be obtained as disclosed herein in Example 3 to produce, for example, the data in FIGS. 4A and B. FIGS. 4A and 4B also represent data produced using Equation 3 of Example 5. It is understood that in some embodiments, the fXa enzymatic activity can be determined at different times, such as 1, 5, 10, 20, 30, 40, 50, or even 70, 80, 90, or 100, or more minutes. The disclosed specific halflives for 60 minutes also disclosed for each other length of time, such as 1 minute.

An ATIII variant that has increased protease resistance is one that is cleaved at a slower rate by a given amount of protease than is an equivalent amount of similarly treated plasma-derived ATIII. Cleavage of the reactive loop of an ATIII molecule causes it to relax and undergo a protein conformational change that can be readily detected as an electrophoretic mobility shift to a slower migrating form. Therefore, when exposed to protease, ATIII variants with increased protease resistance are converted to this slower mobility, cleaved and relaxed conformation at a lesser rate than is observed for an equivalent amount of similarly treated plasma-derived ATIII. Non-target protease cleavage of the ATIII reactive loop and relaxation of ATIII variants that retain the ability to inhibit target enzymes, such as thrombin and factor Xa, also reduces the ability to inhibit these target enzymes. The assay that can be used to determine the extent of ATIII cleavage is an SDS polyacrylamide gel electrophoresis assay where the gel is run under non-reducing conditions. Standard protein manipulation techniques can be used to prepare the ATIII for analysis. Disclosed are ATIII variants that are cleaved by a protease at less than or equal to 99%, 95%, 90%, 85%, 80%, 75%, 70%, 65%, 60%, 55%, 50%, 45%, 40%, 35%, 30%, 25%, 20%, 15%, 10%, 5%, 1%, 0.1%, 0.01% of the rate of plasma ATIII.

An ATIII variant that has increased HNE resistance is one that is cleaved at a slower rate by a given amount of HNE than is an equivalent amount of similarly treated plasma-derived ATIII. Therefore, when exposed to HNE, ATIII variants with increased HNE resistance are converted to the slower electrophoretic mobility, cleaved and relaxed conformation at a lesser rate than is observed for an equivalent amount of similarly treated plasma-derived ATIII. Disclosed are ATIII variants that are cleaved by hne at less than or 99%, 95%, 90%, 85%, 80%, 75%, 70%, 65%, 60%, 55%, 50%, 45%, 40%, 35%, 30%, 25%, 20%, 15%, 10%, 5%, 1%, 0.1% or 0.01% of the rate of plasma ATIII.

An ATIII variant that has increased cathepsin G resistance is one that is cleaved at a slower rate by a given amount of cathepsin G than is an equivalent amount of similarly treated plasma-derived ATIII. Therefore, when exposed to cathepsin G, ATIII variants with increased cathpesin G resistance are converted to the slower electrophoretic mobility, cleaved and relaxed conformation at a lesser rate than is observed for an equivalent amount of similarly treated plasma-derived ATIII. Disclosed are ATIII variants that are cleaved by cathepsin G at less than or 99%, 95%, 90%, 85%, 80%, 75%, 70%, 65%, 60%, 55%, 50%, 45%, 40%, 35%, 30%, 25%, 20%, 15%, 10%, 5%, 1%, 0.1% or 0.01% of the rate of plasma ATIII.

It is also understood that certain disclosed variants may not have an increased protease resistance, but yet still retain some level of thrombin and/or fXa inhibition activity. Thus also disclosed are ATIII variants that have at least 99%, 95%, 90%, 85%, 80%, 75%, 70%, 65%, 60%, 55%, 50%, 45%, 40%, 35%, 30%, 25%, 20%, 15%, 10%, 5%, 1%, 0.1%, or 0.01% thrombin and/or fXa inhibition activity of plasma ATIII even if they do not have increased protease resistance.

Observable anti-thrombin and anti-fXa activity can be defined by results from the coupled assay (CA) described in Example 2. Observable anti-thrombin activity is defined as the ability of an ATIII variant to reduce residual thrombin activity in the arm of the coupled assay that contains no added HNE or cathepsin G, to less than 99%, 95%, 90%, 85%, 80%, 75%, 70%, 65%, 60%, 55%, 50%, 45%, 40%, 35%, 30%, 25%, 20%, 15%, 10%, 5%, 1%, 0.1%, or 0.01% of the control value of thrombin activity obtained with no ATIII addition. The data in Tables 4-8 represent variants within one or more of these disclosed ranges, and it is understood that the data disclosed in Tables 4-8, and elsewhere herein can be used to determine the percent activity.

Observable anti-fXa activity is defined as the ability of an ATIII variant to reduce residual factor Xa activity in the arm of the coupled assay that contains no added HNE or cathepsin G, to less than 99%, 95%, 90%, 85%, 80%, 75%, 70%, 65%, 60%, 55%, 50%, 45%, 40%, 35%, 30%, 25%, 20%, 15%, 10%, 5%, 1%, 0.1%, or 0.01% of the control value obtained with no ATIII addition. The data in Tables 4-8 represent variants within one or more of these disclosed ranges, and it is understood that the data disclosed in Tables 4-8, and elsewhere herein can be used to determine the percent activity.

Disclosed are variants of ATIII that have resistance or increased resistance to hne and/or resistance or increased resistance to catG and retain observable anti-thrombin and/or anti-fXa activities. Also disclosed are variants of ATIII that have resistance or increased resistance to hne and/or resistance or increased resistance to catG and have increased anti-thrombin and/or anti-fXa activities. Disclosed are variants of ATIII that have resistance or increased resistance to hne and/or resistance or increased resistance to catG and retain greater observable anti-thrombin activity than observable anti-fXa activity. Disclosed are variants of ATE that have resistance or increased resistance to hne and/or resistance or increased resistance to catG and retain greater observable anti-fXa activity than observable anti-thrombin and activity.

CatG resistance is typically provided by reduction of cathepsin G-preferred residues (large hydrophobic amino acids such as phenylalanine, tyrosine and tryptohphan) in the reactive loop. Or, when cathepsin G-preferred residues do occur in the reactive loop, catG sensitivity can be decreased by placing acidic or polar amino acids carboxy or amino terminal to them. For example at 3.Bb that contains phenylalanines at the P4 and P5 positions (Table 4), or BbA.413 and 414 that contain respectively F and W at P4 (Table 5), exhibit sensitivity to inactivation by cathepsin G. However, introduction of an E in the P3 position of Bb402, immediately C terminal to the P4 and P5 phenylalanines of Bb, reduces catG sensitivity. Similarly, D (Bb.401), N (Bb.403), Q (Bb.404) and G (Bb.405) P3 substitutions on a Bb background also elicited reduced sensitivity to catG. Several variants with P4 phenylalanine residues (BbA.413, 13C434, 7EVEA.453) exhibited less than the expected catG sensitivity, suggesting that an amino terminal acidic amino acid, such as a negatively charged amino acid, such as glutamic acid, also serves to reduce cleavage at adjacent catG recognition sites.

HNE resistance is provided by avoidance of HNE-preferred residues (i.e., medium-sized hydrophobic amino acids such as isoleucine, valine and alanine in the reactive loop. Or, when HNE-preferred residues are present in the reactive loop, resistance to HNE cleavage can be conferred by placing a negatively charged glutamic acid amino terminal to them. For example, plasma-derived ATIII is sensitive to HNE cleavage after its P4 isoleucine and P6 valine. However, introduction of glutamic acid residues in the P7 or P5 positions, immediately amino terminal to the HNE sensitive residues in the P6 or P4 positions, decreased HNE sensitivity (Example 2, Tables 5, 6, 7).

In general, resistance to proteolytic inactivation can be obtained by avoiding cathepsin G- and HNE-preferred residues in the reactive loop. However, when it is desirable to have some cathepsin G- and/or HNE-preferred residues in the reactive loop for the purpose of promoting inhibitory reactions with thrombin and fXa, these residues can be protected from cleavage by placing glutamic acid/acidic residues/polar residues N and/or C terminal to them.

To achieve thrombin inhibition activity in combination with increased resistance to proteolytic inactivation, typically (1) the P4 and P6 residues should be compatible with internalization of the reactive loop polypeptide as strand 4 of sheet A during serpin inhibitory complex formation, (2) the P4 residue is hydrophobic in order to accommodate interactions with thrombin, and (3) the P7 and/or P5 residue is a glutamic acid, an acidic amino acid, or other amino acids, that inhibits proteolytic cleavage of adjacent, HNE- or catG-preferred P6 or P4 residues. For example, variants where P6 is L or V and P4 is A, V, I, L, F, or W, and P7 and P5 are glutamic acid are variant ATIII's with profiles of progressive thrombin inhibition activity and increased resistance to protelytic inactivation (Example 2, Tables 6 and 7).

To achieve heparin-dependent and progressive thrombin inhibition activity in combination with increased proteinase resistance, typically (1) the P4 and P6 residues should be compatible with internalization of the reactive loop polypeptide as strand 4 of sheet A during serpin inhibitory complex formation, (2) the P4 residue should be hydrophobic in order to accommodate interactions with thrombin, and (3) the P5 residue should be an acidic residue, such as a negatively charged residue, such as, glutamic acid or other amino acid that inhibits proteolytic cleavage of an adjacent, HNE- or catG-preferred P4 residue, and (4) P7 should be an alanine. For example, variants where P7 is A, P6 is L, P5 is glutamic acid, and P4 is A are variant ATIIIs with good heparin dependent and progressive anti-thrombin activity and good resistance to proteolytic inactivation profiles (Example 2, Table 8).

To achieve factor Xa inhibition activity in combination with increased proteinase resistance, typically (1) the P4 and P6 residues are compatible with rapid and stable internalization of the reactive loop polypeptide as strand 4 of sheet A during serpin inhibitory complex formation, (2) the P3 residue is not a basic residue, such as a positively charged residue, such as arginine, and (3) the P7 and/or P5 residue is/are a acidic residue, such as a negatively charged residue, such as, glutamic acid or other aa that inhibits cleavage if the adjacent P4 or P6 positions are occupied by HNE- or catG-preferred residues. For example, variants where P6 is L, G or V and P3 is not R, and P7 and/or P5 are glutamic acid constitute antithrombins with profiles of progressive fXa inhibition activity and increased resistance to proteolytic inactivation (Example 2, Tables 5-8).

To achieve thrombin inhibition activity and factor Xa inhibition activity in combination with increased proteinase resistance, typically (1) the P4 and P6 residues should be compatible with internalization of the reactive loop polypeptide as strand 4 of sheet A during serpin inhibitory complex formation, (2) the P4 residue is hydrophobic in order to accommodate interactions with thrombin, (3) the P3 residue is not a basic residue, such as a positively charged residue, such as an arginine to accommodate reaction with fXa, and (4) the P7 and/or P5 residue is a negatively charged glutamic acid or other aa that inhibits protease cleavage if the adjacent P4 or P6 positions are occupied by HNE- or catG-preferred residues. For example, variants where P6 is L, P5 is E, P4 is A, and P3 is I, N, Q, Y, or H are variant ATIIIs with profiles of observable progressive and heparin-dependent anti-thrombin and anti-fXa activity and have increased proteinase resistance (see Example 2, Table 8).

Disclosed are variants with substitutions that produce inhibitors that have the properties disclosed herein. Disclosed are substitutions, wherein the subtitutions are made at positions P1, P2, P3, P4, P5, P6, P7, and/or P8 of ATIII either alone or in combination.

Disclosed are substitutions, wherein the subtitution made at position P2, alone or collective with substitutions at either P3, P4, P5, P6, P7, and/or P8 or any other variants disclosed herein, is P.

Disclosed are substitutions, wherein the subtitution made at position P3, alone or collective with substitutions at either P2, P4, P5, P6, P7, and/or P8 or any other variants disclosed herein, is D, E, G, H, 1, K, L, N, P, Q, R, S, W, or Y.

Disclosed are substitutions, wherein the subtitution made at position P3, alone or collective with substitutions at either P2, P4, P5, P6, P7, and/or P8 or any other variants disclosed herein, is D, E, H, K, L, P, Q, R, W, or Y.

Disclosed are substitutions, wherein the subtitution made at position P4, alone or collective with substitutions at either P2, P3, P5, P6, P7, and/or P8 or any other variants disclosed herein, is A, F, G, L, N, P, Q, V, or W.

Disclosed are substitutions, wherein the subtitution made at position P4, alone or collective with substitutions at either P2, P3, P5, P6, P7, and/or P8 or any other variants disclosed herein, is L, N, Q, V, or W.

Disclosed are substitutions, wherein the subtitution made at position P5, alone or collective with substitutions at either P2, P3, P4, P6, P7, and/or P8 or any other variants disclosed herein, is E, F, G, P, D, S, T, N, Q, H, R, K, or V.

Disclosed are substitutions, wherein the subtitution made at position P6, alone or collective with substitutions at either P2, P3, P4, P5, P7, and/or P8 or any other variants disclosed herein, is E, G, L, or T.

Disclosed are substitutions, wherein the subtitution made at position P7, alone or collective with substitutions at either P2, P3, P4, P5, P6, and/or P8 or any other variants disclosed herein, is E, N, Q, V, L, F, S, T, or H.

Disclosed are substitutions, wherein the subtitution made at position P8, alone or collective with substitutions at either P2, P3, P4, P5, P6, P7, and/or P8, or any other variants disclosed herein, is E.

Disclosed are variants, having at least one substitution at position P2, P3, P4, P5, P6, or P7, wherein the substitution at P2 can be P, wherein the substitution at P3 can be D, E, G, H, I, K, L, N, P, Q, R, S, W, or Y, wherein the substitution at P4 can be A, F, G, L, N, P, Q, V, or W, wherein the substitution at P5 can be E, F, G, or P, wherein the substitution at P6 can be E, G, L, or T, wherein the substitution at P7 can be E or Q.

Disclosed are variants, having at least one substitution at position P2, P3, P4, P5, P6, or P7, wherein the substitution at P2 can be P, wherein the substitution at P3 can be D, E, H, K, L, P, Q, R, W, or Y, wherein the substitution at P4 can be L, N, Q, V, or W, wherein the substitution at P5 can be E or F wherein the substitution at P6 can be G or L, wherein the substitution at P7 can be E.

Disclosed are variants, having at least one substitution at position P2, P3, P4, P5, P6, or P7, wherein the substitution at P2 can be P, wherein the substitution at P3 can be D, E, G, H, I, K, L, N, P, Q, R, S, W, or Y, wherein the substitution at P4 can be A, F, G, L, N, P, Q, V, or W, wherein the substitution at P5 can be D, E, F, G, H, K, N, P, Q, R, S, T, or V wherein the substitution at P6 can be E, G, L, or T, wherein the substitution at P7 can be E, F H, I, L N, Q, S, T, or V, or wherein the substitution at P8 can be E.

Disclosed are variants, having at least one substitution at position P2, P3, P4, P5, P6, or P7, wherein the substitution at P2 can be P, wherein the substitution at P3 can be D, E, H, K, L, P, Q, R, W, or Y, wherein the substitution at P4 can be L, N, Q, V, or W, wherein the substitution at P5 can be D, H, K, N, Q, R, S, T, or V wherein the substitution at P6 can be G or L, wherein the substitution at P7 can be F, H, L, S, T, V.

Disclosed are variants, having at least one substitution at position P2, P3, P4, P5, P6, or P7, wherein substitution at P2 can be P, wherein the substitution at P3 can be D, E, H, K, L, P, Q, R, W, or Y, wherein the substitution at P4 can be L, N, Q, V, or W.

Disclosed are variants, having at least one substitution at position P7 or P5, wherein the substitution at P7 can be G, V, L, F, S, T, N, Q, H, R, or, K, and wherein the substitution at P5 can be D, S, T, N, Q, H, R, K, V, or G.

Disclosed are variants, having at least one substitution at position P7 or P5, wherein the substitution at P7 can be E, Q, V, L, F, S, T, H, or E, and wherein the substitution at P5 can be E, F, G, P, D, S, T, N, Q, H, R, K, or V.

Disclosed are variants of antithrombin m, comprising a substitution at position P2, wherein the substitution at P2 is a P, along with at least one other substitution disclosed herein.

Disclosed are variants of antithrombin III, comprising a substitution at position P3, wherein the substitution at P3 is a D, E, H, K, L, P, Q, R, W, or Y.

Disclosed are variants of antithrombin III, comprising a substitution at position P4, wherein the substitution at P4 is a L, N, Q, V, or W, and when the substitution of W occurs with at least one other substitution disclosed herein.

Disclosed are variants of antithrombin III, comprising at least one substitution at either position P3 and P4, wherein the substitution at P3 is D, E, H, K, L, P, Q, R, W, or Y, and wherein the substitution at P4 is L, N, Q, V, or W, and at least one substitution at P2, P5, P6, P7, and P8, wherein the substitution at P2 is P, P5 is E, F, G, or P, wherein the substitution at P6 is E, G, L, or T, wherein the substitution at P7 is E or Q, and wherein the substitution at P8 is E.

Disclosed are variants of antithrombin III, comprising at least two substitutions at P3 and P4, wherein the substitution at P3 is D, E, G, H, I, K, L, N, P, Q, R, S, W, or Y, and wherein the substitution at P4 is L, N, Q, V, or W.

Disclosed are variants of antithrombin III, comprising at least two substitutions at either position P3 and P4, wherein the substitution at P3 is D, E, H, K, L, P, Q, R, W, or Y, and wherein the substitution at P4 is A, F, G, L, N, P, Q, V, or W.

Disclosed are variants of antithrombin III, comprising a substitution at least two substitutions at P2, P3 and P4, wherein the substitution at P2 is P, wherein the substitution at P3 is D, E, G, H, I, K, L, N, P, Q, R, S, W, or Y, and wherein the substitution at P4 is A, F, G, L, N, P, Q, V, or W.

Disclosed are variants of antithrombin III, comprising a substitution at least one substitution at P2, P3 and P4, wherein the substitution at P2 is P, wherein the substitution at P3 is D, E, H, K, L, P, Q, R, S, W, or Y, and wherein the substitution at P4 is L, N, Q, V, or W.

Disclosed are variants of antithrombin III, comprising a substitution at least one substitution at P3 and P4, wherein the substitution at P3 is D, E, H, K, L, P, Q, R, S, W, or Y, and wherein the substitution at P4 is L, N, Q, V, or W.

Disclosed are variants of antithrombin III, wherein the variant antithrombin III has a combined activity greater than or equal to plasma ATIII in a coupled assay.

Disclosed are variants of antithrombin III, wherein the variant antithrombin III has a combined activity greater than or equal to 2, 5, or 10, times the activity of plasma ATIII in a coupled assay.

Disclosed are variants of antithrombin III, wherein the variant antithrombin III has an increased protease resistance.

Disclosed are variants of antithrombin III, comprising a variant antithrombin III having at least 40%, 45%, 50%, 55%, 60%, 65%, 70%, 75%, 80%, 85%, 90%, or 95% identity (for example) to the sequence set forth in SEQ ID NOs: 70, 77, 78, 81, 84, 85, 86, 87, 88, 89, or 90, (for example) and wherein the variant antithrombin III comprises at least one, at least two, at least three, at least 4, at least 5, or at least 6 of any of the disclosed substitutions at positions P2, P3, P4, P5, P6, P7, or P8.

Disclosed is a variant of ATIII (472) that has L at P6, E at P5, A at P4 and N at P3 and that is resistant to cleavage and inactivation by HNE and catG and retains progressive and heparin-dependent anti-thrombin and anti-fXa inhibition properties.

Disclosed is a variant of ATIII (474) that has L at P6, E at P5, A at P4 and Q at P3 and has increased protease resistance and retains thrombin and/or fXa inhibition activity.

Disclosed is a variant of ATIII (480) that has L at P6, E at P5, A at P4 and Y at P3 and has increased protease resistance and retains thrombin and/or fXa inhibition activity.

Disclosed is a variant of ATIII (482) that has L at P6, E at P5, A at P4 and H at P3 and has increased protease resistance and retains thrombin and/or fXa inhibition activity.

Disclosed is a variant of ATIII (471) that has L at P6, E at P5, A at P4 and R at P3 and has increased protease resistance and retains thrombin and/or fXa inhibition activity.

In certain embodiments, P4 is not alanine; phenylalanine; glycine; and proline and P5 is not glutamic acid; phenylalanine; glycine; and proline, and P3 is not E, G, I, or N.

5. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 40, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci.*

USA 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

6. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

7. Nucleic Acids

There are a variety of molecules disclosed herein peptides, such as various variant ATIIIs. It is understood that these peptide based molecules can be encoded by a number of nucleic acids, including for example the nucleic acids that encode, for example, SEQ ID NO:77 It is understood that for example, when a vector is expressed in a cell, that the expressed mRNA will typically be made up of A, C, G, and U.

a) Sequences

There are a variety of sequences related to the antithrombin III which can be found at, for example, Genbank database which can be accessed at www.pubmed.gov. These sequences and others are herein incorporated by reference in their entireties as well as for individual subsequences contained therein.

One particular sequence set forth in SEQ ID No:77 is used herein, as an example, to exemplify the disclosed compositions and methods. It is understood that the description related to this sequence is applicable to any sequence related to an ATIII variant unless specifically indicated otherwise. Those of skill in the art understand how to resolve sequence discrepancies and differences and to adjust the compositions and methods relating to a particular sequence to other related sequences (i.e. sequences of ATIII). Primers and/or probes can be designed for any ATIII related nucleic acid sequence given the information disclosed herein and known in the art.

b) Primers and Probes

Disclosed are compositions including primers and probes, which are capable of interacting with nucleic acids related to the variant ATIIIs as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acids related to the variant ATIIIs or regions of the nucleic acids related to the variant ATIIIs or they hybridize with the complement of the nucleic acids related to the variant ATIIIs or complement of a region of the nucleic acids related to the variant ATIIIs gene.

The size of the primers or probes for interaction with the nucleic acids related to the variant ATIIIs in certain embodiments can be any size that supports the desired enzymatic manipulation of the primer, such as DNA amplification or the simple hybridization of the probe or primer. A typical primer or probe for nucleic acids related to the variant ATIIIs would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe for an ATIII variant can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the nucleic acids related to the variant ATIIIs typically will be used to produce an amplified DNA product that contains the region of the variant ATIII that includes one or more of positions P1, P2, P3, P4, P5, P6, P7, P8, as disclosed herein. In general, typically the size of the product will be such that the size can be accurately determined to within 3, or 2 or 1 nucleotides.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

8. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352,815-818, (1991). Such methods are well known in the art and readily adaptable for use with the compositions and methods described herein. In certain cases, the methods will be modifed to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as nucleic acids related to the variant ATIIIs, into the cell without degradation and include a promoter yielding expression of the gene in the cells into which it is delivered. In some embodiments the delivery systems are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase ImI transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pot, and env genes which are involved in the making of the protein coat. It is the gag, pot, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pot, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenovinises has been described (Berkner et al., J. Virology 61:1213-1220 (1987); Massie et al., Mol. Cell. Biol. 6:2872-2883 (1986); Haj-Ahmad et al., J. Virology 57-267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Asscociated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B 19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorproated by reference for material related to the AAV vector.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed variants or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.* 35:421-425, (1992); Pietersz and McKenzie, *Immunolog. Reviews*, 129: 57-80, (1992); and Roffler, et al., *Biochem. Pharmacol*, 42:2062-2065, (1991)). These techniques can be used for a variety of other speciifc cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/ex Vivo

As described above, the compositions can be administered in a pharmaceutically acceptable carrier and can be delivered to the subjects cells ill vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

9. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature*, 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or, alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

10. Peptides a) Protein Variants

As discussed herein there are numerous variants of the ATIII protein that are known and herein contemplated. In addition, to the disclosed functional variants related to the positions P1-P8 as disclosed herein, there are known functional naturally occurring ATIII variants at positions other than P1-P8 which also function as ATIIIs and as variant ATIIIs as disclosed herein if coupled with the disclosed P1-P8 variants. Protein variants and derivatives are well understood to those of skill in the art and can involve amino acid sequence modifications or functional fragments. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
| --- | --- | --- |
| alanine | Ala | A |
| allosoleucine | AIle | |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isoleucine | Ile | I |
| leucine | Leu | L |
| lysine | Lys | K |
| phenylalanine | Phe | F |
| proline | Pro | P |
| pyroglutamic acid | pGlu | |
| serine | Ser | S |
| threonine | Thr | T |
| tyrosine | Tyr | Y |
| tryptophan | Trp | W |
| valine | Val | V |

TABLE 2

Amino Acid Substitutions
Original ResidueExemplary Conservative Substitutions,
others are known in the art.

| | |
| --- | --- |
| Ala | ser |
| Arg | lys, gln, his |
| Asn | gln; his |
| Asp | glu |
| Cys | ser |
| Gln | asn, lys |
| Glu | asp |
| Gly | Ala |

TABLE 2-continued

Amino Acid Substitutions
Original Residue Exemplary Conservative Substitutions,
others are known in the art.

| | |
|---|---|
| His | asn; gln |
| Ile | leu; val |
| Leu | ile; val |
| Lys | arg; gln; his |
| Met | Leu; ile |
| Phe | met; leu; tyr |
| Ser | thr, asn |
| Thr | ser, gln |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Tbr; Lys, Arg; and Phe, Tyr. Such conservatively substituted variations of each explicitly disclosed sequence are included within the mosaic polypeptides provided herein.

Substitutional or deletional mutagenesis can be employed to insert or disable sites for N-glycosylation (Asn-X-Thr/Ser) or O-glycosylation (Ser or Thr). Deletions or substitutions of cysteine or methionine (for example in "neutrophil-resistant" proteins due to genration of oxidants by neutrophils) or other labile residues also may be desirable. Deletions or substitutions of potential proteolysis sites, e.g. Arg, may be accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of amines in the epsilon-amino group of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

Disulfide bonds are covalent interactions between the thiol group of two cysteine molecules. Through an oxidative reaction, the hydrogen atoms are removed from the thiol groups allowing the formation of a disulfide bridge; the resulting bonded cysteines are termed cystine. Disulfide bonds fall into to categories class I and class II. It is a class II bond which serves to stabilize the three dimensional structure of a protein by linking cysteines within a chain. A class I disulfide bond results when these interactions occur between separate chains. The formation of class I disulfide bonds can aid in the formation of dimeric proteins, an important feature which is often necessary for receptors to provide proper receptor-ligand interactions. Amino acid substitutions may be made at sites where cysteine residues occur; typically, conservative substitutions do not alter cysteine residues involved in disulfide bonds. Such substitutions may have the effect of changing protein folding or altering multimer interactions if the substituted residue is involved in disulfide bonds. It can be determined which cysteines are involved in disulfide bonds.

It is understood that one way to define the variants and derivatives of the disclosed proteins herein is through defining the variants and derivatives in terms of homology/identity to specific known sequences. For example, SEQ ID NO:77 sets forth a particular sequence of an ATIII variant and SEQ ID NO:78 sets forth a particular sequence of another variant ATIII protein. SEQ ID NOs:70, 81, and 84-87 set forth other exemplary disclosed variants of ATIII. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:77 is set forth in SEQ ID NO:79. Another nucleic acid sequence that encodes the same protein sequence set forth in SEQ ID NO:77 is set forth in SEQ ID NO:80. In addition, for example, a disclosed conservative derivative of SEQ ID NO:77 is shown in SEQ ID NO: 81, where the isoleucine (I) at position 5 is changed to a valine (V). It is understood that for this mutation all of the nucleic acid sequences that encode this particular derivative of the variant ATIII are also disclosed including for example SEQ ID NO:82 and SEQ ID NO:83 which set forth two of the degenerate nucleic acid sequences that encode the particular polypeptide set forth in SEQ ID NO:81. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

Also disclosed are fragments of the disclosed proteins and variants. Typically these fragments will retain at least one of the functions described herein, such as increased resistance to protease cleavage while retaining thrombin and/or factor Xa inhibition activity. However, it is understood that fragments that do not retain this activity, for example, can still be used to, for example, generate antibodies. It is also understood that that there are a variety of different functional activities held by ATIII, for example, anti-thrombin activity and heparin binding activity. These activities can be related but are not necessarily required. Those of skill understand how to manipulate functional domains of the disclosed ATIII variants by, for example, altering a region contributing to a particular function. ATE variants having specific functional sites removed or altered are disclosed.

Also disclosed are variants of homologs of human ATIII. For example, ATIII can be found in mammals, wherein each mammal produces a homolog of ATIII such as mouse, rabbit, bovine, sheep, frog, ostrich, and pufferfish. These homologs, for example, are functionally related and structurally related. These homologs can be interchangeable, for example, human ATE can inhibit mouse thrombin. (Jordan (1983) Archives of Biochemistry and Biophysics 227:587-595 "Antithrombin in vertebrate species: conservation of the heparin dependent mechanism." Herein incorporated by reference at least for material related to ATIII sequence homologies including all disclosed and referenced sequences of ATIII). Jordan establishes that ATIII activity is present in the blood plasma of each of the terrestrial vertebrate groups including mammals, birds, reptiles and amphibians. The purified vertebrate ATIIIs all show the following physical and functional homologies to human ATIII: 1) heparin-enhanced inhibition of both bovine thrombin and human factor Xa, 2) MW of approximately 60 Kd, and 3)-heparin-induced increases in UV fluoresence.

It is understood that the disclosed variants can be made in any homolog background. For example, the disclosed variants related to the elastase cleavage site can be made in for example, on a human ATIII background, a mouse ATIII background, a rat ATIII background, and any primate ATIII background.

11. Antibodies

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (1), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain ATIII variant binding activity are included within the meaning of the term "antibody or fragment thereof." Such antibodies and fragments can be made by techniques known in the art and can be screened for specificity and activity according to the methods set forth in the general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Also disclosed are methods for producing a hybidoma cell that produces monoclonal antibodies that recognize the variant ATIIIs. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., Proc. Natl. Acad. Sci. USA, 81:6851-6855 (1984)).

Monoclonal antibodies of the invention may be prepared using hybridoma methods, such as those described by Kohler and Milstein, Nature, 256:495 (1975) or Harlow and Lane.

Antibodies, A Laboratory Manual. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises the variant ATIIIs or fragments of the variant ATIIIs, such as fragments comprising the region of ATIII comprising at least one of positions P1, P2, P3, P4, P5, P6, P7, or P8 as disclosed herein. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of the variant ATIIIs or fragments thereof expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. Hybridoma. 1998 Dec.; 17(6):569-76; Kilpatrick K E et al. High-affinity monoclonal antibodies to PED/PEA-15 generated using 5 micrograms of DNA. Hybridoma. 2000 Aug.; 19(4): 297-302, which are incorporated herein by referenced in full for the methods of antibody production).

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of the variant ATIII antibodies as fusion proteins. The antigen is produced by inserting a gene fragment in-frame between the signal sequence and the mature protein domain of the ATIII antibody nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51-63).

The culture medium in which the hybridoma cells are cultured can then be assayed for the presence of monoclonal antibodies directed against variant ATIIIs. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Optionally, such a non-immunoglobulin polypeptide is substituted for the constant domains of an antibody of the invention or substituted for the variable domains of one antigen-combining site of an antibody of the invention to create a chimeric bivalent antibody comprising one antigen-combining site having specificity for the variant ATIIIs and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

The invention also provides fragments of antibodies which have bioactivity. The polypeptide fragments of the present invention can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with the variant ATIII. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

A variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Also provided is an antibody reagent kit comprising containers of the monoclonal antibody or fragment thereof of the invention and one or more reagents for detecting binding of the antibody or fragment thereof to the variant ATIII molecule. The reagents can include, for example, fluorescent tags, enzymatic tags, or other tags. The reagents can also include secondary or tertiary antibodies or reagents for enzymatic reactions, wherein the enzymatic reactions produce a product that can be visualized.

12. Pharmaceutical Carriers/Delivery of Pharamceutical Products

As described above, the compositions, such as variant ATIIIs, can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, and topical intranasal administration or administration by inhalant can be used. The exact amount of the compositions required will vary from subject to subject, depending on the species, age, weight and general condition of the subject the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409(1991)).

a) Pharmaceutically Acceptable Carriers

The compositions, including variant ATIIIs, can be used therapeutically in combination with a pharmaceutically acceptable carrier.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed ATIIIs, such as NR-ATIIIs, can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

The dosage ranges for the administration of the compositions are those large enough to produce the desired effect in which the symptom's of the disorder are effected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

13. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

Also disclosed are chips where at least one address is the sequences or part of the sequences set forth in any of the nucleic acid sequences disclosed herein wherein the sequence includes at least one of the variant sequences disclosed herein. Also disclosed are chips where at least one address is the sequences or portion of sequences set forth in any of the peptide sequences disclosed herein, wherein the peptide sequence comprises at least one of the ATIII variants disclosed herein.

Also disclosed are chips where at least one address is the sequences or part of the sequences set forth in any of the nucleic acid sequences disclosed herein wherein the sequence includes at least one of the variant sequences within the region defined by P1, P2, P3, P4, P5, P6, P7, or P8 as disclosed herein. Also disclosed are chips where at least one address is the sequences or portion of sequences set forth in any of the peptide sequences disclosed herein, wherein the peptide sequence comprises at least one of the ATIII variants wherein the variant comprises at least one of the variants defined by P1, P2, P3, P4, P5, P6, P7, or P8 as disclosed herein.

14. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums are. Thus, computer readable mediums on which the nucleic acids or protein sequences are recorded, stored, or saved are disclosed.

Disclosed are computer readable mediums comprising the sequences and information regarding the sequences set forth herein.

15. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

16. Compositions with Similar Funtions

It is understood that the compositions disclosed herein have certain functions, such as increased protease resistance with continued anti-thrombin and/or factor Xa activity. Disclosed herein are certain structural requirements for performing the disclosed functions, and it is understood that there are a variety of structures which can perform the same function which are related to the disclosed structures, and that these structures will ultimately achieve the same result, for example increased protease resistance with continued anti-thrombin and/or factor Xa activity.

D. Methods of Making the Compositions

The compositions disclosed herein and the compositions necessary to perform the disclosed methods can be made using any method known to those of skill in the art for that particular reagent or compound unless otherwise specifically noted. It is understood that general molecular bilogy techniques, such as those disclosed in Sambrook et al., *Molecular Cloning: A Laboratory Manual*, 2nd Edition (Cold Spring Harbor Laboratory Press, Cold Spring Harbor, N.Y., 1989) are available for making the disclosed molecules and practicing the disclosed methods unless otherwise noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356

(1984), (phosphotriester and phosphite-triester methods), and Narang et al., *Methods Enzymol.,* 65:610-620 (1980), (phosphotriester method). (Peptide nucleic acid molecules) can be made using known methods such as those described by Nielsen et al., *Bioconjug. Chem.* 5:3-7 (1994).

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a protein, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton RC et al., Techniques in Protein Chemistry IV. Academic Press, New York, pp. 257-267 (1992)).

3. Process for Making the Compositions

Disclosed are processes for making the compositions as well as making the intermediates leading to the compositions. For example, disclosed are proteins in SEQ ID NOs:77 and 78. There are a variety of methods that can be used for making these compositions, such as synthetic chemical methods and standard molecular biology methods. It is understood that the methods of making these and the other disclosed compositions are specifically disclosed.

Disclosed are proteins produced by the process comprising linking in an operative way a nucleic acid encoding a variant ATIII comprising the sequence set forth in SEQ ID NO:77 and a sequence controlling the expression of the nucleic acid.

Also disclosed are proteins produced by the process comprising linking in an operative way a nucleic acid molecule encoding a variant ATIII comprising a sequence having 80% identity to a sequence set forth in SEQ ID NO:77, and a sequence controlling the expression of the nucleic acid.

Disclosed are proteins produced by the process comprising linking in an operative way a nucleic acid molecule encoding a protein set forth in SEQ ID NO:77 wherein the nucleic acid sequence comprises a sequence that hybridizes under stringent hybridization conditions to a sequence set forth SEQ ID NO:79, or a degenerate variant thereof, and a sequence controlling the expression of the nucleic acid.

Disclosed are nucleic acid molecules produced by the process comprising linking in an operative way a nucleic acid molecule comprising a sequence encoding a peptide set forth in SEQ ID NO:77 and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth in SEQ ID NO:77 and a sequence controlling an expression of the nucleic acid molecule.

Disclosed are nucleic acids produced by the process comprising linking in an operative way a nucleic acid molecule comprising a sequence encoding a peptide having 80% identity to a peptide set forth in SEQ ID NO:77, wherein any change from the SEQ ID NO:77 are conservative changes and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclosed are animals produced by the process of adding to the animal any of the cells disclosed herein.

It is understood that another way of producing the proteins would be to use rabbit expression systems, such as those types of systems produced by Bioprotein Technologies. The disclosed molecules can be produced using these types of vectors and production systems. For example, these types of systems are disclosed EPO Patent Application N° 92 401 635.5, U.S. Pat. No. 5,965,788) and on a gene insulator (EPO Patent Application N° 00 403 658.8), and information can be found at www.bioprotein.com.

E. Methods of Using the Compositions

1. Methods of Using the Compositions as Research Tools

The disclosed compositions can be used in a variety of ways as research tools. For example, the disclosed compositions, such as SEQ ID NOs:77 and 78 can be used as reagents to study the coagulation pathways.

The compositions can be used for example as targets in combinatorial chemistry protocols or other screening protocols to isolate molecules that possess desired functional properties related to specifically binding the variant ATIIIs versus native ATIIIs.

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

2. Methods of Gene Modification and Gene Disruption

The disclosed compositions and methods can be used for targeted gene disruption and modification in any animal that can undergo these events. Gene modification and gene disruption refer to the methods, techniques, and compositions that surround the selective removal or alteration of a gene or stretch of chromosome in an animal, such as a mammal, in a way that propagates the modification through: the germ line of the mammal. In general, a cell is transformed with a vector which is designed to homologously recombine with a region of a particular chromosome contained within the cell, as for example, described herein. This homologous recombination event can produce a chromosome which has exogenous DNA introduced, for example in frame, with the surrounding DNA. This type of protocol allows for very specific mutations, such as point mutations, to be introduced into the genome contained within the cell. Methods for performing this type of homologous recombination are disclosed herein.

One of the preferred characteristics of performing homologous recombination in mammalian cells is that the cells should be able to be cultured, because the desired recombination event occurs at a low frequency.

Once the cell is produced through the methods described herein, an animal can be produced from this cell through either stem cell technology or cloning technology. For example, if the cell into which the nucleic acid was transfected was a stem cell for the organism, then this cell, after transfection and culturing, can be used to produce an organism which will contain the gene modification or disruption in germ line cells, which can then in turn be used to produce another animal that possesses the gene modification or disruption in all of its cells. In other methods for production of an animal containing the gene modification or disruption in all of its cells, cloning technologies can be used. These technologies generally take the nucleus of the transfected cell and either through fusion or replacement fuse the transfected nucleus with an oocyte which can then be manipulated to produce an animal. The advantage of procedures that use cloning instead of ES technology is that cells other than ES cells can be transfected. For example, a fibroblast cell, which is very easy to culture can be used as the cell which is transfected and has a gene modification or disruption event take place, and then cells derived from this cell can be used to clone a whole animal.

The disclosed nucleic acids, for example, that encode SEQ ID NO:77 and 78, can be used in vectors designed to modify a gene of interest by, for example, homologous recombination.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Expression of Recombinant ATIII Variants a) Construction of a wtATIII *Drosophila* Expression Vector pMT/BiP was purchased from Invitrogen (Carlsbad, Calif.) and all primers were synthesized by Sigma-Genosys. A modified human ATIII cDNA encoding amino acids 33-464, which contains a silent Not I restriction site at amino acid 415 was generated by PCR amplification from normal human liver cDNA (Invitrogen, Carlsbad, Calif.). Two separate PCR products were generated using the Bgl II containing forward primer 5'-CAGAGATCTCACGGGAGCCCTGTG-GACATC-3'(SEQ ID NO:71) and the Not I containing reverse primer 5'-CATGCGGCCGCTTCACTGCCT-TCTTC-3' (SEQ ID NO:72) in one reaction and the Not I containing forward primer 5'-GTACGGCCGCAAGTAC-CGCTGTTGTG-3' (SEQ ID NO:73) and the XbaI containing reverse primer 5'-CTGTCTAGATTACTTAACGC-GAGGGTTGGCTAC-3' (SEQ ID NO:74) in another reaction, both using Taq High Fidelity Polymerase (Invitrogen, Carlsbad, Calif.). The first PCR product was digested with Bgl II and Not I while the second product was digested with Not I and Xba I. The digested fragments were gel isolated and used in a three-way ligation reaction with the plasmid pMT/BiP to generate pMT/BiP-ATIII (33-464). Ligation products were transformed into DHSD☐ competent *E. coli* cells (Invitrogen, Carlsbad, Calif.) and plated onto Luria Broth plates containing ampicillin. Insert containing clones were sequenced to verify that the Not I site was introduced and to confirm the fidelity of the PCR reaction.

b) Construction of a beta-ATIII *Drosophila* Expression Vector

A pMT/BiP expression vector containing human ATIII with a serine 137 to alanine mutation (pMT/BiP-ATIII S137A) was constructed as follows. Two overlapping PCR products were generated using the plasmid pMT/BiP-ATIII (33-464) as a template. The first PCR product was generated with the Bgl II forward primer 5'-CAGAGATCTCACGG- GAGCCCTGTGTGGACATC-3' (SEQ ID NO:71) and the serine to alanine change reverse primer 5'-GCTGATAC-TAACTTGGAGGCTTTGTTGGCTTTTCGATAG-3' (SEQ ID NO:75). The second product was amplified with the serine to alanine forward primer 5'-CTATCGAAAAGCCAA-CAAAGCCTCCAAGTTAGTATCAGC-3' (SEQ ID NO:76) and the reverse Xba I primer 5'-CTGTCTAGATTACT-TAACGCGAGGGTTGGCTAC-3' (SEQ ID NO:74). The two PCR fragments were gel isolated and knit together by PCR using outside primers. The resulting PCR product was digested with Bgl I and Xba I and cloned into pMT/BiP.

c) Mutations

Amino acid mutations in the reactive loop of human ATIII cDNA were generated by replacing the NotI-XbaI restriction fragment containing the wild-type reactive loop sequence with a mutant fragment that was generated by PCR. This process was facilitated by introducing a translationally silent Not I site 5' of the reactive loop in pMT/BiP-ATIII (S137A) (see above). Forward oligomers containing a Not I site and reactive loop sequence changes (see Table 3) were used in individual PCR reactions with the reverse primer 5'-CTG TCT AGA TTA CTT AAC ACA AGG GTT GGC TAC-3' (SEQ ID NO:74) using the wt human ATIII cDNA as a template. PCR products were restricted with Not I and Xba I and subcloned into pMT/BiP ATIII (S137A), which had been digested with Not I and Xba I and separated from the internal Not I and Xba I wt ATIII P site fragment. Clones were verified by sequencing.

TABLE 3

```
SEQ ID NO:1 Bb
5'-CAT GCG GCC GCA AGT ACC GAA GGT TTC TTC TCT GGC CGT TCG CTA AAC CCC AAC-3'

SEQ ID NO:2 Bb.401
5'-CAT GCG GCC GCA AGT ACC GAA GGT TTC TTC GAC GGC CGT TCG CTA AAC CCC AAC-3'

SEQ ID NO:3 Bb.402
5'-CAT GCG GCC GCA AGT ACC GAA GGT TTC TTC GAG GGC CGT TCG CTA AAC CCC AAC-3'

SEQ ID NO:4 Bb.403
5'-CAT GCG GCC GCA AGT ACC GAA GGT TTC TTC AAC GGC CGT TCG CTA AAC CCC AAC-3'

SEQ ID NO:5 Bb.404
5'-CAT GCG GCC GCA AGT ACC GAA GGT TTC TTC CAG GGC CGT TCG CTA AAC CCC AAC-3'

SEQ ID NO:6 Bb.405
5'-CAT GCG GCC GCA AGT ACC GAA GGT TTC TTC GGT GGC CGT TCG CTA AAC CCC AAC-3'

SEQ ID NO:7 Bb.406
5'-CAT GCG GCC GCA AGT ACC GAA GGT TTC TTC TGG GGC CGT TCG CTA AAC CCC AAC-3'

SEQ ID NO:8 Bb.A
5'-CAT GCG GCC GCA AGT ACC GAG GGT GAG GCT TCT GGC CGT TCG CTA AAC CCC AAC-3'

SEQ ID NO:9 Bb.A.411
5'-CAT GCG GCC GCA AGT ACC GAG GGT GAG ATT TCT GGC CGT TCG CTA AAC CCC AAC-3'

SEQ ID NO:10 Bb.A.412
5'-CAT GCG GCC GCA AGT ACC GAG GGT GAG CTC TCT GGC CGT TCG CTA AAC CCC AAC-3'

SEQ ID NO:11 Bb.A.413
5'-CAT GCG GCC GCA AGT ACC GAG GGT GAG TTC TCT GGC CGT TCG CTA AAC CCC AAC-3'

SEQ ID NO:12 Bb.A.414
5'-CAT GCG GCC GCA AGT ACC GAG GGT GAG TGG TCT GGC CGT TCG CTA AAC CCC AAC-3'

SEQ ID NO:13 Bb.A.415
5'-CAT GCG GCC GCA AGT ACC GAG GGT GAG GTC TCT GGC CGT TCG CTA AAC CCC AAC-3'

SEQ ID NO:14 Bb.A.416
5'-CAT GCG GCC GCA AGT ACC GAG GGT GAG CAG TCT GGC CGT TCG CTA AAC CCC AAC-3'

SEQ ID NO:15 Bb.A.417
5'-CAT GCG GCC GCA AGT ACC GAG GGT GAG AAC TCT GGC CGT TCG CTA AAC CCC AAC-3'

SEQ ID NO:16 Bb.A.418
5'-CAT GCG GCC GCA AGT ACC GAG GGT GAG GCT TCT CCT CGT TCG CTA AAC CCC AAC-3'

SEQ ID NO:17 Bb.A.419
5'-CAT GCG GCC GCA AGT ACC GAG GGT GAG ATT TCT CCT CGT TCG CTA AAC CCC AAC-3'

SEQ ID NO: 18 Bb.A.420
5'-CAT GCG GCC GCA AGT ACC GAG GGT GAG CTC TCT CCT CGT TCG CTA AAC CCC AAC-3'

SEQ ID NO:19 Bb.A.421
5'-CAT GCG GCC GCA AGT ACC GAG GGT GAG TTC TCT CCT CGT TCG CTA AAC CCC AAC-3'

SEQ ID NO:20 Bb.A.422
5'-CAT GCG GCC GCA AGT ACC GAG GGT GAG TGG TCT CCT CGT TCG CTA AAC CCC AAC-3'
```

TABLE 3-continued

SEQ ID NO:21 Bb.A.423
5'-CAT GCG GCC GCA AGT ACC GAG GGT GAG GTC TCT CCT CGT TCG CTA AAC CCC AAC-3'

SEQ ID NO:22 Bb.A.424
5'-CAT GCG GCC GCA AGT ACC GAG GGT GAG CAG TCT CCT CGT TCG CTA AAC CCC AAC-3'

SEQ ID NO:23 Bb.A.425
5'-CAT GCG GCC GCA AGT ACC GAG GGT GAG AAC TCT CCT CGT TCG CTA AAC CCC AAC-3'

SEQ ID NO:24 13.C
5'-CAT GCG GCC GCA AGT ACC GAG CTC GAG GGT GCT GGC CGT TCG CTA AAC CCC AAC-3'

SEQ ID NO:25 13.C.431
5'-CAT GCG GCC GCA AGT ACC GAG CTC GAG GCT GCT GGC CGT TCG CTA AAC CCC AAC-3'

SEQ ID NO:26 13.C.432
5'-CAT GCG GCC GCA AGT ACC GAG CTC GAG ATT GCT GGC CGT TCG CTA AAC CCC AAC-3'

SEQ ID NO:27 13.C.433
5'-CAT GCG GCC GCA AGT ACC GAG CTC GAG CTC GCT GGC CGT TCG CTA AAC CCC AAC-3'

SEQ ID NO:28 13.C.434
5'-CAT GCG GCC GCA AGT ACC GAG CTC GAG TTC GCT GGC CGT TCG CTA AAC CCC AAC-3'

SEQ ID NO:29 13.C.435
5'-CAT GCG GCC GCA AGT ACC GAG CTC GAG TGG GCT GGC CGT TCG CTA AAC CCC AAC-3'

SEQ ID NO:30 13.C.436
5'-CAT GCG GCC GCA AGT ACC GAG CTC GAG GTC GCT GGC CGT TCG CTA AAC CCC AAC-3'

SEQ ID NO:31 13.C.437
5'-CAT GCG GCC GCA AGT ACC GAG CTC GAG CAG GCT GGC CGT TCG CTA AAC CCC AAC-3'

SEQ ID NO:32 13.C.438
5'-CAT GCG GCC GCA AGT ACC GAG CTC GAG AAC GCT GGC CGT TCG CTA AAC CCC AAC-3'

SEQ ID NO:33 13.C.439
5'-CAT GCG GCC GCA AGT ACC GAG CTC GAG GCT GCT CCT CGT TCG CTA AAC CCC AAC-3'

SEQ ID NO:34 13.C.440
5'-CAT GCG GCC GCA AGT ACC GAG CTC GAG ATT GCT CCT CGT TCG CTA AAC CCC AAC-3'

SEQ ID NO:35 13.C.441
5'-CAT GCG GCC GCA AGT ACC GAG CTC GAG CTC GCT CCT CGT TCG CTA AAC CCC AAC-3'

SEQ ID NO:36 13.C.442
5'-CAT GCG GCC GCA AGT ACC GAG CTC GAG TTC GCT CCT CGT TCG CTA AAC CCC AAC-3'

SEQ ID NO:37 13.C.443
5'-CAT GCG GCC GCA AGT ACC GAG CTC GAG TGG GCT CCT CGT TCG CTA AAC CCC AAC-3'

SEQ ID NO:38 13.C.444
5'-CAT GCG GCC GCA AGT ACC GAG CTC GAG GTC GCT CCT CGT TCG CTA AAC CCC AAC-3'

SEQ ID NO:39 13.C.445
5'-CAT GCG GCC GCA AGT ACC GAG CTC GAG CAG GCT CCT CGT TCG CTA AAC CCC AAC-3'

SEQ ID NQ:40 13.C.446
5'-CAT GCG GCC GCA AGT ACC GAG CTC GAG AAC GCT CCT CGT TCG CTA AAC CCC AAC-3'

SEQ ID NO:41 7EVEA
5'-CAT GCG GCC GCA AGT ACC GAG GTC GAG GCT GCT GGC CGT TCG CTA AAC CCC AAC-3'

SEQ ID NO:42 7EVEA.451
5'-CAT GCG GCC GCA AGT ACC GAG GTC GAG ATT GCT GGC CGT TCG CTA AAC CCC AAC-3'

SEQ ID NO:43 7EVEA.452
5'-CAT GCG GCC GCA AGT ACC GAG GTC GAG CTC GCT GGC CGT TCG CTA AAC CCC AAC-3'

SEQ ID NO:44 7EVEA.453
5'-CAT GCG GCC GCA AGT ACC GAG GTC GAG TTC GCT GGC CGT TCG CTA AAC CCC AAC-3'

SEQ ID NO:45 7EVEA.454
5'-CAT GCG GCC GCA AGT ACC GAG GTC GAG TGG GCT GGC CGT TCG CTA AAC CCC AAC-3'

SEQ ID NO:46 7EVEA.455
5'-CAT GCG GCC GCA AGT ACC GAG GTC GAG GTC GCT GGC CGT TCG CTA AAC CCC AAC-3'

TABLE 3-continued

SEQ ID NO:47 7EVEA.456
5'-CAT GCG GCC GCA AGT ACC GAG GTC GAG CAG GCT GGC CGT TCG CTA AAC CCC AAC-3'

SEQ ID NO:48 7EVEA.457
5'-CAT GCG GCC GCA AGT ACC GAG GTC GAG AAC GCT GGC CGT TCG CTA AAC CCC AAC-3'

SEQ ID NO:49 7EVEA.458
5'-CAT GCG GCC GCA AGT ACC GAG GTT GAG GCT GCT CCA CGT TCG CTA AAC CCC AAC-3'

SEQ ID NO:50 7EVEA.459
5'-CAT GCG GCC GCA AGT ACC GAG GTT GAG ATT GCT CCA CGT TCG CTA AAC CCC AAC-3'

SEQ ID NO:51 7EVEA.460
5'-CAT GCG GCC GCA AGT ACC GAG GTT GAG CTC GCT CCA CGT TCG CTA AAC CCC AAC-3'

SEQ ID NO:52 7EVEA.461
5'-CAT GCG GCC GCA AGT ACC GAG GTT GAG TTC GCT CCA CGT TCG CTA AAC CCC AAC-3'

SEQ ID NO:53 7EVEA.462
5'-CAT GCG GCC GCA AGT ACC GAG GTT GAG TGG GCT CCA CGT TCG CTA AAC CCC AAC-3'

SEQ ID NO:54 7EVEA.463
5'-CAT GCG GCC GCA AGT ACC GAG GTT GAG GTC GCT CCA CGT TCG CTA AAC CCC AAC-3'

SEQ ID NO:55 7EVEA.464
5'-CAT GCG GCC GCA AGT ACC GAG GTT GAG CAG GCT CCA CGT TCG CTA AAC CCC AAC-3'

SEQ ID NO:56 7EVEA.465
5'-CAT GCG GCC GCA AGT ACC GAG GTT GAG AAC GCT CCA CGT TCG CTA AAC CCC AAC-3'

SEQ ID NO:57 LEAI
5'-CAT GCG GCC GCA AGT ACC GCT CTA GAG GCT ATT GGC CGT TCG CTA AAC CCC AAC-3'

SEQ ID NO:58 LEAI.471
5'-CAT GCG GCC GCA AGT ACC GCT CTA GAG GCT CGT GGC CGT TCG CTA AAC CCC AAC-3'

SEQ ID NO:59 LEAI.472
5'-CAT GCG GCC GCA AGT ACC GCT CTA GAG GCT AAC GGC CGT TCG CTA AAC CCC AAC-3'

SEQ ID NO:60 LEAI.473
5'-CAT GCG GCC GCA AGT ACC GCT CTA GAG GCT GAC GGC CGT TCG CTA AAC CCC AAC-3'

SEQ ID NO:61 LEAI.474
5'-CAT GCG GCC GCA AGT ACC GCT CTA GAG GCT CAG GGC CGT TCG CTA AAC CCC AAC-3'

SEQ ID NO:62 LEAI.475
5'-CAT GCG GCC GCA AGT ACC GCT CTA GAG GCT CTA GGC CGT TCG CTA AAC CCC AAC-3'

SEQ ID NO:63 LEAI.476
5'-CAT GCG GCC GCA AGT ACC GCT CTA GAG GCT AAG GGC CGT TCG CTA AAC CCC AAC-3'

SEQ ID NO:64 LEAI.477
5'-CAT GCG GCC GCA AGT ACC GCT CTA GAG GCT CCT GGC CGT TCG CTA AAC CCC AAC-3'

SEQ ID NO:65 LEAI.478
5'-CAT GCG GCC GCA AGT ACC GCT CTA GAG GCT AGT GGC CGT TCG CTA AAC CCC AAC-3'

SEQ ID NO:66 LEAI.479
5'-CAT GCG GCC GCA AGT ACC GCT CTA GAG GCT TGG GGC CGT TCG CTA AAC CCC AAC-3'

SEQ ID NO:67 LEAI.480
5'-CAT GCG GCC GCA AGT ACC GCT CTA GAG GCT TAT GGC CGT TCG CTA AAC CCC AAC-3'

SEQ ID NO:68 LEAI.481
5'-CAT GCG GCC GCA AGT ACC GCT CTA GAG GCT GGT GGC CGT TCG CTA AAC CCC AAC-3'

SEQ ID NO:69 LEAI.482
5'-CAT GCG GCC GCA AGT ACC GCT CTA GAG GCT CAT GGC CGT TCG CTA AAC CCC AAC-3' d) Recombinant Protein Expression in *Drosophila* S2 Cells

All pMT/BiP ATIII constructs were cotransfected with pCoHygro (Invitrogen, Carlsbad, Calif.) selectable plasmid into *Drosophila* S2 cells following the Invitrogen protocol for generation of stable cell lines. Cells were cultured in Ultimate Insect Cell Serum-Free Media (Invitrogen, Carlsbad, Calif.) containing hygromycin B (300 microg/ml). ATIII expression was induced by the addition of copper sulfate (100 mM). Supernatants were collected after 72 hours of induction. ATIII expression was verified by ELISA (Research Center Cat # ATIII-EIA) and Coomassie blue staining of sodium dodecyl sulfate—polyacrylamide gel electrophoresis (SDS-PAGE).

2. Example 2

Screening of ATIII Variants

Tables 4-8 present data on a variety of variants. These data include screening assay results comparing the thrombin and factor Xa inhibitory activities of different ATIII variants following their exposure to human neutrophil elastase (HNE); human neutrophil cathepsin G (catG) or no enzyme. For comparison, values for plasma-derived ATIII and recombinant beta-ATIII molecules produced in the baculovirus/Sf9 cell (N135A) or DES/S2 cell (S137A) expression systems are provided at the top of each table. Screening values for the recombinant ATIII parent of each series is also provided in each table.

The screening assay involves three steps corresponding to (1) treatment of the ATIII with HNE, catG or no enzyme, (2) formation of inhibitory complexes between active (uncleaved) ATIII molecules and thrombin or factor Xa, and (3) assay of uninhibited thrombin or factor Xa with a chromogenic substrate. The level of thrombin or factor Xa activity observed is related to the ability of the ATIII variant to form inhibitory complexes with thrombin or factor Xa and on its ability to resist cleavage and inactivation by hne or catG. It will be referred to as the "coupled assay" (CA) and is initiated in a 96-well microplate by incubating 1 microM ATIII and 50 microg/ml heparin with HNE at 10 nM, cat G at 25 nM or no enzyme (stage 1). Digests are stopped after 30 minutes at room temperature by adding secretory leukocyte proteinase inhibitor (SLPI) to 285 nM and polybrene to 50 ug/ml, together with thrombin (to 10 nM) or factor Xa (to 13.3 nM) to initiate inhibitory complex formation (stage 2). The stage 2 concentration of ATIII is 666 nM and complex formation is allowed to proceed at room temperature for 10 minutes (CA #8-17) or 30 minutes (CA #5-7), prior to the addition of chromogenic substrate (Kabi S2238 for thrombin and S2765 for fXa). (The longer E+I time in the earlier vs. the later coupled assays can be accounted for in consideration of the data.) Substrate hydrolysis is measured with a microplate reader at 405 nm for 3-5 minutes. Initial rates of chromophore appearance are proportional to the amount of residual (uninhibited) thrombin or factor Xa. Coupled assay results are expressed as percentage of the residual thrombin or factor Xa activity in samples containing no ATIII (no inhibition of thrombin or factor Xa). Values of 100% residual thrombin (rsd. Hla) or 100% residual fXa (rsd.Xa) indicate the absence of ATIII inhibitory activity, while values of 0% indicate that ATIII survived HNE/catG/no treatment in an amount capable of fully inhibiting thrombin or factor Xa under the assay conditions. To facilitate direct comparison of different variants, coupled assays (CA) used a standard stage 1 concentration of 200 ug/ml ATIII, except as noted in column 11 of the Tables.

Whereas the reactive loop of plasma-derived ATIII is sensitive to cleavage by neutrophil elastase, it is relatively resistant to cleavage by neutrophil cathepsin G. However, because substitution mutations carried by ATIII variants can introduce amino acid residues that are preferred sites for cathepsin G cleavage and other proteinases released by activated neutrophils, it is necessary to address sensitivity to several different inflammatory proteinases in the characterization of variant ATIII properties. Therefore, in the Coupled Assay disclosed herein, variant ATIIIs are pretreated with HNE or cathepsin G prior to assaying for retention of their ability to inhibit the target enzymes thrombin and factor Xa. The substrate specificity of proteinase-3, an additional proteinase that is released from the azurophilic granules of activated neutrophils, resembles that of neutrophil elastase (Rao et al., 1991, J. Biol. Chem., 266: 9540-9548), and therefore an ATIII variant☐s proteinase-3 sensitivity should resemble its HNE sensitivity.

Tables 4-8 also give information about the relative antithrombin and anti-fXa heparin cofactor activities (HCA) of selected variants. ATIIIs that inhibit thrombin or fXa efficiently in the presence of heparin have low IC50s in columns 19 and 20 of the tables, while those with lower heparin cofactor activities have higher IC50s. IC50s were determined by incubating ATIIIs at 4-900 nM with 10 nM thrombin or fXa in the presence 50 ug/ml heparin. After 3 minutes, the reactions were quenched with polybrene and chromogenic substrate S2238 (thrombin) or S2765 (fXa), and the initial rate of chromophore production (405 nm) recorded to obtain a measurement residual, uninhibited thrombin or factor Xa. IC50s were determined from plots of ATIII concentration vs. percent residual target enzyme activity.

The Bb parent of the variants in Table 5 has a reactive loop with the P7-P3 sequence EGFFS, which is identical to the P7-P3 residues from the thrombin cleavage site of fibrinogen Bβ. Bb is a good inhibitor of fXa and a reasonable inhibitor of thrombin. It is resistant to elastase inactivation, but has acquired sensitivity to inactivation by cathepsin G. Several P3 substitutions on a Bb background (401-405) retained the HNE resistance of the parent and exhibited modest to large improvements in resistance to catG inactivation. The better catG resistance of the P3 glutamic acid variant (402) may result from repulsion by glutamic acid (E226) at the bottom of the catG S1 pocket (Hof et al., EMBO J. 15:5481, 1996). A lesser degree of catG resistance for the corresponding aspartic acid substitution (401) implies that size as well as charge considerations are important here. With the exception of the P3 W substitutions (406), all Bb P3 variants lost some thrombin inhibitory capacity, but retained the ability to inhibit factor Xa efficiently. The reduction of fXa inhibitory activity by 406 appears to be context dependent since variant 479 (which has a P3 W on an LEAI background) retains the ability to inhibit factor Xa.

TABLE 4

| | P8 | P7 | P6 | P5 | P4 | P3 | P2 | P1 | CA expt | stg1 conc | rsd. IIa no add | rsd. IIa hne | rsd. IIa catG | rsd. Xa no add | rsd. Xa hne | rsd. Xa catG | HCA expt | IC50 IIa/UFH | IC50 fXa/ UFH |
|---|---|---|---|---|---|---|---|---|---|---|---|---|---|---|---|---|---|---|---|
| Plasma | T | A | V | V | I | A | G | R | #12 | 200 | 1 | 94 | 1 | 2 | 64 | 1 | #4 | 15 nM | 13 nM |
| ATIII | | | | | | | | | #14 | 200 | 5 | 100 | 1 | 2 | 101 | 2 | | | |
| | | | | | | | | | #17 | 23 | 6 | 96 | 8 | 1 | 98 | −7 | | | |
| | | | | | | | | | #17 | 7 | 22 | 97 | 15 | 15 | 96 | 12 | | | |
| | | | | | | | | | #17 | 3 | 56 | 96 | 64 | 75 | 96 | 77 | | | |
| | | | | | | | | | #17 | 1 | 88 | 96 | 86 | 90 | 94 | 88 | | | |
| ATIII | T | A | V | V | I | A | G | R | #8 | 200 | 1 | 90 | 0 | 1 | 90 | 1 | #2 | 24 nM | 17 nM |
| N135A | | | | | | | | | #9 | 200 | 2 | 100 | 2 | 2 | 106 | 1 | #3 | 22 nM | 19 nM |
| ATIII | T | A | V | V | I | A | G | R | #6 | 200 | 0 | 81 | 0 | 0 | 81 | 0 | #4 | 13 nM | 12 nM |
| S137A | | | | | | | | | #13 | 200 | 4 | 89 | 1 | 2 | 87 | 1 | | | |

TABLE 4-continued

| | P8 | P7 | P6 | P5 | P4 | P3 | P2 | P1 | CA expt | stg1 conc | rsd. IIa no add | rsd. IIa hne | rsd. IIa catG | rsd. Xa no add | rsd. Xa hne | rsd. Xa catG | HCA expt | IC50 IIa/UFH | IC50 fXa/UFH |
|---|---|---|---|---|---|---|---|---|---|---|---|---|---|---|---|---|---|---|---|
| Bb. | T | E | G | F | F | S | G | R | #10 | 200 | 12 | 27 | 100 | 1 | 1 | 89 | # | 550 nM | 60 nM |
| | | | | | | | | | #5 | 200 | 1 | 7 | 87 | 1 | 1 | 57 | #3 | 520 nM | 52 nM |
| Bb.401 | T | F | G | F | F | D | G | R | #5 | 185 | 56 | 64 | 80 | 1 | 2 | 40 | #2 | >1000 nM | 140 nM |
| Bb.402 | | | | | | E | | | #5 | 200 | 49 | 60 | 87 | 2 | 2 | 3 | #3 | >1000 nM | 140 nM |
| Bb.403 | | | | | | N | | | #5 | 200 | 54 | 70 | 84 | 2 | 5 | 50 | #3 | >1000 nM | 240 nM |
| Bb.404 | | | | | | Q | | | #5 | 200 | 33 | 52 | 71 | 1 | 3 | 32 | #3 | >1000 nM | 190 nM |
| Bb.405 | | | | | | G | | | #5 | 200 | 23 | 39 | 73 | 2 | 4 | 31 | | | |
| Bb.406 | | | | | | W | | | #10 | 42 | 93 | 98 | 98 | 92 | 97 | 98 | | | |
| | | | | | | | | | #16 | 15 | 92 | 98 | 92 | 93 | 95 | 93 | | | |

The Bb.A parent of the Table 5 variants has a reactive loop with the P7-P3 sequence EGEAS, which is a hybrid of the P7, P6 and P3 residues from the thrombin cleavage site of fibrinogen Bβ and the P5 and P4 residues of alpha-1 antitrypsin Pittsburgh. Bb.A retains thrombin inhibition activity and fXa inhibition activity and is resistant to inactivation by elastase and cathepsin G. However, its antithrombin activity is low. Replacement of the Bb.A P4 alanine with a series of larger, hydrophobic (favored in the P4 position of thrombin substrates) or polar amino acids did not improve anti-thrombin activity (411-417). This suggests that Bb.A has impaired anti-thrombin activity due to the negative influence of a non-P4 residue, rather than the presence of an amino acid that is not optimal in the P4 position of thrombin substrates.

Variant 411 with a P4 Ile substitution exhibited reduced anti-fXa activity. This result appears to be quite specific to the geometry of isoleucine because the P4 leucine (412) and P4 beta-branched valine (415) are fine. Furthermore, the effect is not due to overall size because F and W P4 substitutions (413 and 414) both retain anti-Xa activity. Increased HNE and Cat G sensitivity of the variant with a P4 W substitution (414) was observed. Increased Cat G sensitivity was also noted in the variants with P4 F, W, and Q substitutions (413, 414, 416), in accordance with the known cleavage preferences of cathepsin G.

It appears that a P2 proline subsitution on a Bb.A P4 A, L, Q, N background reduces anti-Xa activity, but the identical P2 proline substitution on a Bb.A P4 F, W, V background does not decrease factor Xa inhibition. This effect does not appear to be related to P4 size or polarity because P2 Pro/P4 F,W,V preserve antiXa activity, while P2 Pro/P4 A, I, L, Q, N do not.

TABLE 5

| | P8 | P7 | P6 | P5 | P4 | P3 | P2 | P1 | CA expt | stg1 conc | rsd. Iia no add | rsd. IIa hne | rsd. IIa catG | rsd. Xa no add | rsd. Xa hne | rsd. Xa catG | HCA expt | IC50 IIa/UFH | IC50 fXa/UFH |
|---|---|---|---|---|---|---|---|---|---|---|---|---|---|---|---|---|---|---|---|
| Plasma ATIII | T | A | V | V | I | A | G | R | #12 | 200 | 1 | 94 | 1 | 2 | 64 | 1 | #4 | 15 nM | 13 nM |
| | | | | | | | | | #14 | 200 | 5 | 100 | 1 | 2 | 101 | 2 | | | |
| | | | | | | | | | #17 | 23 | 6 | 96 | 8 | 1 | 98 | −7 | | | |
| | | | | | | | | | #17 | 7 | 22 | 97 | 15 | 15 | 96 | 12 | | | |
| | | | | | | | | | #17 | 3 | 56 | 96 | 64 | 75 | 96 | 77 | | | |
| | | | | | | | | | #17 | 1 | 88 | 96 | 86 | 90 | 94 | 88 | | | |
| ATIII N135A | T | A | V | V | I | A | G | R | #8 | 200 | 1 | 90 | 0 | 1 | 90 | 1 | #2 | 24 nM | 17 nM |
| | | | | | | | | | #9 | 200 | 2 | 100 | 2 | 2 | 106 | 1 | #3 | 22 nM | 19 nM |
| ATIII S137A | T | A | V | V | I | A | G | R | #6 | 200 | 0 | 81 | 0 | 0 | 81 | 0 | #4 | 13 nM | 12 nM |
| | | | | | | | | | #13 | 200 | 4 | 89 | 1 | 2 | 87 | 1 | | | |
| Bb.A | T | E | G | E | J | S | G | R | #5 | 200 | 99 | 103 | 102 | 2 | 3 | 2 | #2 | >1000 nM | |
| | | | | | | | | | #6 | 200 | 70 | 87 | 72 | 1 | 0 | 1 | | | |
| | | | | | | | | | #11 | 200 | 79 | 93 | 95 | 2 | 2 | 3 | | | |
| Bb.A.411 | | | | | I | | | | #5 | 200 | 76 | 86 | 80 | 78 | 100 | 80 | | | |
| | | | | | | | | | #16 | 74 | 95 | 96 | 94 | 96 | 100 | 96 | | | |
| Bb.A.412 | | | | | L | | | | #5 | 200 | 84 | 88 | 83 | 3 | 4 | 4 | | | |
| Bb.A.413 | | | | | F | | | | #5 | 198 | 87 | 92 | 102 | 5 | 5 | 14 | | | |
| Bb.A.414 | | | | | W | | | | #5 | 200 | 88 | 100 | 99 | 3 | 16 | 92 | | | |
| | | | | | | | | | #11 | 200 | 87 | 99 | 99 | 4 | 9 | 107 | | | |
| Bb.A.415 | | | | | V | | | | #6 | 200 | 46 | 70 | 49 | 1 | 1 | 1 | | | |
| | | | | | | | | | #11 | 200 | 81 | 91 | 91 | 3 | 14 | 4 | | | |
| Bb.A.416 | | | | | Q | | | | #6 | 186 | 76 | 97 | 82 | 5 | 4 | 52 | | | |
| Bb.A.417 | | | | | N | | | | #6 | 200 | 83 | 103 | 90 | 2 | 1 | 6 | | | |
| | | | | | | | | | #11 | 200 | 85 | 96 | 96 | 7 | 14 | 23 | | | |
| Bb.A.418 | T | F | G | F | J | S | P | R | #10 | 39 | 97 | 96 | 103 | 92 | 94 | 96 | | | |
| | | | | | | | | | #13 | 51 | 91 | 102 | 105 | 99 | 102 | 92 | | | |
| | | | | | | | | | #16 | 16 | 75 | 95 | 82 | 86 | 99 | 84 | | | |
| Bb.A.419 | | | | | I | | P | | #6 | 200 | 88 | 101 | 91 | 63 | 73 | 63 | | | |
| | | | | | | | | | #11 | 200 | 89 | 99 | 96 | 77 | 96 | 96 | | | |
| Bb.A.420 | | | | | L | | P | | #6 | 200 | 83 | 99 | 90 | 22 | 41 | 30 | | | |
| | | | | | | | | | #11 | 200 | 87 | 97 | 95 | 56 | 82 | 75 | | | |
| Bb.A.421 | | | | | F | | P | | #6 | 200 | 91 | 100 | 96 | 2 | 1 | 2 | | | |
| Bb.A.422 | | | | | W | | P | | #6 | 200 | 91 | 99 | 89 | 3 | 4 | 19 | | | |

TABLE 5-continued

| | P8 | P7 | P6 | P5 | P4 | P3 | P2 | P1 | CA expt | stg1 conc | rsd. IIa no add | rsd. IIa hne | rsd. IIa catG | rsd. Xa no add | rsd. Xa hne | rsd. Xa catG | HCA expt | IC50 IIa/UFH | IC50 fXa/UFH |
|---|---|---|---|---|---|---|---|---|---|---|---|---|---|---|---|---|---|---|---|
| Bb.A.423 | | | | | V | | P | | #6 | 200 | 88 | 101 | 86 | 3 | 4 | 7 | | | |
| | | | | | | | | | #11 | 200 | 89 | 102 | 96 | 17 | 36 | 29 | | | |
| Bb.A.424 | | | | | Q | | P | | #6 | 200 | 95 | 96 | 96 | 85 | 83 | 83 | | | |
| | | | | | | | | | #11 | 200 | 97 | 100 | 101 | 73 | 86 | 84 | | | |
| Bb.A.425 | | | | | N | | P | | #6 | 200 | 94 | 97 | 95 | 60 | 47 | 53 | | | |
| | | | | | | | | | #11 | 200 | 99 | 104 | 102 | 56 | 73 | 79 | | | |

The 13C parent of the variants in Table 6 has a reactive loop with the P7-P4 sequence ELEG, which is identical to the P7-P4 sequence relative to the thrombin activation site of factor XIII. 13C is approximately 20-fold more resistant to elastase inactivation than plasma-derived ATIII, and its Kapp for fXa inhibition is about 2.5 times that of plasma ATIII. However, 13C has negligible thrombin inhibitory activity. Table 6 shows that the P4 glycine plays a major role in reduced anti-IIa activity of the 13C parent and that anti-thrombin activity is efficiently restored by P4 substitution with hydrophobic amino acids (431-435). P4 substitution with polar amino acids (437 and 438) is associated with less efficient restoration of the anti-thrombin activity. These observations are in accordance with the conclusions from investigations of thrombin specificity using combinatorial peptide libraries (Harris et al., (2000) Proc. Natl. Acad. Sci. USA, 97, 7754-7759. The superiority of hydrophobic residues over polar residues in the restoration of anti-thrombin inhibitory activity is not due to more stable internalization of hydrophobic P4 residue sidechains in beta strand 4A of serpin inhibitory complexes (Huntington et al., 2000, Nature, 407, 923-926) since the variants with polar P4 substitutions (437 and 438) efficiently inhibit factor Xa. Progressive and heparin catalyzed anti-Xa inhibition and hne/catG resistance profiles of 13C P4 variants 431-435 are good, but anti-thrombin heparin cofactor activity is at least 20-fold reduced vs. WT. The absence of HNE and CatG sensitivity in the 13C P4 hydrophic substitutions (431-435 and 439-444) is unexpected and suggests that the P5 and/or P7 glutamic acid residues protect against cleavage by these enzymes. Proline substitution of the P2 glycine of the 431-435 variants reverses the improvement in thrombin inhibition, but not factor Xa inhibition, suggesting that the conformation of the ATIII reactive loop is important for association with thrombin, but not fXa.

TABLE 6

| | P8 | P7 | P6 | P5 | P4 | P3 | P2 | P1 | CA expt | stg1 conc | rsd. IIa no add | rsd. IIa hne | rsd. IIa catG | rsd. Xa no add | rsd. Xa hne | rsd. Xa catG | HCA expt | IC50 IIa/UFH | IC50 fXa/UFH |
|---|---|---|---|---|---|---|---|---|---|---|---|---|---|---|---|---|---|---|---|
| Plasma ATIII | T | A | V | V | I | A | G | R | #12 | 200 | 1 | 94 | 1 | 2 | 64 | 1 | #4 | 15 nM | 13 nM |
| | | | | | | | | | #14 | 200 | 5 | 100 | 1 | 2 | 101 | 2 | | | |
| | | | | | | | | | #17 | 23 | 6 | 96 | 8 | 1 | 98 | -7 | | | |
| | | | | | | | | | #17 | 7 | 22 | 97 | 15 | 15 | 96 | 12 | | | |
| | | | | | | | | | #17 | 3 | 56 | 96 | 64 | 75 | 96 | 77 | | | |
| | | | | | | | | | #17 | 1 | 88 | 96 | 86 | 90 | 94 | 88 | | | |
| ATIII N135A | T | A | V | V | I | A | G | R | #8 | 200 | 1 | 90 | 0 | 1 | 90 | 1 | #2 | 24 nM | 17 nM |
| | | | | | | | | | #9 | 200 | 2 | 100 | 2 | 2 | 106 | 1 | #3 | 22 nM | 19 nM |
| ATIII S137A | T | A | V | V | I | A | G | R | #6 | 200 | 0 | 81 | 0 | 0 | 81 | 0 | #4 | 13 nM | 12 nM |
| | | | | | | | | | #13 | 200 | 4 | 89 | 1 | 2 | 87 | 1 | | | |
| 13C | T | F | L | E | G | A | G | R | #10 | 200 | 18 | 68 | 76 | 75 | 2 | 1 | 2 | #4 | >1000 nM | 33 nM |
| | | | | | | | | | #14 | 200 | 44 | 41 | 39 | 1 | 2 | 1 | | | |
| 13C.431 | T | E | I | E | A | A | G | R | #8 | 200 | 14 | 25 | 19 | 2 | 2 | 1 | #2 | 550 nM | 45 nM |
| | | | | | | | | | #7 | 200 | 5 | 4 | 5 | 3 | 3 | 3 | | | |
| | | | | | | | | | #15 | 200 | 7 | 10 | 4 | 1 | 1 | 0 | | | |
| 13C.432 | | | | | I | | | | #8 | 200 | 5 | 16 | 8 | 1 | 1 | 1 | #2 | 460 nM | 45 nM |
| | | | | | | | | | #7 | 200 | 5 | 3 | 5 | 4 | 2 | 3 | | | |
| 13C.433 | | | | | L | | | | #8 | 200 | 13 | 20 | 18 | 1 | 1 | 1 | #2 | 600 nM | 30 nM |
| | | | | | | | | | #7 | 200 | 5 | 4 | 5 | 4 | 3 | 2 | | | |
| 13C.434 | | | | | F | | | | #8 | 200 | 8 | 12 | 30 | 2 | 1 | 1 | #2 | 500 nM | 17 nM |
| | | | | | | | | | #7 | 200 | 5 | 4 | 5 | 4 | 3 | 2 | | | |
| 13C.435 | | | | | W | | | | #7 | 200 | 5 | 4 | 5 | 3 | 3 | 3 | #2 | 700 nM | 34 nM |
| 13C.436 | | | | | V | | | | #14 | 60 | 57 | 70 | 56 | 3 | 11 | 5 | | | |
| 13C.437 | | | | | Q | | | | #8 | 200 | 55 | 63 | 63 | 1 | 1 | 1 | | | |
| | | | | | | | | | #7 | 200 | 7 | 8 | 5 | 3 | 3 | 2 | | | |
| 13C.438 | | | | | N | | | | #7 | 93 | 49 | 63 | 53 | 4 | 4 | 5 | #4 | >1000 nM | 22 nM |
| | | | | | | | | | #14 | 128 | 45 | 47 | 47 | 1 | 1 | 3 | | | |
| 13C.439 | T | F | I | F | A | A | P | R | #9 | 200 | 69 | 74 | 73 | 2 | 3 | 3 | | | |
| | | | | | | | | | #7 | 200 | 34 | 44 | 33 | 3 | 4 | 4 | | | |
| 13C.440 | | | | | I | | P | | #14 | 36 | 97 | 87 | 86 | 3 | 2 | 3 | | | |
| 13C.441 | | | | | L | | P | | #9 | 200 | 76 | 81 | 80 | 2 | 2 | 2 | | | |
| | | | | | | | | | #7 | 200 | 62 | 70 | 64 | 4 | 3 | 3 | | | |
| 13C.442 | | | | | F | | P | | #9 | 200 | 67 | 74 | 73 | 2 | 2 | 3 | | | |
| | | | | | | | | | #7 | 200 | 53 | 61 | 54 | 3 | 3 | 3 | | | |

TABLE 6-continued

| | P8 | P7 | P6 | P5 | P4 | P3 | P2 | P1 | CA expt | stg1 conc | rsd. IIa no add | rsd. IIa hne | rsd. IIa catG | rsd. Xa no add | rsd. Xa hne | rsd. Xa catG | HCA expt | IC50 IIa/UFH | IC50 fXa/UFH |
|---|---|---|---|---|---|---|---|---|---|---|---|---|---|---|---|---|---|---|---|
| 13C.443 | | | | | W | | P | | #10 | 200 | 83 | 93 | 95 | 2 | 1 | 2 | | | |
| | | | | | | | | | #7 | 200 | 78 | 85 | 79 | 8 | 4 | 4 | | | |
| 13C.444 | | | | | V | | P | | #10 | 200 | 44 | 55 | 52 | 2 | 2 | 2 | #2 | >1000 nM | 40 nM |
| | | | | | | | | | #7 | 200 | 6 | 14 | 5 | 3 | 3 | 3 | | | |
| | | | | | | | | | #15 | 200 | 46 | 53 | 45 | 1 | 1 | 1 | | | |
| 13C.445 | | | | | Q | | P | | #10 | 200 | 80 | 80 | 86 | 1 | 2 | 2 | | | |
| | | | | | | | | | #8 | 200 | 79 | 86 | 86 | 2 | 2 | 1 | | | |
| 13C.446 | | | | | N | | P | | #10 | 200 | 93 | 74 | 72 | 2 | 2 | 2 | | | |
| | | | | | | | | | #8 | 200 | 63 | 68 | 66 | 2 | 2 | 2 | | | |

The 7EVEA parent of the variants in Table 7 has a reactive loop with the P7-P4 sequence EVEA, which is related to the ELEG P7-P4 sequence of the factor XIII thrombin activation site. 7EVEA has good factor Xa inhibitory activity. However, its thrombin inhibitory activity is low and it is somewhat sensitive to inactivation by elastase. Table 7 indicates that certain substitutions of P4 ala on a 7EVEA background improve progressive anti-IIa activity relative to the parent (e.g., 451-454). Although, slight HNE sensitivity can be observed for variants of the 13C and 7EVEA series that inhibit thrombin, the HNE resistance of these variants is better than that of plasma-derived and recombinant parental ATIIIs. This suggests that the P7 and P5 glutamic acids on the amino terminal sides of the P6 leucine or valine and the P4 alanine inhibit cleavage by elastase, which prefers small to medium sized nonpolar amino acids. Table 7 also shows that several combinations of 7EVEA P4 substitutions with a further P2 proline replacement (462-465) had reduced anti-thrombin activity in conjunction with preserved anti-Xa activity. HNE sensitivity of the P4 W variant (vs P4 Q,V,N) was increased by a P2 proline substitution. This could reflect less efficient anti-Xa function, or derive from a P2 Pro effect on presentation of HNE cleavage site. Variant 7EVEA.451 has a favorable profile with respect to progressive inhibition of thrombin and factor Xa, catG/hne resistance, and anti-fXa heparin cofactor activity, but its anti-thrombin heparin cofactor activity is about 25-fold reduced vs. plasma-derived ATIII.

TABLE 7

| | P8 | P7 | P6 | P5 | P4 | P3 | P2 | P1 | CA expt | stg1 conc | Rsd. IIa No add | rsd. IIa hne | rsd. IIa catG | rsd. Xa no add | rsd. Xa hne | rsd. Xa CatG | HCA expt | IC50 IIa/UFH | IC50 fXa/UFH |
|---|---|---|---|---|---|---|---|---|---|---|---|---|---|---|---|---|---|---|---|
| Plasma ATIII | T | A | V | V | I | A | G | R | #12 | 200 | 1 | 94 | 1 | 2 | 64 | 1 | #4 | 15 nM | 13 nM |
| | | | | | | | | | #14 | 200 | 5 | 100 | 1 | 2 | 101 | 2 | | | |
| | | | | | | | | | #17 | 23 | 6 | 96 | 8 | 1 | 98 | −7 | | | |
| | | | | | | | | | #17 | 7 | 22 | 97 | 15 | 15 | 96 | 12 | | | |
| | | | | | | | | | #17 | 3 | 56 | 96 | 64 | 75 | 96 | 77 | | | |
| | | | | | | | | | #17 | 1 | 88 | 96 | 86 | 90 | 94 | 88 | | | |
| ATIII N135A | T | A | V | V | I | A | G | R | #8 | 200 | 1 | 90 | 0 | 1 | 90 | 1 | #2 | 24 nM | 17 nM |
| | | | | | | | | | #9 | 200 | 2 | 100 | 2 | 2 | 106 | 1 | #3 | 22 nM | 19 nM |
| ATIII S137A | T | A | V | V | I | A | G | R | #6 | 200 | 0 | 81 | 0 | 0 | 81 | 0 | #4 | 13 nM | 12 nM |
| | | | | | | | | | #13 | 200 | 4 | 89 | 1 | 2 | 87 | 1 | | | |
| 7EVEA | T | E | V | E | J | A | G | R | #16 | 114 | 31 | 73 | 20 | 2 | 3 | 4 | | | |
| 7EVEA.451 | T | E | V | E | I | A | G | R | #8 | 200 | 6 | 12 | 7 | 1 | 1 | 1 | #2 | 400 nM | 38 nM |
| | | | | | | | | | | | | | | | | | #3 | 450 nM | 50 nM |
| 7EVEA.452 | | | | | L | | | | #8 | 200 | 12 | 46 | 14 | 1 | 2 | 1 | #3 | 750 nM | 24 nM |
| 7EVEA.453 | | | | | F | | | | #8 | 200 | 14 | 35 | 62 | 1 | 1 | 2 | #3 | 450 nM | 19 nM |
| 7EVEA.454 | | | | | W | | | | #8 | 200 | 23 | 53 | 93 | 1 | 1 | 2 | #3 | 610 nM | 20 nM |
| 7EVEA.455 | | | | | V | | | | | | | | | | | | #4 | >1000 nM | 110 nM |
| 7EVEA.456 | | | | | Q | | | | #14 | 200 | 49 | 65 | 60 | 2 | 3 | 3 | | | |
| | | | | | | | | | | 81 | 97 | 89 | 101 | 14 | 15 | 9 | | | |
| 7EVEA.457 | | | | | N | | | | #8 | 180 | 59 | 71 | 67 | 2 | 2 | 2 | | | |
| 7EVEA.458 | T | E | V | E | A | A | P | R | #14 | 110 | 105 | 98 | 101 | 33 | 55 | 36 | #4 | >1000 nM | 250 nM |
| 7EVEA.459 | | | | | I | | P | | | | | | | | | | #4 | >1000 nM | 75 nM |
| 7EVEA.460 | | | | | L | | P | | | | | | | | | | | | |
| 7EVEA.461 | | | | | F | | P | | | | | | | | | | | | |
| 7EVEA.462 | | | | | W | | P | | #9 | 121 | 91 | 100 | 96 | 13 | 83 | 9 | | | |
| 7EVEA.463 | | | | | V | | P | | #9 | 93 | 90 | 94 | 98 | 5 | 9 | 4 | | | |
| 7EVEA.464 | | | | | Q | | P | | #9 | 200 | 92 | 96 | 96 | 2 | 4 | 3 | | | |
| 7EVEA.465 | | | | | N | | P | | #9 | 46 | 92 | 94 | 94 | 6 | 20 | 9 | | | |

The parent of the variants in Table 8 has a reactive loop with the P6-P3 sequence LEAI, which is identical to the P6-P3 sequence of alpha-1 antitrypsin Pittsburgh. LEAI is an efficient inhibitor of thrombin and factor Xa in the absence of heparin. It is resistant to inactivation by cathepsin G but can be cleaved by elastase due to cleavage after its P3 isoleucine. Replacement of the LEAI P3 isoleucine with N, Q, W, Y, H (472, 474, 479, 480, 482) improved HNE resistance while maintaining thrombin and factor Xa progressive inhibition, and near WT levels of heparin cofactor activity in some cases. P3 substitution with H (482) also increases HNE resistance in combination with progressive anti-fXa and heparin-catalyzed anti-thrombin and anti-t0 fXa activities that are better than plasma-derived ATIII (see Table 10).

The data suggests that the P3 D (473) substitution reduces anti-thrombin activity, but has little effect on factor Xa inhibition.

LEAI.471 shows good anti-thrombin function but reduced anti-Xa activity, even at reduced concentrations of inhibitor. LEAI.471 is an example of a variant that has better anti-thrombin than anti-Xa inhibition activity. It is a heparin-dependent anti-thrombin variant with minimal anti-Xa activity.

3. Example 3

Substrate and Inhibitor Properties of Selected ATIII Variants

Table 9 summarizes the substrate and inhibitor properties of plasma-derived ATIII and the recombinant ATIII variants LEAI (parent), LEAI.472, 474, 480, and 482. Substrate properties were determined with respect to inactivation by purified human neutrophil elastase and cathepsin G, as well as with a more physiological source of inflammatory proteinases, ARDS (acute respiratory distress syndrome) patient bronchoalveolar lavage (BAL) fluid. Inhibitor properties were determined as progressive and heparin cofactor inhibition of human thrombin and human factor Xa. The halflives of plasma-derived ATIII and the LEAI.472, 474, 480, and 482 variants were determined by assay of residual anti-thrombin and anti-Xa function. I microM ATIII was treated with 10 nM HNE, 25 nM catG, BAL fluid or no enzyme in the presence of 50 microg/ml heparin at room temperature. At various times,

TABLE 8

| | P8 | P7 | P6 | P5 | P4 | P3 | P2 | P1 | CA expt | stg1 conc | Rsd. IIa No add | rsd. IIa hne | rsd. IIa catG | rsd. Xa no add | rsd. Xa hne | rsd. Xa catG | HCA expt | IC50 IIa/UFH | IC50 fXa/UFH |
|---|---|---|---|---|---|---|---|---|---|---|---|---|---|---|---|---|---|---|---|
| Plasma ATIII | T | A | V | V | I | A | G | R | #12 | 200 | 1 | 94 | 1 | 2 | 64 | 1 | #4 | 15 nM | 13 nM |
| | | | | | | | | | #14 | 200 | 5 | 100 | 1 | 2 | 101 | 2 | | | |
| | | | | | | | | | #17 | 23 | 6 | 96 | 8 | 1 | 98 | -7 | | | |
| | | | | | | | | | #17 | 7 | 22 | 97 | 15 | 15 | 96 | 12 | | | |
| | | | | | | | | | #17 | 3 | 56 | 96 | 64 | 75 | 96 | 77 | | | |
| | | | | | | | | | #17 | 1 | 88 | 96 | 86 | 90 | 94 | 88 | | | |
| ATIII N135A | T | A | V | V | I | A | G | R | #8 | 200 | 1 | 90 | 0 | 1 | 90 | 1 | #2 | 24 nM | 17 nM |
| | | | | | | | | | #9 | 200 | 2 | 100 | 2 | 2 | 106 | 1 | #3 | 22 nM | 19 nM |
| ATIII S137A | T | A | V | V | I | A | G | R | #6 | 200 | 0 | 81 | 0 | 0 | 81 | 0 | #4 | 13 nM | 12 nM |
| | | | | | | | | | #13 | 200 | 4 | 89 | 1 | 2 | 87 | 1 | | | |
| LEAI | T | A | L | E | I | I | G | R | #9 | 124 | 3 | 96 | 4 | 2 | 88 | 2 | #2 | 45 nM | 37 nM |
| LEAI.471 | | | | | | R | | | #10 | 63 | 4 | 81 | 2 | 69 | 99 | 82 | #2 | 37 nM | 275 nM |
| | | | | | | | | | #9 | 63 | 2 | 78 | 3 | 81 | 66 | 106 | #3 | 35 nM | 320 nM |
| | | | | | | | | | #12 | 200 | 0 | 62 | 0 | 45 | 86 | 48 | | | |
| | | | | | | | | | #14 | 200 | 2 | 41 | 1 | 44 | 100 | 59 | | | |
| | | | | | | | | | #15 | 200 | 2 | 65 | 1 | 57 | 103 | 82 | | | |
| LEAI.472 | | | | | | N | | | #9 | 200 | 2 | 14 | 4 | 3 | 5 | 2 | #3 | 110 nM | 15 nM |
| | | | | | | | | | #13 | 200 | 7 | 29 | 3 | 1 | 2 | 2 | #4 | 200 nM | 38 nM |
| | | | | | | | | | #15 | 200 | 0 | 21 | 1 | 0 | 1 | 0 | | | |
| LEAI.473 | | | | | | O | | | #9 | 57 | 75 | 94 | 79 | 4 | 69 | 2 | #4 | >1000 nM | 28 nM |
| | | | | | | | | | #13 | 111 | 60 | 92 | 75 | 11 | 5 | 2 | | | |
| LEAI.474 | | | | | | Q | | | #9 | 200 | 3 | 14 | 2 | 2 | 3 | 2 | #2 | 65 nM | 20 nM |
| | | | | | | | | | #11 | 200 | 2 | 11 | 1 | 2 | 2 | 2 | #3 | 47 nM | 16 nM |
| | | | | | | | | | #12 | 200 | 0 | 16 | 1 | 1 | 1 | 1 | #4 | 50 nM | 13 nM |
| | | | | | | | | | #12 | 200 | 1 | 11 | 1 | 0 | 0 | 1 | | | |
| | | | | | | | | | #14 | 200 | 2 | 2 | 1 | 2 | 1 | 1 | | | |
| | | | | | | | | | #15 | 200 | 0 | 6 | 1 | 0 | 1 | 0 | | | |
| | | | | | | | | | #17 | 23 | 12 | 62 | 13 | -6 | 31 | -7 | | | |
| | | | | | | | | | #17 | 7 | 51 | 83 | 58 | 35 | 76 | 56 | | | |
| | | | | | | | | | #17 | 3 | 80 | 91 | 83 | 81 | 89 | 95 | | | |
| LEAI.475 | | | | | | L | | | #13 | 16 | 21 | 81 | 56 | 30 | 96 | 55 | | | |
| | | | | | | | | | #16 | 27 | 63 | 89 | 70 | 71 | 93 | 76 | | | |
| LEAI.476 | | | | | | K | | | #10 | 40 | 63 | 96 | 90 | 87 | 94 | 96 | | | |
| | | | | | | | | | #16 | 65 | 90 | 94 | 98 | 97 | 98 | 89 | | | |
| LEAI.477 | | | | | | P | | | #13 | 114 | 6 | 62 | 16 | 3 | 3 | 2 | #4 | 333 nM | 18 nM |
| LEAI.478 | | | | | | S | | | #12 | 200 | 1 | 79 | 1 | 1 | 1 | 1 | #4 | 100 nM | 12 nM |
| LEAI.479 | | | | | | W | | | #10 | 162 | 2 | 61 | 28 | 2 | 31 | 3 | #3 | 280 nM | 100 nM |
| LEAI.480 | | | | | | Y | | | #10 | 200 | 2 | 5 | 1 | 2 | 2 | 1 | #2 | 75 nM | 65 nM |
| | | | | | | | | | #12 | 200 | 1 | 2 | 1 | 1 | 1 | 1 | #3 | 43 nM | 46 nM |
| | | | | | | | | | #14 | 200 | 7 | 3 | 1 | 2 | 4 | 2 | #4 | 55 nM | 40 nM |
| | | | | | | | | | #15 | 200 | -1 | 4 | 1 | 1 | 1 | 0 | | | |
| LEAI.481 | | | | | | G | | | #10 | 75 | 15 | 84 | 25 | 1 | 4 | 2 | #3 | 220 nM | 24 nM |
| | | | | | | | | | #13 | 83 | 10 | 71 | 7 | 6 | 3 | 2 | | | |
| LEAI.482 | | | | | | H | | | #14 | 200 | 1 | 4 | 1 | 0 | 2 | 1 | #4 | 25 nM | 22 nM | a mixture of polybrene, SLPI (secretory leukocyte protease inhibitor) and target enzyme (thrombin or factor Xa) was added to give final concentrations of 50 microg/ml, 285 nM, and 10 nM, respectively. (Polybrene binds heparin, and SLPI inhibits HNE and cathepsin G.) The ATIII concentration in the complex formation reactions was 666 nM. Inhibitory complex formation was allowed to proceed for 3 minutes for the above samples and for standard curve reactions containing a range of concentrations of the undigested ATIIIs. Residual thrombin or fXa activity was determined from the initial rate of chromogenic substrate hydrolysis (S-2238 for thrombin and S-2765 for fXa). Substrate hydrolysis rates were used to obtain uncleaved, functional ATIII concentrations vs. the appropriate standard curves. The number of halflives corresponding to the functional ATIII concentration was determined from a plot of the exponential decay of 666 nM ATIII vs. elapsed number of halflives. Halflives were calculated by dividing digest times by the number of elapsed halflives. LEAI halflives were measured at 37 degrees C. as reported previously (P. Zendehrouh, Ph.D. Dissertation, Temple Univeristy School of Medicine, publically available at the Univeristy of Michigan dissertation archive in 1999.

BAL fluid was obtained from an ICU patient on the second day post ARDS onset. The lavage sample had a 91% PMN differential (0.86×10e6 neutrophils/ml), 462 microg/ml total protein, and 94 nM HNE activity (by AAPV hydrolysis). 1 microM ATIIIs were treated with BAL fluid at a 1:4 dilution from the original lavage sample, and residual anti-thrombin and anti-fXa inhibitory activities were determined as described herein. BAL half lives are very similar to values obtained with purified HNE.

Plasma-derived ATIII Kapp values for the inhibition of thrombin and factor Xa were obtained by dividing the Kapp for the alpha isoform reported in Turk et al (1997) (*Biochemistry*, 36, 6682-91) by the corresponding SI (inhibition stoichiometry) value reported in Olson et al (1992) (*J Biol Chem.* 267, 12528-38.) Progressive second order rates of thrombin and factor Xa inhibition by the recombinant ATIII variants were analyzed under pseudo first order conditions at pH 7.4 and ionic strength 0.15 in PNE-PEG buffer (20 mM phosphate buffer at pH 7.4, containing 100 nM NaCl, 0.1 M EDTA and 0.1% (w/v) polyethylene glycol 6000) at 25° C. The observed pseudo-first-order rate constants, $K_{obs}$, were calculated from the negative slope of a plot of ln (residual enzyme activity) vs. time of enzyme and inhibitor co-incubation. The second-order rate constants ($K_{app}$) were calculated from observed pseudo-first-order rate constants ($K_{obs}$) by dividing by the inhibitor concentration. Similar conditions were used for the reaction of recombinant variant ATIIIs with factor Xa and thrombin in the presence of heparin. Polybrene was added with the chromogenic substrate to quench the heparin dependent reaction. The observed pseudo-first-order rate constants were calculated for each heparin (1 nM-5 nM) concentration from the slope of the log of residual proteinase activity vs. time. This was plotted against the heparin concentration to calculate the second-order rate constant for the inhibition by the heparin-ATIII complex, ($K_{hep}$) from the equation $$K_{obs}=K_{hep}[H]_o([AT]_o/[AT]_o+K_d)+K_{uncat}[AT]_o$$

using the $K_d$ of heparin binding at ionic strength 0.15.

TABLE 9

Substrate and Inhibitor Properties of Plasma-derived ATIII and Selected ATIII Variants

| REACTION TYPE | MEASUREMENT | ENZYME | PLASMA-DERIVED ATIII | LEAI | LEAI 472 | LEAI 474 | LEAI 480 | LEAI 482 |
|---|---|---|---|---|---|---|---|---|
| Substrate | halflife, min | HNE | 2.9 | 11 | 30.1 | 38.4 | 19.9 | 25.3 |
| | ±sem | | | 0.3 | 2.8 | 4.1 | 2.8 | 3.1 |
| Substrate | halflife, min | BAL | 1.5 | Not done | 22.5 | 22.4 | 13.8 | 16.8 |
| | ±sem | | | 0.05 | 4.9 | 2.7 | 1.4 | 0.1 |
| Substrate | halflife, min | CatG | >>300 | >100 | 333 | >300 | 35.8 | >>240 |
| | ±sem | | | | | | 1.9 | |
| Inhibitor | kapp, $M^{-1}sec^{-1}$ | thrombin | 7,048 | 5,275 | 278 | 2,681 | 7,311 | 2,921 |
| | ±sem | prog | | 68 | 9 | 36 | 197 | 60 |
| Inhibitor | kapp, $M^{-1}sec^{-1}$ | thrombin | 5,882,353 | 9,360,000 | 203,450 | 2,011,733 | 2,107,967 | 5,371,900 |
| | ±sem | +hep | | (a) | (a) | 51,618 | 227,231 | 324,635 |
| Inhibitor | kapp, $M^{-1}sec^{-1}$ | factor Xa | 2,091 | 9,553 | 1,803 | 10,658 | 24,080 | 5,356 |
| | ±sem | prog | | 166 | 51 | 588 | 386 | 233 |
| Inhibitor | kapp, $M^{-1}sec^{-1}$ | factor Xa | 573,333 | 1,100,000 | 297,720 | 1,245,133 | 488,530 | 830,737 |
| | ±sem | +hep | | (a) | (a) | 47,453 | 27,107 | 121,952 |

(a) only one measurement

4. Example 4

Comparison of ATIII Produced in the DES Expression System with Plasma ATIII

In addition to carrying amino acid substituions at the P7 through P2 positions of the reactive loop, the ATIII variants whose properties were discussed in Example 2 differ from human plasma-derived ATIII with respect to expression system—dependent differences at the amino terminus of the polypeptide moiety and in the structures of N-linked oligosaccharides.

TABLE 10

|  | N terminal aa sequence | Kapp Thrombin, progressive $M^{-1}sec^{-1}$ | Kapp Thrombin, +heparin $M^{-1}sec^{-1}$ | Kapp factor Xa, progressive $M^{-1}sec^{-1}$ | Kapp factor Xa, +heparin $M^{-1}sec^{-1}$ |
|---|---|---|---|---|---|
| Plasma ATIII beta | HGSPVDI--- | 8,096 | 5,058,824 | 4,182 | 393,333 |
| DES S137A | SPVDI--- | 3,644 ± 3 | 3,800,000 | 4,928 ± 599 | 710,000 |

The similar rates for inhibition of thrombin and factor Xa in the absence and presence of heparin by DES.S137A, the parent molecule of the Example 2 ATIII variants, and the corresponding beta isoform of human plasma-derived ATIII demonstrate that the SPVDI—amino terminal sequence associated with DES expression and the different structure of N-linked oligosaccharides added by *Drosophila* cells do not account for the altered inhibition properties of the Example 2 variants. Moreover, the similar patterns of sensitivity of thrombin and factor Xa inhibtion to inactivation by human neutrophil elastase and cathepsin G (Tables 4-8) exhibited by DES.S137A and plasma-derived ATIII demonstrate that the SPVDI—amino terminal sequence associated with DES expression and the different structure of N-linked oligosaccharides added by *Drosophila* cells are not responsible for the altered protease resistance properties of the Example 2 variants.

5. Example 5

Modeling of Plasma ATIII and NR-ATIII Effects on Thrombin and Factor Xa Activities at Inflammatory Loci Due to the presence of an elastase-sensitive sequence in the functionally critical reactive loop, endogenous ATIII and infused plasma-derived ATIII supplements are sensitive to inactivation under inflammatory conditions. For elastase-sensitive antithrombins in an inflammatory milieu, eqn (1) gives the concentration of functionally active ATIII present at time t after a bolus infusion of the ATIII.

$Ct=Co*(exp(-0.6931*(t/HL.at3))$    Eqn(1):

where, t is the time post bolus infusion of ATIII in minutes, Ct is the molar concentration of active ATIII at time t, Co is the original ATIII molar concentration at t=0, and HL.at3 is the halflife of ATIII inactivation by human neutrophil elastase (HNE) in minutes.

The functional halflives of thrombin and fXa are phsiologically important factors with repect to the development of coagulopathies in sepsis and organ failure. The halflives of thrombin and fXa are inversely related to the amount of active ATIII (Ct) that is available to inhibit them, as expressed in eqns (2a,b).

$HL.IIa=0.6931/(Kapp*Ct)$    Eqn(2a):

$HL.Xa=0.6931/(Kapp*Ct)$    Eqn(2b):

where, HL.IIa=the halflife of thrombin (in seconds) at time t after the ATIII bolus, HL.Xa=the halflife of fXa (in seconds) at time t after the ATIII bolus, Kapp=the apparent second order rate constant for inhibition of thrombin or Xa by a specific AT3 molecule in the absence (progressive rate) or presence of heparin/HSPGs (heparan sulfate proteoglycans), and Ct=the molar concentration of active ATIII at time t (measured in minutes). To account for the effects of partitioning between the inhibitor and substrate pathways during ATIII reaction with thrombin and factor Xa, these calculations use Kapp, the apparent second order inhibition rate constant, rather than Kass, the second order association rate constant.

To obtain the halflives of thrombin or fXa at an inflammatory locus at time t after ATIII administration as a function of the halflife of the infused ATIII, eqn(1) is substituted into eqns (2a,b) to give eqn(3).

$HL.IIa/Xa=0.6931/(Kapp*Co*(exp(-0.6931*(t/HL.at3))))$.    Eqn (3):

The effects of administering a 250 U/kg bolus of plasma-derived ATIII or a model NR-ATIII on the half life of thrombin in the vicinity of an inflammatory locus are considered in this example. The analysis uses Co=15 uM as the initial post bolus increase in the concentration of ATIII. The plasma ATIII concentration of a 60 kg patient is theoretically raised by 15 uM immediately after infusion of a 250 U/kg dose of ATIII. Loading doses ranging from 100-250 U/kg have been utilized in a human phase III clinical trial (B L Warren, et al., 2001, JAMA, 286:1869-1878) and animal model evaluation (T E Emerson et al., 1987, Circulatory Shock, 21:1-13) of plasma-derived ATIII for the treatment of sepsis. Table 11 summarizes the properties of the human plasma-derived ATIII and four different NR-ATIII models that will be considered in example 4. The model ATIIIs have been named so that the number preceding "HL" indicates the relative halflife of the model compared to plasma-derived ATIII, and the number preceding "TH" indicates its relative rate of heparin-dependent thrombin inactivation compared to plasma-derived ATIII.

TABLE 11

Properties of NR-ATIII models, relative to plasma-derived ATIII.

| ATIII name | relative halflife of HNE inactivation | relative rate of heparin-dependent thrombin inhibition |
|---|---|---|
| plasma.at3 | 1 | 1 |
| 3HL/1TH | 3 | 1 |
| 10HL/1TH | 10 | 1 |
| 10HL/0.1TH | 10 | 0.1 |
| 10HL/0.01TH | 10 | 0.01 |

Table 12 gives the heparin-dependent thrombin inactivation rates (Kapp) for plasma ATIII and the four model ATIIIs, as well as their halflives for inactivation by neutrophil elastase. The Kapp and halflife values for plasma-derived ATIII are taken from Table 9, and the corresponding values for the model ATIIIs are derived from the plasma ATIII values according to the relationships defined in Table 11.

TABLE 12

Rates of thrombin inhibition in the presence of heparin and half lives of inactivation by neutrophil elastase for plasma-derived ATIII and NR-ATIII models.

| | Units | plasma.at3 | 3HL/1TH | 10HL/1TH | 10HL/0.1TH | 10HL/0.1TH |
|---|---|---|---|---|---|---|
| Kapp, IIa + hep | M-1sec-1 | 5,882,353 | 5,882,353 | 5,882,353 | 588,235 | 58,823 |
| HL.at3 | Min | 3 | 9 | 30 | 30 | 30 |

It is noted that the functional half lives of individual ATIII molecules (HL.at3) will vary widely, and are dependent on intrinsic and environmental factors, including, (1) the amino acid sequence of the ATIII molecule's reactive loop, (2) its proximity to an inflammatory site, (3) the concentration of oxidants and elastase inhibitors in its environment, and (4) the availability of heparin or hepamsulfate proteoglycans molecules (R E Jordan et al., 1987, Science, 237:777-779). The plasma ATIII half life value reported in Table 9 was measured in vitro using 10 nM (nanomolar) human neutrophil elastase (HNE), 1 uM ATIII, and 50 ug/ml heparin. The concentration of HNE in neutrophils is reported to exceed 5 mM (millimolar). However, the actual concentration of active elastase encountered by a given ATIII molecule will depend on its proximity to an inflammatory site, the concentration of activated neutrophils in the inflammatory site, and the local concentrations of oxidants and elastase inhibitors, including alpha1-proteinase inhibitor, SLPI, elafin. Nevertheless, it seems entirely probable that levels equal to or in excess of the 10 nM (nanomolar) HNE concentration used in this modeling example are achieved locally at inflammatory loci during sepsis, and that the active elastase at these sites cleaves and inactivates endogenous ATIII, which in turn results in the increased expression of thrombin and factor Xa. Cleaved ATIII has been observed in ARDS (acute respiratory distress syndrome) and ALI (acute lung injury) bronchoalveolar lavage samples containing elevated elastase activity (Bock et al., (2001) Amer. J. Respir. Crit. Care Med., 163, A . . . )

Equations 4-8 express the halflife of thrombin as a function of the time after bolus infusion of plasma-derived ATIII or the model NR-ATIIIs. These relationships were derived by substituting the Kapp values for heparin/HSPG-dependent inhibition of thrombin and the halflifes of the ATIIIs from Table 12 into equation 3.

$$HL.IIa = 0.6931/(5882353*0.000015*(\exp(-0.6931*(t/3))))$$ 
Eqn 4 (plasma.at3)

$$HL.IIa = 0.6931/(5882353*0.000015*(\exp(-0.6931*(t/9))))$$
Eqn 5 (3HL/1TH)

$$HL.IIa = 0.6931/(5882353*0.000015*(\exp(-0.6931*(t/30))))$$
Eqn 6 (10HL/1TH)

$$HL.IIa = 0.6931/(588235*0.000015*(\exp(-0.6931*(t/30))))$$
Eqn 7 (10HL/0.1TH)

$$HL.IIa = 0.6931/(58823*0.000015*(\exp(-0.6931*(t/30)))).$$
Eqn 8 (10HL/0.1TH)

Equations 4-8 were used to calculate thrombin halflives in the vicinity of an inflammatory locus at various times after a plasma ATIII or model ATIII bolus. Table 13 shows the halflife of thrombin in seconds at several times post bolus administration of the different ATIIIs.

TABLE 13

Thrombin half-life (seconds) at various times post bolus administration of plasma-derived and model ATIIIs.

| post bolus time (min) | plasma.at3 | 3HL/1TH | 10HL/1TH | 10HL/0.1TH | 10HL/0.01TH |
|---|---|---|---|---|---|
| 0 | 0.008 | 0.008 | 0.008 | 0.079 | 0.786 |
| 3 | 0.016 | 0.010 | 0.008 | 0.084 | 0.842 |
| 6 | 0.031 | 0.012 | 0.009 | 0.090 | 0.902 |
| 10 | 0.079 | 0.017 | 0.010 | 0.099 | 0.990 |
| 20 | 0.798 | 0.037 | 0.012 | 0.125 | 1.247 |
| 30 | 8.040 | 0.079 | 0.016 | 0.157 | 1.571 |
| 40 | 81.024 | 0.171 | 0.020 | 0.198 | 1.979 |
| 50 | 816.542 | 0.369 | 0.025 | 0.249 | 2.494 |
| 60 | 8,228.936 | 0.798 | 0.031 | 0.314 | 3.142 |

FIG. 1 is a plot of the data from Table 13 and shows thrombin halflife in the vicinity of an inflammatory locus as a function of the time post bolus infusion of plasma ATIII or the model NR-ATIIIs. The thrombin halflife is plotted on a log scale.

Immediately after injection of the plasma.at3 bolus (solid circles+solid line), the thrombin halflife is 8 milliseconds. It rapidly increases to 8 sec (a 1000-fold increase) at 30 minutes post bolus, and 8,229 seconds (a>1,000,000-fold increase) at 1 hour post bolus. Therefore, endogenous ATIII and plasma-derived ATIII are not effective for controlling thrombin generated in the vicinity of an inflammatory locus.

Immediately after infusion of 3HL/1TH (the NR-ATIII model with a 3× increased halflife to inactivation by elastase and no inhibitory defects in thrombin inactivation) (open squares+solid line), the thrombin halflife is also 8 milliseconds. However, because of the model's increased resistance to inactivation by HNE, the thrombin halflife only increases to 79 milliseconds (a 10-fold increase) at 30 minutes post bolus, and 798 milliseconds (a 100-fold increase) at 1 hour post bolus.

Even better control of thrombin can be achieved with the 10HL/1TH model (10× increased halflife and no thrombin inactivation inhibition defect) (open triangles+solid line). Immediately after infusion of 10HL/1TH, the thrombin halflife is again 8 milliseconds. However, it only increases to 16 milliseconds (a 2-fold increase) at 30 minutes post bolus, and to 31 milliseconds (a 4-fold increase) at 1 hour post bolus.

In summary, the halflife of thrombin in the vicinity of an inflammatory locus increases by the following factors at the indicated times after bolus injection of plasma or model ATIIIs. At 30 minutes post bolus, there is a 1,000× increase in thrombin halflife for plasma.at3, a 10× increase in thrombin halflife for 3HL/1TH, and a 2× increase in thrombin halflife for 10HL/1TH. At 60 minutes post bolus, there is a 1,000,000× increase in thrombin halflife for plasma.at3, a 100× increase in thrombin halflife for 3HL/1TH, and a 4× increase in thrombin halflife for 10HL/1TH.

Therefore, in the vicinity of an inflammatory locus where neutrophil elastase cleaves and inactivates the key thrombin and factor Xa inhibitor, antithrombin III, NR-ATIIIs with extended halflives and preserved inhibitory function should be beneficial as compared to endogenous antithrombin or supplementary plasma-derived ATIII due to prolonged windows of function and the ability to attenuate local expression of thrombin enzymatic activity and factor Xa—mediated thrombin generation.

Thrombin regulation in the vicinity of an inflammatory locus by model ATIIIs with (1) 10-fold increased resistance to inactivation by HNE and (2) associated 10- or 100-fold reductions in heparin cofactor dependent thrombin activity is also modeled in FIG. 1. This analysis demonstrated that inhibition defects increase the initial thrombin halflife (y-intercept), while the rate of increase in the half life of thrombin enzymatic activity as a function of time since the bolus (slope) is related to the molecule's resistance to elastase inactivation.

Thus, for the 10HL/0.1TH model (10-fold increased halflife of inactivation by elastase in combination with a 10-fold decrease in the heparin-dependent thrombin inhibition rate) (x–symbols+dashed lines), the initial thrombin halflife is 10× that observed for plasma ATIII. However, due to the increased elastase resistance of this molecule and its slower inactivation by elastase compared to plasma-derived ATIII, there is a crossover point at approximately 10 minutes after bolus administration when the thrombin neutralization by the 10HL/0.1TH model becomes better than for plasma ATIII.

For the 10HL/0.01×TH model (10-fold increased halflife of inactivation by elastase in combination with a 100-fold decrease in heparin dependent thrombin inhibition rate) (*–symbols+dashed lines), the initial thrombin halflife is 100× that observed for plasma ATIII, and the crossover point occurs at about 20 minutes post ATIII administration.

In summary, although model NR-ATIIIs with improved halflives but compromised inibitory properties eventually provide better inhibition of thrombin compared to plasma-derived ATIII, there is an initial period prior to the "crossover point" during which their performance is less efficient than that of plasma ATIII. Although the mutants with compromised inhibition but improved elastase resistance were advantageous over plasma-derived ATIII, it would be advantagous to avoid relatively higher levels of thrombin (and factor Xa) activity before the crossover point, given the cumlative effects of early thrombin generation and expression.

Disclosed herein are mutants with extended halflives and minimally compromised inhibitory properties or inhibitory properties that are superior to those of plasma-derived ATIII.

Finally, although example 5 has been presented with respect to the consequences of plasma and model NR-ATIII administration on heparin-dependent thrombin regulation at an inflammatory locus, it should be clear to one skilled in the art that the consequences of NR-ATIII infusion on progressive inhibtion of thrombin and progressive and heparin-dependent inhibition of factor Xa at inflammatory loci can be simlarly derived, and that the administration of NR-ATIIIs with increased resistance to inactivation by HNE and minimally compromised factor Xa inhibitory properties will also be advantageous with respect to controlling factor Xa activity. Moreover, given that ATIII inhibits both thrombin and factor Xa, and that one molecule of factor Xa can generate multiple thrombin molecules, NR-ATIII administration should be beneficial not only for the direct inhibition of thrombin enzymatic activity at inflammatory loci, but also for controlling the factor-Xa-mediated generation of thrombin at such sites.

6. Example 6

Comparison of the Effects of Plasma-derived ATIII and Select NR-ATIIIs on Thrombin and Factor Xa Regulation at Inflammatory Loci Several NR-ATIIIs with increased resistance to inactivation by human neutrophil elastase and favorable inhibitory properties are disclosed herein. The substrate and inhibitor properties of plasma-derived ATIII and several disclosed related mutants are compared in this Example.

Measured half lives of inactivation by HNE and constants for the inhibition of thrombin and factor Xa by plasma ATIII, LEAI, LEAI.472, LEAI.474, LEAI.480, and LEAI.482 in the absence (progressive rate) and presence of heparin are given in Table 14. This data and associated methods information was previously present as part of Table 9 in Example 3.

TABLE 14

Half lives and inhibition constants of plasma-derived ATIII and selected NR-ATIIIs.

| Measurement, Units | Enzyme/ Cofactor | Plasma.at3 | leai(bv) | leai.472 | leai.474 | leai.480 | leai.482 |
|---|---|---|---|---|---|---|---|
| halflife, min | HNE/ Heparin | 2.9 | 11 | 30.1 | 38.4 | 19.9 | 25.3 |
| kapp, $M^{-1}sec^{-1}$ | IIa/ Heparin | 5,882,353 | 9,360,000 | 203,450 | 2,011,733 | 2,107,967 | 5,371,900 |
| kapp, $M^{-1}sec^{-1}$ | IIa/ Progressive | 7,048 | 5,275 | 278 | 2,681 | 7,311 | 2,921 |
| kapp, $M^{-1}sec^{-1}$ | factor Xa/ heparin | 573,333 | 1,100,000 | 297,720 | 1,245,133 | 488,530 | 830,737 |
| kapp, $M^{-1}sec^{-1}$ | factor Xa/ progressive | 2,091 | 9,553 | 1,803 | 10,658 | 24,080 | 5,356 |

Table 15 gives the half lives and inhinition constants of plasma ATIII, LEAI, LEAI.472, LEAI.474, LEAI.480, and LEAI.482 as a percentage of plasma ATIII values.

TABLE 15

| Measurement | Enzyme/Cofactor | plasma.at3 | leai(bv) | leai.472 | leai.474 | leai.480 | Leai.482 |
|---|---|---|---|---|---|---|---|
| halflife | HNE/hep | 100% | 379% | 1038% | 1324% | 686% | 872% |
| Kapp | IIa/hep | 100% | 159% | 3% | 34% | 36% | 91% |
| Kapp | IIa/prog | 100% | 75% | 4% | 38% | 104% | 41% |
| Kapp | fXa/hep | 100% | 192% | 52% | 217% | 85% | 145% |
| Kapp | fXa/prog | 100% | 457% | 86% | 510% | 1152% | 256% |

The modeling presented in Example 5 indicated that with respect to the physiologically relevant goal of regulating thrombin and fXa activity at inflammatory sites, mutants with preserved or increased inhibitory activities in combination with increased halflives have desirable properties.

As in Example 5, $$HL.IIa/Xa = 0.6931/(Kapp*Co*(\exp(-0.6931*(t/HL.at3)))) \quad \text{Eqn. 3}$$

will be used for calculating the halflives of thrombin and factor Xa enzymatic activity at times t after bolus infusion of ATIIIs with elastase inactivation half lives of HL.at3 and apparent second order inhibtion rate constants of Kapp. The initial ATIII concentration, Co, will again be set at 15 uM (250 U/kg).

Table 16 summarizes the data and equations needed to calculate the half life of thrombin enzymatic activity at inflammatory loci with heparin/HSPGs present, following bolus administration of the indicated ATIIIs.

TABLE 16

Data and equations for calculation of thrombin half life at inflammatory sites in the presence of heparin/HSPGs.

| | | plasma at3 | leai(bv) | leai.472 | leai.474 | leai.480 | leai.482 |
|---|---|---|---|---|---|---|---|
| halflife, min | HNE/hep | 2.9 | 11 | 30.1 | 38.4 | 19.9 | 25.3 |
| kapp, M$^{-1}$sec$^{-1}$ | IIa/hep | 5,882,353 | 9,360,000 | 203,450 | 2,011,733 | 2,107,967 | 5,371,900 |
| | | eqn 9 | eqn 10 | eqn 11 | eqn 12 | eqn 13 | Eqn 14 |

Eqn 9
HL.IIa = 0.6931/(5,882,353 * .000015 * (exp(−.6931 * (t/2.9))))
Eqn 10
HL.IIa = 0.6931/(9,360,000 * .000015 * (exp(−.6931 * (t/11))))
Eqn 11
HL.IIa = 0.6931/(203,450 * .000015 * (exp(−.6931 * (t/30.1))))
Eqn 12
HL.IIa = 0.6931/(2,011,733 * .000015 * (exp(−.6931 * (t/38.4))))
Eqn 13
HL.IIa = 0.6931/(2,107,967 * .000015 * (exp(−.6931 * (t/19.9))))
Eqn 14
HL.IIa = 0.6931/(5,371,900 * .000015 * (exp(−.6931 * (t/25.3))))

Table 17 illustrates time-dependent effects of bolus plasma-derived ATIII or selected NR-ATIII administration on the half life of enzymatically active thrombin at inflammatory sites with heparin/HSPGs present. The numbers in Table 17 were generated using the data and equations from Table 16.

TABLE 17

Halflife (seconds) of thrombin enzymatic activity at inflammatory sites with heparin/HSPGs present at various times post bolus administration of plasma-derived ATIII or indicated NR-ATIII variants.

| min post bolus | pl.ATIII | LEAI | 472 | 474 | 480 | 482 |
|---|---|---|---|---|---|---|
| 0 | 0.008 | 0.005 | 0.227 | 0.023 | 0.022 | 0.009 |
| 3 | 0.016 | 0.006 | 0.243 | 0.024 | 0.024 | 0.009 |
| 6 | 0.033 | 0.007 | 0.261 | 0.026 | 0.027 | 0.010 |
| 9 | 0.068 | 0.009 | 0.279 | 0.027 | 0.030 | 0.011 |
| 20 | 0.936 | 0.017 | 0.360 | 0.033 | 0.044 | 0.015 |
| 30 | 10.210 | 0.033 | 0.453 | 0.039 | 0.062 | 0.020 |
| 60 | 13,272.002 | 0.216 | 0.904 | 0.068 | 0.177 | 0.045 |

Figure 2A:
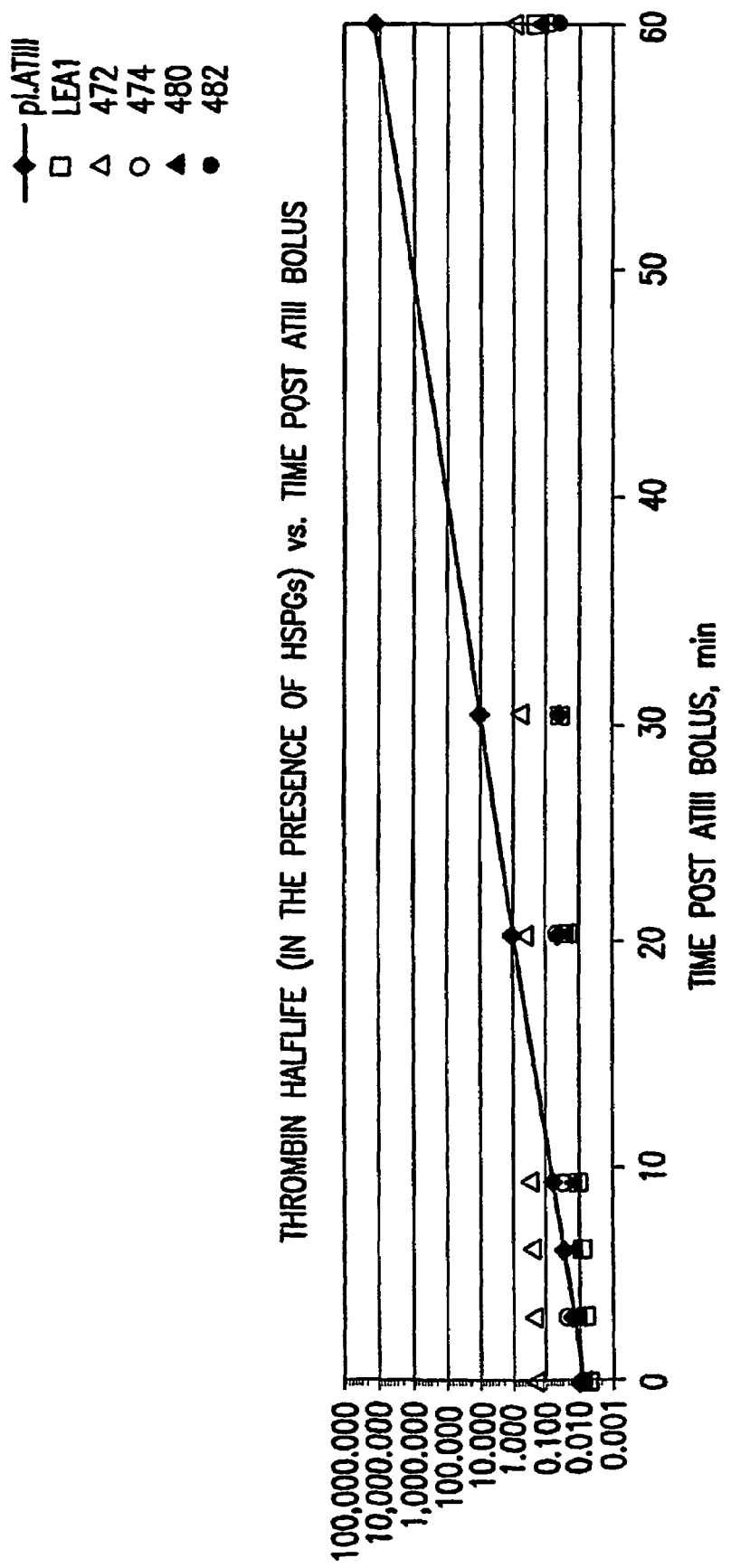
FIG. 2A and FIG. 2B show the thrombin halflife in the presence of HSPGs vs time post ATIII bolus.
Figure 2B:
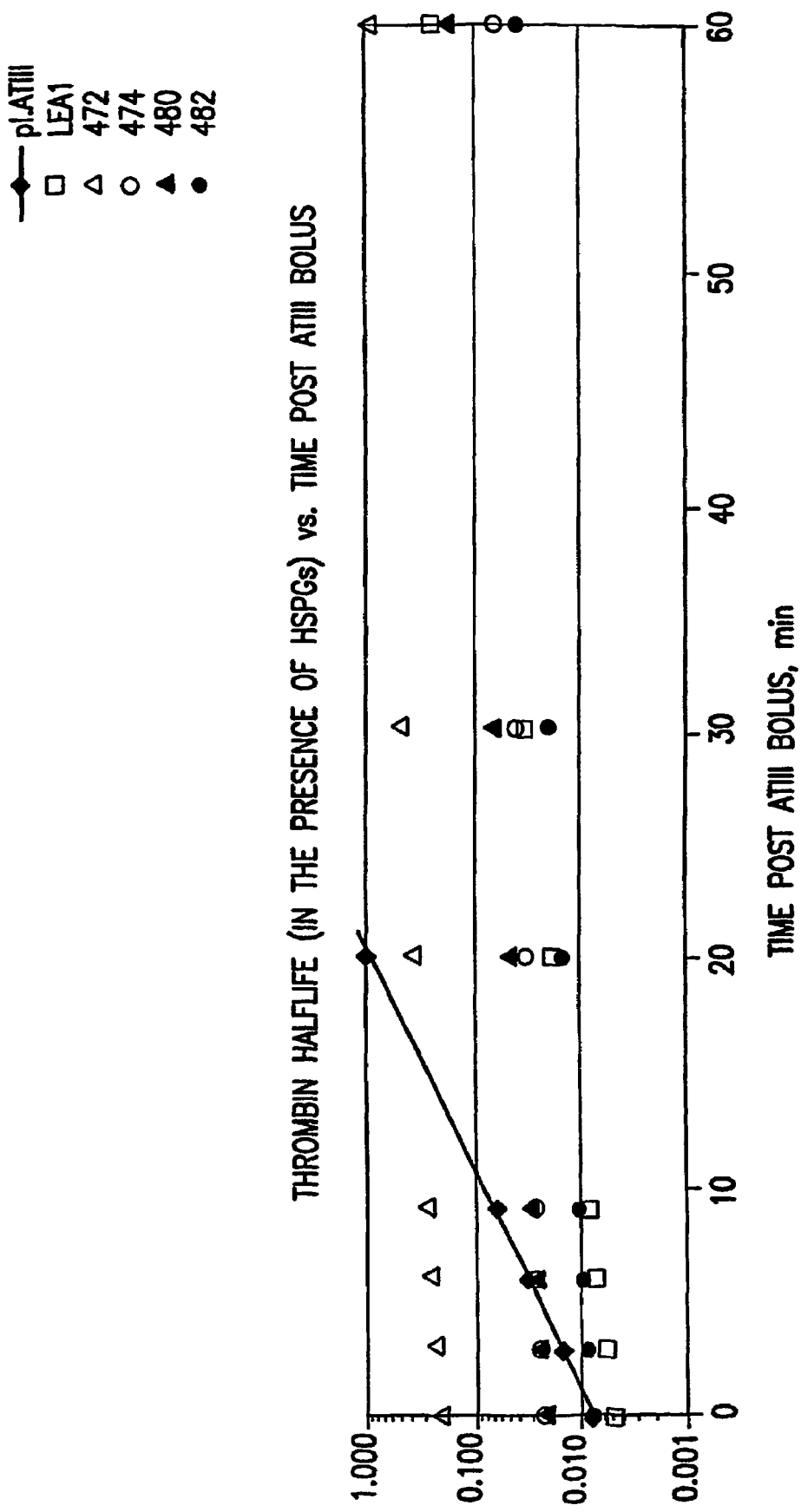

FIGS. 2A and 2B shows graphs of the results presented in Table 17. FIGS. 2A and 2B indicate that with respect to HSPG-mediated control of thrombin at an inflammatory locus, LEAI.482 and LEAI function well as they function better than plasma ATIII at all time points. At 1 hour post administration, thrombin halflife has increased from 8 milliseconds to 45 milliseconds for the LEAI.482 mutant, and to 216 milliseconds for LEAI. This is in contrast to the case of plasma-derived ATIII where at 1 hour post infusion, thrombin is essentially uninibited at inflammatory loci (half life of 13,272 sec=3.7 hours).

It should also be noted that due to their decreased rates of heparin-mediated thrombin inhibtion, the 472, 474 and 480 mutants reguate thrombin less well than does plasma-derived ATIII during a 5-15 minute period immediately following ATIII administration but these mutants still are desirable relative to plasma ATIII in the long run.

Table 18 summarizes the data and equations needed to calculate the half life of thrombin enzymatic activity at inflammatory loci under progressive conditions, following bolus administration of the indicated ATIIIs.

TABLE 18

Data and equations for calculation of thrombin half life at inflammatory sites under progressive conditions.

|  |  | plasma at3 | leai(bv) | leai.472 | leai.474 | leai.480 | leai.482 |
|---|---|---|---|---|---|---|---|
| halflife, min | HNE/hep | 2.9 | 11 | 30.1 | 38.4 | 19.9 | 25.3 |
| kapp, $M^{-1}sec^{-1}$ | IIa/prog | 7,048 | 5,275 | 278 | 2,681 | 7,311 | 2,921 |
|  |  | eqn 15 | eqn 16 | eqn 17 | eqn 18 | eqn 19 | Eqn 20 |

Eqn 15
$HL.IIa = 0.6931/(7048 * .000015 * (exp(-.6931 * (t/2.9))))$
Eqn 16
$HL.IIa = 0.6931/(5275 * .000015 * (exp(-.6931 * (t/11))))$
Eqn 17
$HL.IIa = 0.6931/(278 * .000015 * (exp(-.6931 * (t/30.1))))$
Eqn 18
$HL.IIa = 0.6931/(2681 * .000015 * (exp(-.6931 * (t/384))))$
Eqn 19
$HL.IIa = 0.6931/(7311 * .000015 * (exp(-.6931 * (t/19.9))))$
Eqn 20
$HL.IIa = 0.6931/(2921 * .000015 * (exp(-.6931 * (t/25.3))))$ Table 19 illustrates time-dependent effects of bolus plasma-derived ATIII or selected NR-ATIII administration on the half life of enzymatically active thrombin at inflammatory sites under progressive conditions where heparin/HSPGs are not present in the reaction situation. The numbers in Table 19 were generated using the data and equations from Table 18.

TABLE 19

Halflife (seconds) of thrombin enzymatic activity at inflammatory sites (progressive conditions) at various times post bolus administration of plasma-derived ATIII or indicated NR-ATIII variants.

| min post bolus | pl.ATIII | LEAI | 472 | 474 | 480 | 482 |
|---|---|---|---|---|---|---|
| 0 | 7 | 9 | 166 | 17 | 6 | 16 |
| 3 | 13 | 11 | 178 | 18 | 7 | 17 |
| 6 | 28 | 13 | 191 | 19 | 8 | 19 |
| 9 | 56 | 15 | 204 | 20 | 9 | 20 |
| 20 | 781 | 31 | 263 | 25 | 13 | 27 |
| 30 | 8,522 | 58 | 332 | 30 | 18 | 36 |
| 60 | 11,076,986 | 384 | 662 | 51 | 51 | 82 |

Figure 3A:
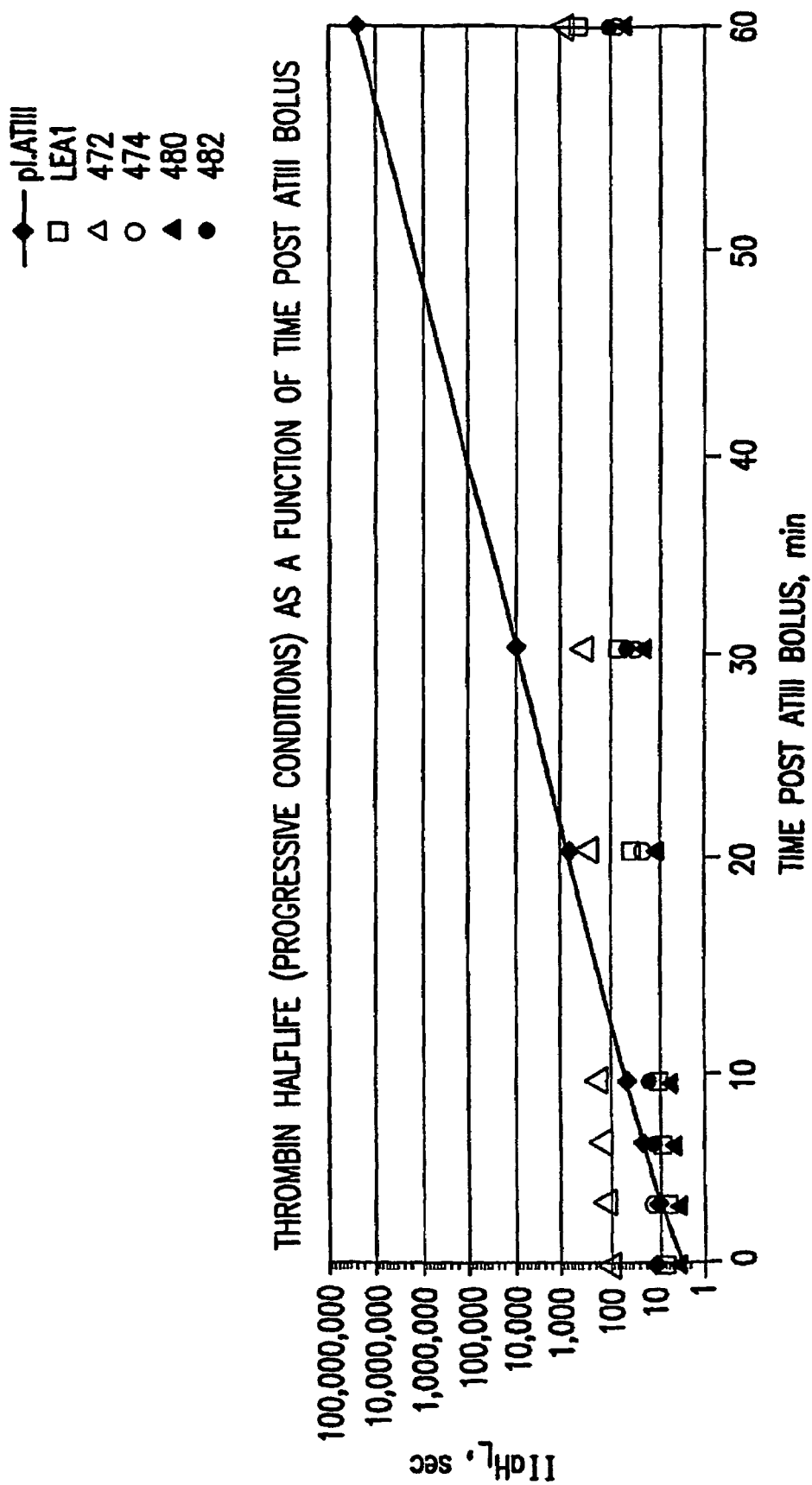
FIG. 3A and FIG. 3B show the thrombin halflife under progressive conditions as a function of time post ATIII bolus.
Figure 3B:
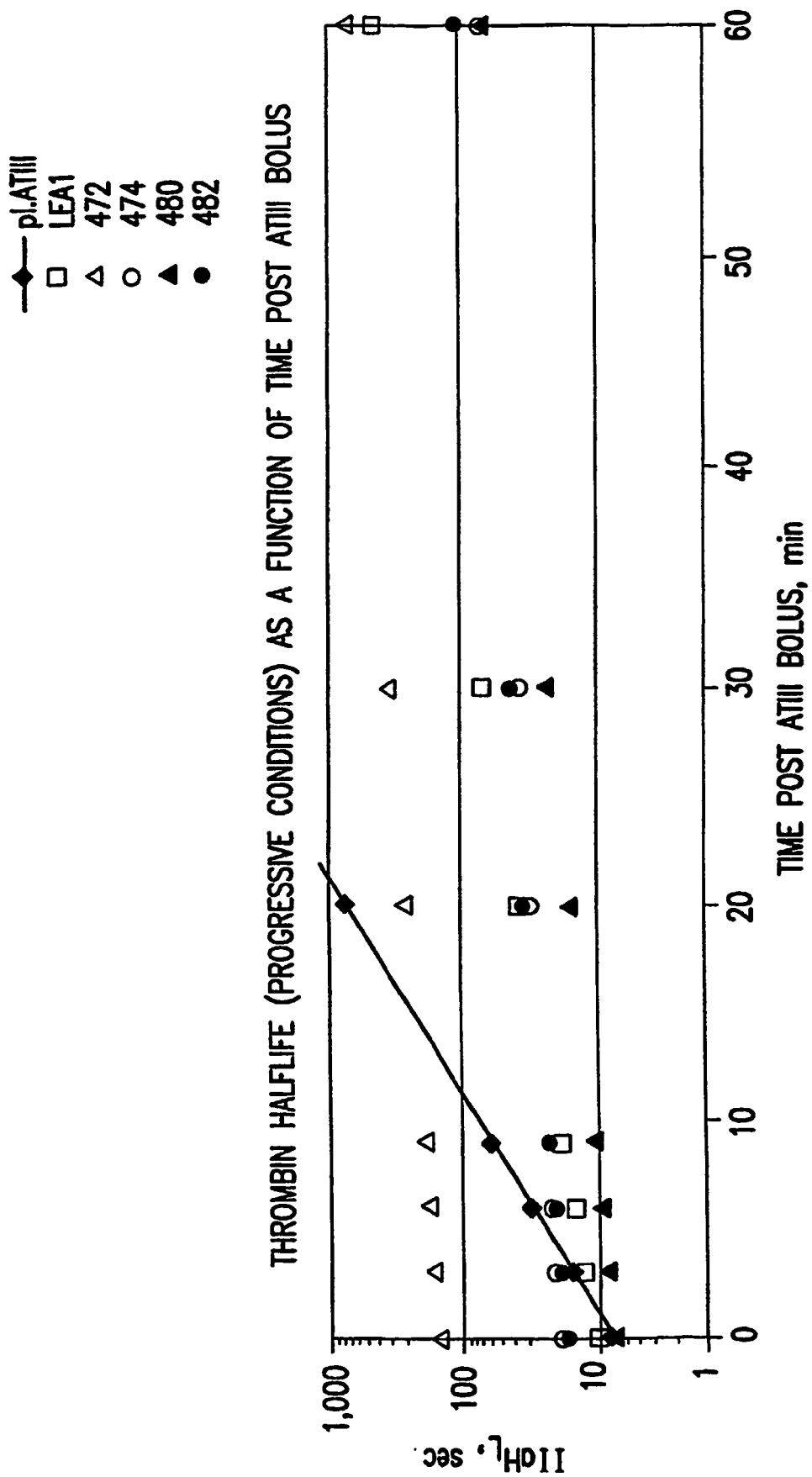

FIGS. 3A and 3B are plots of the data in Table 19. FIGS. 3A and 3B show that with respect to progressive thrombin inhibition in an inflammatory locus, the leai.480 mutant performs better than plasma-derived ATIII at all times. Except for during the first 2-5 minutes after administration, LEAI, leai.474 and leai.482 also inhibit thrombin more effectively than does plasma-derived ATIII. Even leai.472 performs better than plasma ATIII after about 15 minutes. At 1 hour post ATIII administration, the thrombin halflife with NR-ATIII mutants is 4-5 orders of magnitude shorter than it would be with plasma-derived ATIII.

Table 20 summarizes the data and equations needed to calculate the half life of factor Xa enzymatic activity at inflammatory loci where heparin/HSPGs are present, following bolus administration of the indicated ATIIIs.

TABLE 20

Data and equations for calculation of factor Xa halflife at inflammatory sites in the presence of heparin/HSPGs.

|  |  | Plasma at3 | leai(bv) | leai.472 | leai.474 | leai.480 | leai.482 |
|---|---|---|---|---|---|---|---|
| halflife, min | HNE | 2.9 | 11 | 30.1 | 38.4 | 19.9 | 25.3 |
| kapp, | fXa/hep | 573,333 | 1,100,000 | 297,720 | 1,245,133 | 488,530 | 830,737 |

TABLE 20-continued

Data and equations for calculation of factor Xa halflife at inflammatory sites in the presence of heparin/HSPGs.

| $M^{-1}sec^{-1}$ | Plasma at3 | leai(bv) | leai.472 | leai.474 | leai.480 | leai.482 |
|---|---|---|---|---|---|---|
| | eqn 21 | eqn 22 | eqn 23 | eqn 24 | eqn 25 | Eqn 26 |

Eqn 21
HL.Xa = 0.6931/(573333 * .000015 * (exp(−.6931 * (t/2.9))))
Eqn 22
HL.Xa = 0.6931/(1100000 * .000015 * (exp(−.6931 * (t/11))))
Eqn 23
HL.Xa = 0.6931/(297720 * .000015 * (exp(−.6931 * (t/30.1))))
Eqn 24
HL.Xa = 0.6931/(1245133 * .000015 * (exp(−.6931 * (t/38.4))))
Eqn 25
HL.Xa = 0.6931/(488530 * .000015 * (exp(−.6931 * (t/19.9))))
Eqn 26
HL.Xa = 0.6931/(830737 * .000015 * (exp(−.6931 * (t/25.3))))

Table 21 illustrates time-dependent effects of bolus plasma-derived ATIII or selected NR-ATIII administration on the half life of enzymatically active factor Xa at inflammatory sites with heparin/HSPGs present. The numbers in Table 21 were generated using the data and equations from Table 20.

TABLE 21

Halflife (seconds) of factor Xa enzymatic activity at inflammatory sites with heparin/HSPGs present at various times post bolus administration of plasma-derived ATIII or indicated NR-ATIII variants.

| min post bolus | pl.ATIII | LEAI | 472 | 474 | 480 | 482 |
|---|---|---|---|---|---|---|
| 0 | 0.081 | 0.042 | 0.155 | 0.037 | 0.095 | 0.056 |
| 3 | 0.165 | 0.051 | 0.166 | 0.039 | 0.105 | 0.060 |
| 6 | 0.338 | 0.061 | 0.178 | 0.041 | 0.117 | 0.066 |
| 9 | 0.693 | 0.074 | 0.191 | 0.044 | 0.129 | 0.071 |
| 20 | 9.599 | 0.148 | 0.246 | 0.053 | 0.190 | 0.096 |
| 30 | 104.758 | 0.278 | 0.310 | 0.064 | 0.269 | 0.127 |
| 60 | 136,169.728 | 1.842 | 0.618 | 0.110 | 0.765 | 0.288 |

Figure 4A:
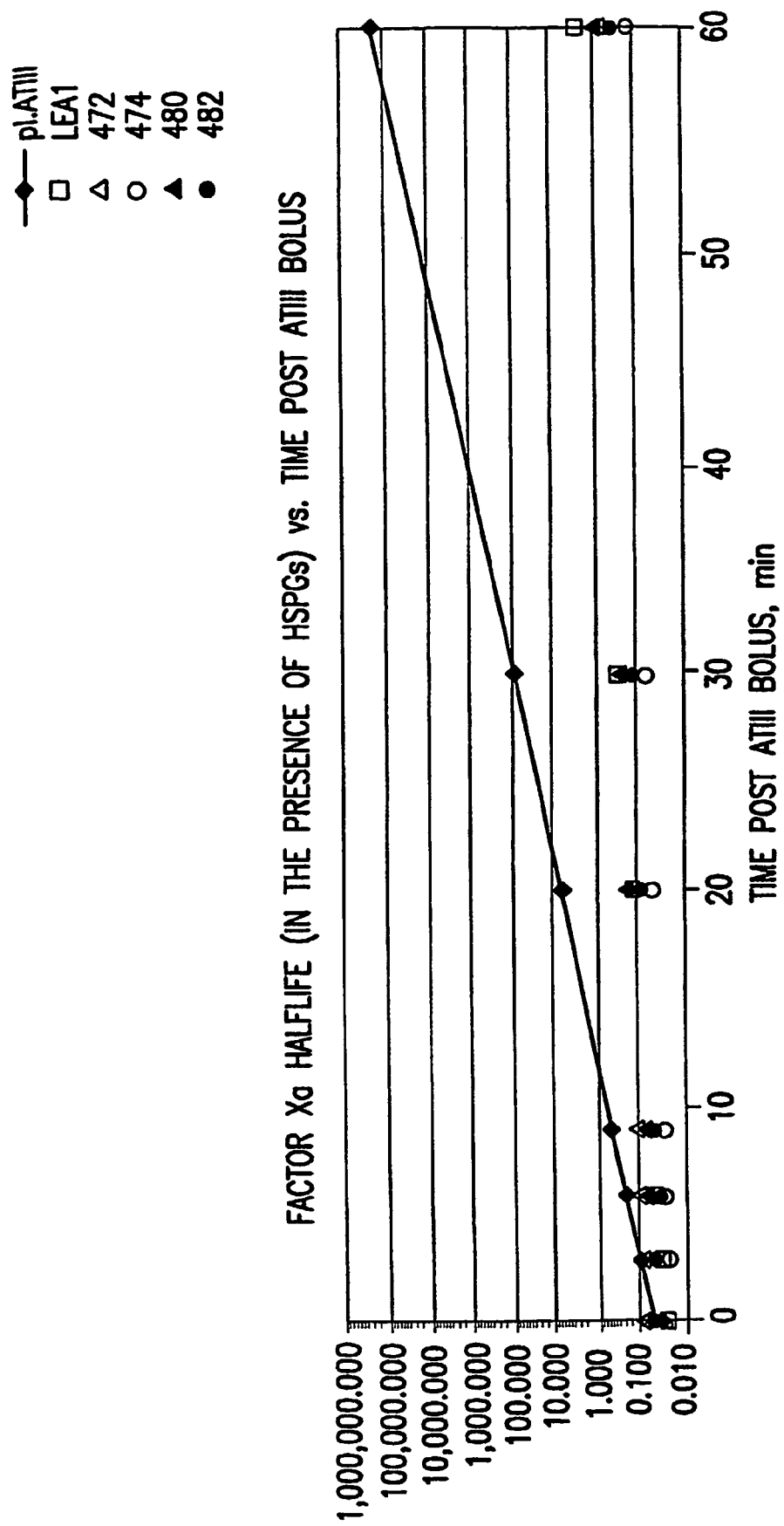
FIG. 4A and FIG. 4B show the fXa halflife under HSPG conditions as a function of time post ATIII bolus.
Figure 4B:
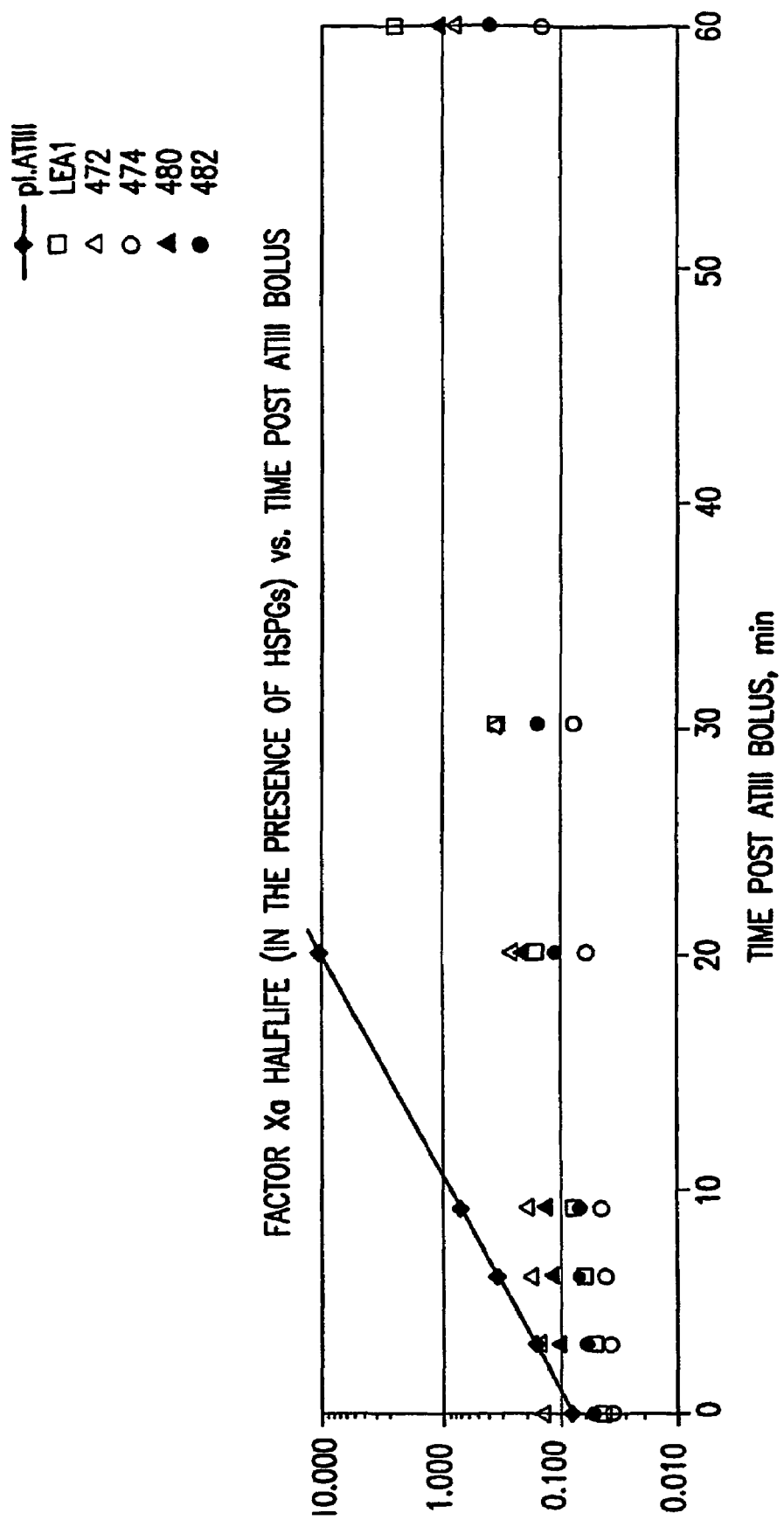

FIGS. 4A and 4B are plots of the data in Table 21. FIGS. 4A and 4B show that with the exception of LEAI.472, the mutants regulated thrombin better than plasma ATIII at all times. LEAI.474 and LEAI.482 provided the most effective fXa control for extended periods of time. At one hour after administration of the mutants, calculated factor Xa halflives were in the range of 0.1-1.82 seconds as compared to 136,170 seconds (37.8 hours) for plasma-derived ATIII.

Table 22 summarizes the data and equations needed to calculate the half life of factor Xa enzymatic activity at inflammatory loci under progressive conditions, following bolus administration of plasma ATIII or selected NR ATIIIs. For each column of data the equation related to the data is denoted.

TABLE 22

Data and equations for calculation of factor Xa halflife at inflammatory sites under progressive conditions.

| | | plasma at3 | leai(bv) | leai.472 | leai.474 | leai.480 | Leai.482 |
|---|---|---|---|---|---|---|---|
| halflife, min | HNE | 2.9 | 11 | 30.1 | 38.4 | 19.9 | 25.3 |
| kapp, $M^{-1}sec^{-1}$ | fXa/prog | 2,091 | 9,553 | 1,803 | 10,658 | 24,080 | 5,356 |
| | | eqn 27 | eqn 28 | eqn 29 | eqn 30 | eqn 31 | Eqn 32 |

Eqn 27
HL.Xa = 0.6931/(2091 * .000015 * (exp(−.6931 * (t/2.9))))
Eqn 28
HL.Xa = 0.6931/(9553 * .000015 * (exp(−.6931 * (t/11))))
Eqn 29
HL.Xa = 0.6931/(1803 * .000015 * (exp(−.6931 * (t/30.1))))
Eqn 30
HL.Xa = 0.6931/(10658 * .000015 * (exp(−.6931 * (t/38.4))))
Eqn 31
HL.Xa = 0.6931/(24080 * .000015 * (exp(−.6931 * (t/19.9))))
Eqn 32
HL.Xa = 0.6931/(5356 * .000015 * (exp(−.6931 * (t/25.3))))

Table 23 illustrates time-dependent effects of bolus plasma-derived ATIII or selected NR-ATIII administration on the half life of enzymatically active factor Xa at inflammatory sites under progressive conditions. The numbers in Table 23 were generated using the data and equations from Table 22.

TABLE 23

Halflife (seconds) of factor Xa enzymatic activity at inflammatory sites under progressive conditions at various times post bolus administration of plasma-derived ATIII or indicated NR-ATIII variants

| min post bolus | pl.ATIII | LEAI | 472 | 474 | 480 | 482 |
|---|---|---|---|---|---|---|
| 0 | 22 | 5 | 26 | 4 | 2 | 9 |
| 3 | 45 | 6 | 27 | 5 | 2 | 9 |
| 6 | 93 | 7 | 29 | 5 | 2 | 10 |
| 9 | 190 | 9 | 32 | 5 | 3 | 11 |
| 20 | 2,632 | 17 | 41 | 6 | 4 | 15 |
| 30 | 28,724 | 32 | 51 | 7 | 5 | 20 |
| 60 | 37,336,489 | 212 | 102 | 13 | 16 | 45 |

Figure 5B:
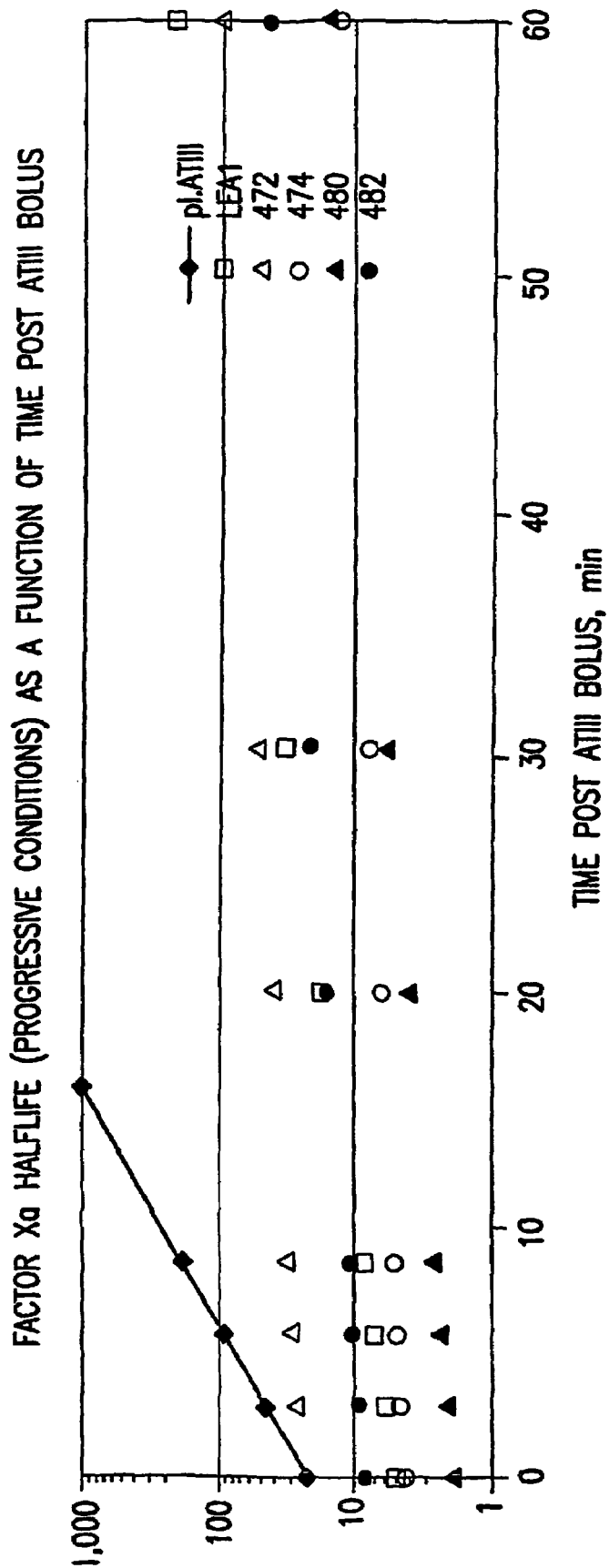

FIGS. 5A and 5B are plots of the data shown in Table 23. FIGS. 5A and 5B show that in the absence of heparin/HSPGs, all mutants provided better control of fXa compared to plasma-derived ATIII. At 1 hour post ATE, fXa halflives were in the range of 13-213 milliseconds for the NR-ATIII mutants, versus 37,336,489 seconds (10,371 hours) for plasma-derived ATIII.

7. Example 7

Additional P5 and P7 Mutants—Effects of P5 and P7 Residues on the Inhibition, Substrate and Heparin Activation Properties of Antithrombin III The effects of P5 and P7 substitutions on the substrate, inhibitor and heparin activation properties of neutrophil-resistant antithrombins (NR-ATIIIs) were investigated by generating additional mutants. The parent molecule for these mutants was LEAI.474, which has the P6-P3 sequence LEAQ, and possesses the favorable inhibitor, substrate and activation characteristics needed to maintain anticoagulant function under acute inflammatory conditions. As detailed in Table 24, LEAQ.501-509 carry different amino acid substitutions at the P5 position of LEAI.474. LEAQ.514-521 and LEAQ.523 represent several different substitutions at the P7 alanine of LEAI.474. Finally, 13C.511 is 13C432 in which the P7 glutamic acid is replaced with alanine. Procedures for mutagenesis, mutant protein synthesis in the DES (*Drosophila* expression) system, and antithrombin III purification were performed as described herein. Methods for semi-quantitative screening of antithrombin variant substrate, inhibition and heparin activation properties and the measurement of thrombin inhibition rates in the absence and presence of heparin were also performed as described herein. Table 24 summarizes human neutrophil elastase and cathepsin G substrate, human thrombin and factor Xa inhibitor and unfractionated heparin activation screening data obtained for these 16 antithrombin mutants. Table 25 presents thrombin inhibition rates of selected mutants in the absence and presence of heparin.

TABLE 24

Inhibitor, substrate, and activation properties of LEAQ 501-521

| | P7 | P6 | P5 | P4 | P3 | P2 | P1 | CA expt | stg 1 conc | rsd IIa, no add | rsd IIa, HNE | rsd IIa, catG | rsd Xa, no add | rsd Xa, HNE | rsd Xa, catG | HCA expt | IC50 IIa/UFH, nM | IC50 fXa/UFH, nM |
|---|---|---|---|---|---|---|---|---|---|---|---|---|---|---|---|---|---|---|
| plasma.ATIII | A | V | V | I | A | G | R | #14 | 200 | 5 | 100 | 1 | 2 | 101 | 2 | #4 | 15 | 13 |
| ATIII.S137A | A | V | V | I | A | G | R | #13 | 200 | 4 | 89 | 1 | 2 | 87 | 1 | #6a | 12 | 17 |
| | | | | | | | | #51 | 200 | 1 | 97 | 1 | 1 | 63 | −1 | #6b | 7 | 13 |
| | | | | | | | | #52 | 200 | 1 | 77 | 5 | 3 | 134 | 3 | #4 | 13 | 12 |
| | | | | | | | | #52 | 57 | 1 | 90 | 3 | 3 | 126 | 2 | #5 | 9 | 10 |
| | | | | | | | | #52 | 34 | 1 | 93 | 4 | 3 | 121 | 2 | | | |
| LEAI.474 | A | L | E | A | Q | G | R | #51 | 200 | 2 | 2 | 2 | −1 | −3 | −2 | #2 | 65 | 20 |
| | | | | | | | | #52 | 200 | 4 | 3 | 3 | 2 | 3 | 1 | #3 | 47 | 16 |
| | | | | | | | | | | | | | | | | #4 | 50 | 13 |
| | | | | | | | | | | | | | | | | #5 | 65 | 23 |
| | | | | | | | | | | | | | | | | #6 | 55 | 33 |
| LEAQ.501 | A | L | D | A | Q | G | R | #51 | 200 | 2 | 3 | 3 | 1 | 1 | −2 | #6 | 140 | 19 |
| | | | | | | | | | | | | | | | | #5 | 150 | 15 |
| LEAQ.502 | A | L | S | A | Q | G | R | #51 | 200 | 1 | 1 | 2 | 1 | 1 | −1 | #6 | 18 | 19 |
| | | | | | | | | | | | | | | | | #5 | 16 | 12 |
| LEAQ.503 | A | L | T | A | Q | G | R | #51 | 200 | 0 | 1 | 1 | 1 | 0 | −2 | #5 | 13 | 11 |
| LEAQ.504 | A | L | N | A | Q | G | R | #51 | 200 | 1 | 1 | 1 | 0 | 1 | −1 | #5 | 17 | 14 |
| LEAQ.505 | A | L | Q | A | Q | G | R | #51 | 200 | 0 | 0 | 0 | 1 | 1 | −2 | #5 | 18 | 16 |
| LEAQ.506 | A | L | H | A | Q | G | R | #51 | 180 | 1 | 2 | 1 | −1 | −3 | −1 | #5 | 9 | 13 |
| LEAQ.507 | A | L | R | A | Q | G | R | #51 | 200 | 1 | 2 | 2 | −2 | −3 | −2 | #5 | 55 | 55 |
| LEAQ.508 | A | L | K | A | Q | G | R | #51 | 200 | 1 | 1 | 1 | −1 | −3 | −2 | #5 | 18 | 19 |
| LEAQ.509 | A | L | V | A | Q | G | R | #51 | 200 | 1 | 1 | 0 | −1 | −3 | −1 | #5 | 16 | 16 |
| | | | | | | | | #52 | 200 | 1 | 52 | 6 | 3 | 10 | 1 | #6 | 18 | 20 |
| LEAQ.514 | V | L | E | A | Q | G | R | #52 | 34 | 10 | 91 | 14 | 4 | 106 | 3 | #6 | 105 | 40 |
| LEAQ.515 | L | L | E | A | Q | G | R | #52 | 200 | 5 | 3 | 3 | 2 | 2 | 1 | #6 | 110 | 18 |
| LEAQ.516 | F | L | E | A | Q | G | R | #52 | 200 | 4 | 9 | 5 | 3 | 3 | 1 | #6 | 120 | 25 |
| LEAQ.517 | S | L | E | A | Q | G | R | #52 | 200 | 4 | 3 | 2 | 2 | 2 | 1 | #6 | 65 | 27 |
| LEAQ.518 | T | L | E | A | Q | G | R | #52 | 200 | 4 | 3 | 2 | 3 | 2 | 1 | #6 | 50 | 27 |
| LEAQ.521 | H | L | E | A | Q | G | R | #52 | 57 | 6 | 20 | 4 | 2 | 3 | 1 | #6 | 100 | 25 |
| 13C.432 | E | L | E | I | A | G | R | #7 | 200 | 5 | 3 | 5 | 4 | 7 | 3 | #2 | 460 | 45 |
| | | | | | | | | #8 | 200 | 5 | 16 | 8 | 1 | 1 | 1 | | | |

TABLE 24-continued Inhibitor, substrate, and activation properties of LEAQ 501-521

| 13C.511 | A | L | E | I | A | G | R | #51 | 200 | 2 | 54 | 1 | −1 | −3 | −2 | #6 | 130 | 40 |
|---|---|---|---|---|---|---|---|---|---|---|---|---|---|---|---|---|---|---|
|  |  |  |  |  |  |  |  | #52 | 200 | 5 | 84 | 5 | 2 | 92 | 1 | #5 | 150 | 30 | rsd IIa, residual thrombin activity
rsd Xa, residual factor Xa activity
UFH, unfractionated heparin
CA, coupled assay
HCA, heparin cofactor assay

|  | $K_{app}$, thrombin progressive | $K_{app}$, thrombin HAH |
|---|---|---|
| plasma.ATIII | $7.0 \times 10^3$ | $5.9 \times 10^6$ |
| DES.S137A | $3.6 \times 10^3$ | $3.8 \times 10^6$ |
| DES.LEAI.474 | $2.7 \pm 0.0 \times 10^3$ | $2.0 \times 10^6$ |
| DES.LEAQ.502 | $3.0 \pm 0.2 \times 10^3$ | $1.1 \times 10^7$ |
| DES.LEAQ.503 | $3.7 \pm 0.1 \times 10^3$ | $1.6 \times 10^7$ |
| DES.LEAQ.504 | $3.3 \pm 0.1 \times 10^3$ | $6.1 \times 10^6$ |
| DES.LEAQ.506 | $4.1 \pm 0.1 \times 10^3$ | $1.1 \times 10^7$ |
| DES.LEAQ.508 | $4.1 \pm 0.1 \times 10^3$ | $1.1 \times 10^7$ |

Table Yyy. Thrombin inhibition in the absence and presence of heparin

Data included in Table 24 indicate that under screening assay conditions, the LEAI.474 base molecule for these studies inhibits thrombin and factor Xa in the absence of heparin as effectively as does its own S137A parent molecule (carrying a wild type reactive loop sequence) and plasma-derived antithrombin. However, in contrast to antithrombins with wild type reactive loop sequences, LEAI.474 is fully resistant to inactivation by neutrophil elastase. LEAI.474 also retains the cathepsin G resistance of antithrombins with normal reactive loop sequences. Its rates of thrombin and factor Xa inhibition are accelerated by heparin, although to a slightly lesser extent than observed for its recombinant S137A parent and for plasma-derived ATIII. The IC50s for LEAI.474 inhibition of thrombin and factor Xa in the presence of heparin are typically 4-5 times higher than those of its S137A parent and plasma-derived antithrombin.

The P5 glutamic acid residue of LEAI.474 was replaced with a charged residue (LEAQ.501, 507 and 508), a polar residue (LEAQ.502-505), a histidine (LEAQ.506) or a valine (LEAQ.509). With the exception of LEAQ.509, all of these mutants maintain similar high levels of elastase-resistance observed for their LEAI.474 parent, and the cathepsin G resistance of plasma-derived antithrombin. LEAQ.509, which contains a P5 valine residue, appears to be somewhat less elastase resistant than its 474 parent and the other P5 derivatives. This observation is consistent with the P1 preference of neutrophil elastase for medium sized hydrophobic amino acids. In the presence of heparin, several of the P5 mutants (LEAQ.502-506 and LEAQ.508-509) inhibit thrombin more effectively than plasma ATIII or their LEAI.474 parent molecule (see lower IC50s in Table 24 and higher Kapps in Table 25). Several of the P5 mutants (LEAQ.502-506 and LEAQ.508-509) have IC50s for heparin catalyzed inhibition of thrombin that are lower than that of their LEAI.474 parent and that approximate the IC50 for plasma-derived ATIII. The P5 substitutions which lead to improved heparin activation of thrombin inhibition include serine, threonine, aspargine, glutamine, histidine, lysine and valine replacements. In contrast, LEA.474 (P5 glutamic acid) and LEAQ.501 (P5 aspartic acid) have higher IC50s for heparin catalyzed inhibition of thrombin. These results suggest that the P5 residue of the reactive loop may interact with heparin during activation of antithrombin, and that repulsive interactions between a negatively charged P5 amino acid and heparin may adversely affect the rate of activation. Based on the minimal variation in IC50 data for LEAQ.501-509 inhibition of factor Xa in the presence of heparin, the P5 residue does not play an important role in heparin mediated activation of factor Xa inhibition. This is consistent with known differences between the mechanisms for heparin activation of thrombin and factor Xa inhibition by antithrombin, in which the activation of factor Xa inhibition is largely mediated by the pentasaccharide sequence on heparin.

LEAQ.514-521 are variants of LEAI.474 in which the wild type P7 alanine is replaced with a larger hydrophobic residue or a polar amino acid. With the exception of LEAQ.514 and LEAQ.521, these mutants retain a level of elastase-resistance similar to their LEAI.474 parent, and the cathepsin G resistance of plasma-derived antithrombin. The P7 histidine substitution in LEAQ.521 slightly increases its elastase sensitivity relative to its 474 parent molecule, however, 521 nevertheless exhibits significantly greater elastase resistance than plasma-derived ATIII. The P7 valine substitution in LEAQ.514 confers susceptibility to elastase inactivation and reverted this variant to a form exhibiting elastase sensitivity comparable to plasma-derived ATIII. Again, the increased elastase sensitivity observed following the introduction of a valine residue in the reactive loop is consistent with the substrate specificity of neutrophil elastase, and suggests that the P7 residue is accessible. Further characterization of the LEAQ.514-521 derivatives of LEAI.474 also demonstrate that the P7 residue influences heparin activation of thrombin inhibition. Variants in which the small wild type P7 alanine residue was substituted by the small polar residues serine and threonine (LEAQ.417 and 418) had IC50s for heparin-dependent thrombin inhibition that were comparable to their LEAI.474 parent. However, the corresponding valine, leucine, phenylalaine, and histidine P7 substitution mutant IC50s for heparin-dependent thrombin inhibition were greater than those of the parent molecule. Variant 13C.511, a derivative of 13C.432 carrying a P7 alanine for glutamic acid substitution, also exhibited a decrease in the IC50 for heparin-dependent thrombin inhibition. Together the data suggest that the size of the P7 residue, and not its polarity, plays a role in the mechanism for heparin activation of thrombin inhibition.

In summary, a range of different amino acids at the P5 and P7 positions of the antithrombin III reactive center loop are compatible with resistance to cleavage by neutrophil elastase, but valine substitutions at these positions increase elastase sensitivity. The P5 and P7 residues also influence heparin activation of thrombin inhibition, with non-acidic residues in the P5 position and small residues in the P7 position leading to better activation. Data in Table 24 and 25 suggest that due to improved anti-thrombin heparin cofactor activity on a background of favorable inhibitor and substrate characteristics, LEAQ.502, 503, 504, 505, 506 and 508 can function very effectively under pathological inflammatory conditions.

G. Sequences
1. SEQ ID NO:1 Bb
2. SEQ ID NO:2 Bb.401
3. SEQ ID NO:3 Bb.402
4. SEQ ID NO:4 Bb.403
5. SEQ ID NO:5 Bb.404
6. SEQ ID NO:6 Bb.405
7. SEQ ID NO:7 Bb.406
8. SEQ ID NO:8 Bb.A
9. SEQ ID NO:9 Bb.A.411
10. SEQ ID NO:10 Bb.A.412
11. SEQ ID NO:11 Bb.A.413
12. SEQ ID NO:12 Bb.A.414
13. SEQ ID NO:13 Bb.A.415
14. SEQ ID NO:14 Bb.A.416
15. SEQ ID NO:15 Bb.A.417
16. SEQ ID NO:16 Bb.A.418
17. SEQ ID NO:17 Bb.A.419
18. SEQ ID NO:18 Bb.A.420
19. SEQ ID NO:19 Bb.A.421
20. SEQ ID NO:20 Bb.A.422
21. SEQ ID NO:21 Bb.A.423
22. SEQ ID NO:22 Bb.A.424
23. SEQ ID NO:23 Bb.A.425
24. SEQ ID NO:24 13.C
25. SEQ ID NO:25 13.C.431
26. SEQ ID NO:26 13.C.432
27. SEQ ID NO:27 13.C.433
28. SEQ ID NO:28 13.C.434
29. SEQ ID NO:29 13.C.435
30. SEQ ID NO:30 13.C.436
31. SEQ ID NO:31 13.C.437
32. SEQ ID NO:32 13.C.438
33. SEQ ID NO:33 13.C.439
34. SEQ ED NO:34 13.C.440
35. SEQ ID NO:35 13.C.441
36. SEQ ID NO:36 13.C.442
37. SEQ ID NO:37 13.C.443
38. SEQ ID NO:38 13.C.444
39. SEQ ED NO:39 13.C.445
40. SEQ ID NO:40 13.C.446
41. SEQ ID NO:41 7EVEA
42. SEQ ID NO:42 7EVEA.451
43. SEQ ID NO:43 7EVEA.452
44. SEQ ID NO:44 7EVEA.453
45. SEQ ID NO:45 7EVEA.454
46. SEQ ED NO:46 7EVEA.455
47. SEQ ID NO:47 7EVEA.456
48. SEQ ED NO:48 7EVEA.457
49. SEQ ED NO:49 7EVEA.458
50. SEQ ID NO:50 7EVEA.459
51. SEQ ID NO:51 7EVEA.460
52. SEQ ID NO:52 7EVEA.461
53. SEQ ID NO:53 7EVEA.462
54. SEQ ID NO:54 7EVEA.463
55. SEQ ID NO:55 7EVEA.464
56. SEQ ID NO:56 7EVEA.465
57. SEQ ID NO:57 LEAI
58. SEQ ID NO:58 LEAI.471
59. SEQ ID NO:59 LEAI.472
60. SEQ ED NO:60 LEAI.473
61. SEQ ED NO:61 LEAI.474
62. SEQ ID NO:62 LEAI.475
63. SEQ ID NO:63 LEAI.476
64. SEQ ID NO:64 LEAI.477
65. SEQ ID NO:65 LEAI.478
66. SEQ ID NO:66 LEAI.479
67. SEQ ID NO:67 LEAI.480
68. SEQ ID NO:68 LEAI.481
69. SEQ ID NO:69 LEAI.482
70. SEQ ID NO:70 (aa//472//SPVDI—//137A)
71. SEQ ID NO:71 Forward variant Bgl site
72. SEQ ID NO:72 Reverse Not I containing reverse primer 5'-
73. SEQ ID NO:73 Not I containing forward primer
74. SEQ ID NO:74 XbaI containing reverse primer
75. SEQ ID NO:75 serine to alanine change reverse primer 5'-
76. SEQ ID NO:76 serine to alanine forward primer 5'-'
77. SEQ ID NO:77 (aa//474//SPVDI—//137A)
78. SEQ ID NO:78 (aa//482//SPVDI—//137A)
79. SEQ ID NO:79 (na1//474//SPVDI—//137A)
80. SEQ ID NO:80 (na2//474//SPVDI—//137A)
81. SEQ ID NO:81 (aa//474+I7V//SPVDI—//137A)
82. SEQ ID NO:82 (na1//474+I7V//SPVDI—//137A)
83. SEQ ID NO:83 (na2//474+I7V//SPVDI—//137A)
84. SEQ ID NO:84 (aa//480//SPVDI—//137A)
85. SEQ ID NO:85 (aa//474//HGSPVDI—//S137)
86. SEQ ID NO:86 (aa//482//HGSPVDI—//5S37)
87. SEQ ID NO:87 (aa//480//HGSPVDI—//S137)
88. SEQ ID NO:88 seq for chicken ATIII which is 67% identical to human ATIII Genbank Accession No AAB35653
89. SEQ ID NO:89: seq for frog antithrombin which is 67% identical to human ATIII Genbank Accession No. AAL60467
90. SEQ ED NO:90 seq for mouse ATIII which is 90% identical with human ATIII Genbank Accession No. BAB16827
91. SEQ ID NO:91: Human cDNA ATIII sequence Genbank Accession No. 103102
92. SEQ ID NO:92 ATIII with Generic sequence.
93. SEQ ID NO:93 ATIII, native loop sequence

What is claimed is:

1. A variant antithrombin III, comprising a substitution at position P3, wherein the substitution at P3 is an E, H, K, L, P, Q, R, W, or Y.

2. The variant ATIII of claim 1, wherein the variant ATIII has a combined activity greater than or equal to plasma ATIII in a coupled assay.

3. The variant ATIII of claim 2, wherein the ATIII retains base thrombin inhibition activity of at least 5%.

4. The variant ATIII of claim 2, wherein the variant ATIII produce a predicted half life of thrombin at 60 minutes after a bolus administration to a subject that is greater than or equal to 0.9 the half life following a plasma ATIII administration.

5. The variant antithrombin III of claim 2, wherein the variant antithrombin III has an increased protease resistance greater than or equal to the protease resistance of plasma ATIII.

6. The variant antithrombin III of claim 2, wherein the variant antithrombin III has an increased human neutrophil elastase resistance greater than or equal to the protease resistance of plasma ATIII.

7. The variant antithrombin III of claim 2, wherein the variant antithrombin III has an increased cathepsin G resistance greater than or equal to the protease resistance of plasma ATIII.

8. The variant ATIII of claim 1, wherein the variant ATIII retains increased protease resistance and retains observable anti-thrombin activity.

9. The variant ATIII of claim 1, wherein the variant ATIII retains increased protease resistance and retains observable anti factor fXa activity.

10. A method of inhibiting septic disseminated intravascular coagulation in a subject comprising administrating an ATIII variant of claim 1 to a subject having septic disseminated intravascular coagulation, wherein the ATIII variants inhibit thrombin, thereby inhibiting septic disseminated intravascular coagulation in the subject.

11. A method of reducing sepsis in a subject, comprising administering an ATIII variant of claim 1 to a subject having sepsis, thereby reducing sepsis in the subject.

12. A method of inhibiting sepsis induced shock in a subject comprising administering an ATIII variant of claim 1 to a subject, thereby reducing sepsis induced shock in the subject.

13. A method of making the variant ATIII of claim 1, comprising linking in an operative way a nucleic acid molecule encoding a protein set forth in SEQ ID NO:77 wherein the nucleic acid sequence comprises a sequence that hybridizes under stringent hybridization conditions to a sequence set forth SEQ ID NO:79, or a degenerate variant thereof, and a sequence controlling the expression of the nucleic acid.

14. A cell comprising the variant ATIII of claim 1.

15. A cell produced by the process of transforming the cell with any of the disclosed nucleic acids of claim 13.

16. A cell produced by the process of administering the variant ATIII of claim 1.

* * * * *

SEQUENCE LISTING

```
<160> NUMBER OF SEQ ID NOS: 93

<210> SEQ ID NO 1
<211> LENGTH: 54
<212> TYPE: DNA
```

```
<213> ORGANISM: Artificial Sequence
<220> FEATURE:
<223> OTHER INFORMATION: Description of Artificial Sequence:/note =
      synthetic construct

<400> SEQUENCE: 1
catgcggccg caagtaccga aggtttcttc tctggccgtt cgctaaaccc caac            54

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 2
catgcggccg caagtaccga aggtttcttc gacggccgtt cgctaaaccc caac            54

<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 3
catgcggccg caagtaccga aggtttcttc gagggccgtt cgctaaaccc caac            54

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 4
catgcggccg caagtaccga aggtttcttc aacggccgtt cgctaaaccc caac            54

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 5
catgcggccg caagtaccga aggtttcttc cagggccgtt cgctaaaccc caac            54

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 6
catgcggccg caagtaccga aggtttcttc ggtggccgtt cgctaaaccc caac            54

<210> SEQ ID NO 7
<211> LENGTH: 54
<212> TYPE: DNA
<213> ORGANISM: Artificial Sequence
```

-continued

```
<220> FEATURE:
<223> OTHER INFORMATION: Description of Artificial Sequence:/note =
      synthetic construct

<400> SEQUENCE: 7
catgcggccg caagtaccga aggtttcttc tggggccgtt cgctaaaccc caac        54

<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 8
catgcggccg caagtaccga gggtgaggct tctggccgtt cgctaaaccc caac        54

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 9
catgcggccg caagtaccga gggtgagatt tctggccgtt cgctaaaccc caac        54

<210> SEQ ID NO 10
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 10
catgcggccg caagtaccga gggtgagctc tctggccgtt cgctaaaccc caac        54

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 11
catgcggccg caagtaccga gggtgagttc tctggccgtt cgctaaaccc caac        54

<210> SEQ ID NO 12
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 12
catgcggccg caagtaccga gggtgagtgg tctggccgtt cgctaaaccc caac        54

<210> SEQ ID NO 13
<211> LENGTH: 54
<212> TYPE: DNA
<213> ORGANISM: Artificial Sequence
<220> FEATURE:
```

```
<223> OTHER INFORMATION: Description of Artificial Sequence:/note =
      synthetic construct

<400> SEQUENCE: 13
catgcggccg caagtaccga gggtgaggtc tctggccgtt cgctaaaccc caac          54

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 14
catgcggccg caagtaccga gggtgagcag tctggccgtt cgctaaaccc caac          54

<210> SEQ ID NO 15
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 15
catgcggccg caagtaccga gggtgagaac tctggccgtt cgctaaaccc caac          54

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 16
catgcggccg caagtaccga gggtgaggct tctcctcgtt cgctaaaccc caac          54

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 17
catgcggccg caagtaccga gggtgagatt tctcctcgtt cgctaaaccc caac          54

<210> SEQ ID NO 18
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 18
catgcggccg caagtaccga gggtgagctc tctcctcgtt cgctaaaccc caac          54

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence:/note =
``` synthetic construct

<400> SEQUENCE: 19
catgcggccg caagtaccga gggtgagttc tctcctcgtt cgctaaaccc caac    54

<210> SEQ ID NO 20
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 20
catgcggccg caagtaccga gggtgagtgg tctcctcgtt cgctaaaccc caac    54

<210> SEQ ID NO 21
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 21
catgcggccg caagtaccga gggtgaggtc tctcctcgtt cgctaaaccc caac    54

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 22
catgcggccg caagtaccga gggtgagcag tctcctcgtt cgctaaaccc caac    54

<210> SEQ ID NO 23
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 23
catgcggccg caagtaccga gggtgagaac tctcctcgtt cgctaaaccc caac    54

<210> SEQ ID NO 24
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 24
catgcggccg caagtaccga gctcgagggt gctggccgtt cgctaaaccc caac    54

<210> SEQ ID NO 25
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

```
<400> SEQUENCE: 25
catgcggccg caagtaccga gctcgaggct gctggccgtt cgctaaaccc caac        54

<210> SEQ ID NO 26
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 26
catgcggccg caagtaccga gctcgagatt gctggccgtt cgctaaaccc caac        54

<210> SEQ ID NO 27
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 27
catgcggccg caagtaccga gctcgagctc gctggccgtt cgctaaaccc caac        54

<210> SEQ ID NO 28
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 28
catgcggccg caagtaccga gctcgagttc gctggccgtt cgctaaaccc caac        54

<210> SEQ ID NO 29
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 29
catgcggccg caagtaccga gctcgagtgg gctggccgtt cgctaaaccc caac        54

<210> SEQ ID NO 30
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 30
catgcggccg caagtaccga gctcgaggtc gctggccgtt cgctaaaccc caac        54

<210> SEQ ID NO 31
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct
```

<400> SEQUENCE: 31
catgcggccg caagtaccga gctcgagcag gctggccgtt cgctaaaccc caac  54

<210> SEQ ID NO 32
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 32
catgcggccg caagtaccga gctcgagaac gctggccgtt cgctaaaccc caac  54

<210> SEQ ID NO 33
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 33
catgcggccg caagtaccga gctcgaggct gctcctcgtt cgctaaaccc caac  54

<210> SEQ ID NO 34
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 34
catgcggccg caagtaccga gctcgagatt gctcctcgtt cgctaaaccc caac  54

<210> SEQ ID NO 35
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 35
catgcggccg caagtaccga gctcgagctc gctcctcgtt cgctaaaccc caac  54

<210> SEQ ID NO 36
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 36
catgcggccg caagtaccga gctcgagttc gctcctcgtt cgctaaaccc caac  54

<210> SEQ ID NO 37
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 37
catgcggccg caagtaccga gctcgagtgg gctcctcgtt cgctaaaccc caac        54

<210> SEQ ID NO 38
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 38
catgcggccg caagtaccga gctcgaggtc gctcctcgtt cgctaaaccc caac        54

<210> SEQ ID NO 39
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 39
catgcggccg caagtaccga gctcgagcag gctcctcgtt cgctaaaccc caac        54

<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 40
catgcggccg caagtaccga gctcgagaac gctcctcgtt cgctaaaccc caac        54

<210> SEQ ID NO 41
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 41
catgcggccg caagtaccga ggtcgaggct gctggccgtt cgctaaaccc caac        54

<210> SEQ ID NO 42
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 42
catgcggccg caagtaccga ggtcgagatt gctggccgtt cgctaaaccc caac        54

<210> SEQ ID NO 43
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 43

-continued catgcggccg caagtaccga ggtcgagctc gctggccgtt cgctaaaccc caac    54

<210> SEQ ID NO 44
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 44
catgcggccg caagtaccga ggtcgagttc gctggccgtt cgctaaaccc caac    54

<210> SEQ ID NO 45
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 45
catgcggccg caagtaccga ggtcgagtgg gctggccgtt cgctaaaccc caac    54

<210> SEQ ID NO 46
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 46
catgcggccg caagtaccga ggtcgaggtc gctggccgtt cgctaaaccc caac    54

<210> SEQ ID NO 47
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 47
catgcggccg caagtaccga ggtcgagcag gctggccgtt cgctaaaccc caac    54

<210> SEQ ID NO 48
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 48
catgcggccg caagtaccga ggtcgagaac gctggccgtt cgctaaaccc caac    54

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 49
catgcggccg caagtaccga ggttgaggct gctccacgtt cgctaaaccc caac    54

```
<210> SEQ ID NO 50
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 50
catgcggccg caagtaccga ggttgagatt gctccacgtt cgctaaaccc caac        54

<210> SEQ ID NO 51
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 51
catgcggccg caagtaccga ggttgagctc gctccacgtt cgctaaaccc caac        54

<210> SEQ ID NO 52
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 52
catgcggccg caagtaccga ggttgagttc gctccacgtt cgctaaaccc caac        54

<210> SEQ ID NO 53
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 53
catgcggccg caagtaccga ggttgagtgg gctccacgtt cgctaaaccc caac        54

<210> SEQ ID NO 54
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 54
catgcggccg caagtaccga ggttgaggtc gctccacgtt cgctaaaccc caac        54

<210> SEQ ID NO 55
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 55
catgcggccg caagtaccga ggttgagcag gctccacgtt cgctaaaccc caac        54
```

```
<210> SEQ ID NO 56
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 56
catgcggccg caagtaccga ggttgagaac gctccacgtt cgctaaaccc caac         54

<210> SEQ ID NO 57
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 57
catgcggccg caagtaccgc tctagaggct attggccgtt cgctaaaccc caac         54

<210> SEQ ID NO 58
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 58
catgcggccg caagtaccgc tctagaggct cgtggccgtt cgctaaaccc caac         54

<210> SEQ ID NO 59
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 59
catgcggccg caagtaccgc tctagaggct aacggccgtt cgctaaaccc caac         54

<210> SEQ ID NO 60
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 60
catgcggccg caagtaccgc tctagaggct gacggccgtt cgctaaaccc caac         54

<210> SEQ ID NO 61
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 61
catgcggccg caagtaccgc tctagaggct cagggccgtt cgctaaaccc caac         54
```

<210> SEQ ID NO 62
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 62
catgcggccg caagtaccgc tctagaggct ctaggccgtt cgctaaaccc caac         54

<210> SEQ ID NO 63
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 63
catgcggccg caagtaccgc tctagaggct aagggccgtt cgctaaaccc caac         54

<210> SEQ ID NO 64
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 64
catgcggccg caagtaccgc tctagaggct cctggccgtt cgctaaaccc caac         54

<210> SEQ ID NO 65
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 65
catgcggccg caagtaccgc tctagaggct agtggccgtt cgctaaaccc caac         54

<210> SEQ ID NO 66
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 66
catgcggccg caagtaccgc tctagaggct tggggccgtt cgctaaaccc caac         54

<210> SEQ ID NO 67
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 67
catgcggccg caagtaccgc tctagaggct tatggccgtt cgctaaaccc caac         54

<210> SEQ ID NO 68

```
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 68
catgcggccg caagtaccgc tctagaggct ggtggccgtt cgctaaaccc caac         54

<210> SEQ ID NO 69
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 69
catgcggccg caagtaccgc tctagaggct catggccgtt cgctaaaccc caac         54

<210> SEQ ID NO 70
<211> LENGTH: 430
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 70
```

Ser Pro Val Asp Ile Cys Thr Ala Lys Pro Arg Asp Ile Pro Met Asn
 1               5                  10                  15

Pro Met Cys Ile Tyr Arg Ser Pro Glu Lys Lys Ala Thr Glu Asp Glu
                20                  25                  30

Gly Ser Glu Gln Lys Ile Pro Glu Ala Thr Asn Arg Arg Val Trp Glu
            35                  40                  45

Leu Ser Lys Ala Asn Ser Arg Phe Ala Thr Thr Phe Tyr Gln His Leu
        50                  55                  60

Ala Asp Ser Lys Asn Asp Asn Asp Asn Ile Phe Leu Ser Pro Leu Ser
65                  70                  75                  80

Ile Ser Thr Ala Phe Ala Met Thr Lys Leu Gly Ala Cys Asn Asp Thr
                85                  90                  95

Leu Gln Gln Leu Met Glu Val Phe Lys Phe Asp Thr Ile Ser Glu Lys
            100                 105                 110

Thr Ser Asp Gln Ile His Phe Phe Ala Lys Leu Asn Cys Arg Leu
        115                 120                 125

Tyr Arg Lys Ala Asn Lys Ala Ser Lys Leu Val Ser Ala Asn Arg Leu
    130                 135                 140

Phe Gly Asp Lys Ser Leu Thr Phe Asn Glu Thr Tyr Gln Asp Ile Ser
145                 150                 155                 160

Glu Leu Val Tyr Gly Ala Lys Leu Gln Pro Leu Asp Phe Lys Glu Asn
                165                 170                 175

Ala Glu Gln Ser Arg Ala Ala Ile Asn Lys Trp Val Ser Asn Lys Thr
            180                 185                 190

Glu Gly Arg Ile Thr Asp Val Ile Pro Ser Glu Ala Ile Asn Glu Leu
        195                 200                 205

Thr Val Leu Val Leu Val Asn Thr Ile Tyr Phe Lys Gly Leu Trp Lys
    210                 215                 220

Ser Lys Phe Ser Pro Glu Asn Thr Arg Lys Glu Leu Phe Tyr Lys Ala
225                 230                 235                 240

Asp Gly Glu Ser Cys Ser Ala Ser Met Met Tyr Gln Glu Gly Lys Phe
                245                 250                 255

Arg Tyr Arg Arg Val Ala Glu Gly Thr Gln Val Leu Glu Leu Pro Phe
            260                 265                 270

Lys Gly Asp Asp Ile Thr Met Val Leu Ile Leu Pro Lys Pro Glu Lys
        275                 280                 285

Ser Leu Ala Lys Val Glu Lys Glu Leu Thr Pro Glu Val Leu Gln Glu
    290                 295                 300

Trp Leu Asp Glu Leu Glu Glu Met Met Leu Val Val His Met Pro Arg
305                 310                 315                 320

Phe Arg Ile Glu Asp Gly Phe Ser Leu Lys Glu Gln Leu Gln Asp Met
                325                 330                 335

Gly Leu Val Asp Leu Phe Ser Pro Glu Lys Ser Lys Leu Pro Gly Ile
            340                 345                 350

Val Ala Glu Gly Arg Asp Asp Leu Tyr Val Ser Asp Ala Phe His Lys
        355                 360                 365

Ala Phe Leu Glu Val Asn Glu Glu Gly Ser Glu Ala Ala Ala Ser Thr
    370                 375                 380

Ala Leu Glu Ala Asn Gly Arg Ser Leu Asn Pro Asn Arg Val Thr Phe
385                 390                 395                 400

Lys Ala Asn Arg Pro Phe Leu Val Phe Ile Arg Glu Val Pro Leu Asn
                405                 410                 415

Thr Ile Ile Phe Met Gly Arg Val Ala Asn Pro Cys Val Lys
            420                 425                 430

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 71
cagagatctc acgggagcct gtggacatc                                    29

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 72
catgcggccg cttcactgcc ttcttc                                       26

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 73
gtacggccgc aagtaccgct gttgtg                                       26

<210> SEQ ID NO 74
<211> LENGTH: 33

```
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 74
ctgtctagat tacttaacac aagggttggc tac                                    33

<210> SEQ ID NO 75
<211> LENGTH: 39
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 75
gctgatacta acttggaggc tttgttggct tttcgatag                              39

<210> SEQ ID NO 76
<211> LENGTH: 39
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 76
ctatcgaaaa gccaacaaag cctccaagtt agtatcagc                              39

<210> SEQ ID NO 77
<211> LENGTH: 430
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 77
```

Ser Pro Val Asp Ile Cys Thr Ala Lys Pro Arg Asp Ile Pro Met Asn
 1               5                  10                  15

Pro Met Cys Ile Tyr Arg Ser Pro Glu Lys Lys Ala Thr Glu Asp Glu
             20                  25                  30

Gly Ser Glu Gln Lys Ile Pro Glu Ala Thr Asn Arg Arg Val Trp Glu
         35                  40                  45

Leu Ser Lys Ala Asn Ser Arg Phe Ala Thr Thr Phe Tyr Gln His Leu
     50                  55                  60

Ala Asp Ser Lys Asn Asp Asn Asp Asn Ile Phe Leu Ser Pro Leu Ser
65                  70                  75                  80

Ile Ser Thr Ala Phe Ala Met Thr Lys Leu Gly Ala Cys Asn Asp Thr
                 85                  90                  95

Leu Gln Gln Leu Met Glu Val Phe Lys Phe Asp Thr Ile Ser Glu Lys
            100                 105                 110

Thr Ser Asp Gln Ile His Phe Phe Ala Lys Leu Asn Cys Arg Leu
        115                 120                 125

Tyr Arg Lys Ala Asn Lys Ala Ser Lys Leu Val Ser Ala Asn Arg Leu
    130                 135                 140

Phe Gly Asp Lys Ser Leu Thr Phe Asn Glu Thr Tyr Gln Asp Ile Ser
145                 150                 155                 160

Glu Leu Val Tyr Gly Ala Lys Leu Gln Pro Leu Asp Phe Lys Glu Asn
                165                 170                 175

```
Ala Glu Gln Ser Arg Ala Ala Ile Asn Lys Trp Val Ser Asn Lys Thr
            180                 185                 190

Glu Gly Arg Ile Thr Asp Val Ile Pro Ser Glu Ala Ile Asn Glu Leu
        195                 200                 205

Thr Val Leu Val Leu Val Asn Thr Ile Tyr Phe Lys Gly Leu Trp Lys
    210                 215                 220

Ser Lys Phe Ser Pro Glu Asn Thr Arg Lys Glu Leu Phe Tyr Lys Ala
225                 230                 235                 240

Asp Gly Glu Ser Cys Ser Ala Ser Met Met Tyr Gln Glu Gly Lys Phe
                245                 250                 255

Arg Tyr Arg Arg Val Ala Glu Gly Thr Gln Val Leu Glu Leu Pro Phe
            260                 265                 270

Lys Gly Asp Asp Ile Thr Met Val Leu Ile Leu Pro Lys Pro Glu Lys
        275                 280                 285

Ser Leu Ala Lys Val Glu Lys Glu Leu Thr Pro Glu Val Leu Gln Glu
    290                 295                 300

Trp Leu Asp Glu Leu Glu Glu Met Met Leu Val Val His Met Pro Arg
305                 310                 315                 320

Phe Arg Ile Glu Asp Gly Phe Ser Leu Lys Glu Gln Leu Gln Asp Met
                325                 330                 335

Gly Leu Val Asp Leu Phe Ser Pro Glu Lys Ser Lys Leu Pro Gly Ile
            340                 345                 350

Val Ala Glu Gly Arg Asp Asp Leu Tyr Val Ser Asp Ala Phe His Lys
        355                 360                 365

Ala Phe Leu Glu Val Asn Glu Glu Gly Ser Glu Ala Ala Ala Ser Thr
    370                 375                 380

Ala Leu Glu Ala Gln Gly Arg Ser Leu Asn Pro Asn Arg Val Thr Phe
385                 390                 395                 400

Lys Ala Asn Arg Pro Phe Leu Val Phe Ile Arg Glu Val Pro Leu Asn
                405                 410                 415

Thr Ile Ile Phe Met Gly Arg Val Ala Asn Pro Cys Val Lys
            420                 425                 430

<210> SEQ ID NO 78
<211> LENGTH: 430
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 78

Ser Pro Val Asp Ile Cys Thr Ala Lys Pro Arg Asp Ile Pro Met Asn
1               5                   10                  15

Pro Met Cys Ile Tyr Arg Ser Pro Glu Lys Lys Ala Thr Glu Asp Glu
            20                  25                  30

Gly Ser Glu Gln Lys Ile Pro Glu Ala Thr Asn Arg Arg Val Trp Glu
        35                  40                  45

Leu Ser Lys Ala Asn Ser Arg Phe Ala Thr Thr Phe Tyr Gln His Leu
    50                  55                  60

Ala Asp Ser Lys Asn Asp Asn Asp Asn Ile Phe Leu Ser Pro Leu Ser
65                  70                  75                  80

Ile Ser Thr Ala Phe Ala Met Thr Lys Leu Gly Ala Cys Asn Asp Thr
                85                  90                  95

Leu Gln Gln Leu Met Glu Val Phe Lys Phe Asp Thr Ile Ser Glu Lys
```

```
                    100                 105                 110
Thr Ser Asp Gln Ile His Phe Phe Ala Lys Leu Asn Cys Arg Leu
        115                 120                 125
Tyr Arg Lys Ala Asn Lys Ala Ser Lys Leu Val Ser Ala Asn Arg Leu
130                 135                 140
Phe Gly Asp Lys Ser Leu Thr Phe Asn Glu Thr Tyr Gln Asp Ile Ser
145                 150                 155                 160
Glu Leu Val Tyr Gly Ala Lys Leu Gln Pro Leu Asp Phe Lys Glu Asn
                165                 170                 175
Ala Glu Gln Ser Arg Ala Ala Ile Asn Lys Trp Val Ser Asn Lys Thr
            180                 185                 190
Glu Gly Arg Ile Thr Asp Val Ile Pro Ser Glu Ala Ile Asn Glu Leu
        195                 200                 205
Thr Val Leu Val Leu Val Asn Thr Ile Tyr Phe Lys Gly Leu Trp Lys
    210                 215                 220
Ser Lys Phe Ser Pro Glu Asn Thr Arg Lys Glu Leu Phe Tyr Lys Ala
225                 230                 235                 240
Asp Gly Glu Ser Cys Ser Ala Ser Met Met Tyr Gln Glu Gly Lys Phe
                245                 250                 255
Arg Tyr Arg Arg Val Ala Glu Gly Thr Gln Val Leu Glu Leu Pro Phe
            260                 265                 270
Lys Gly Asp Asp Ile Thr Met Val Leu Ile Leu Pro Lys Pro Glu Lys
        275                 280                 285
Ser Leu Ala Lys Val Glu Lys Glu Leu Thr Pro Glu Val Leu Gln Glu
    290                 295                 300
Trp Leu Asp Glu Leu Glu Glu Met Met Leu Val Val His Met Pro Arg
305                 310                 315                 320
Phe Arg Ile Glu Asp Gly Phe Ser Leu Lys Glu Gln Leu Gln Asp Met
                325                 330                 335
Gly Leu Val Asp Leu Phe Ser Pro Glu Lys Ser Lys Leu Pro Gly Ile
            340                 345                 350
Val Ala Glu Gly Arg Asp Asp Leu Tyr Val Ser Asp Ala Phe His Lys
        355                 360                 365
Ala Phe Leu Glu Val Asn Glu Glu Gly Ser Glu Ala Ala Ala Ser Thr
    370                 375                 380
Ala Leu Glu Ala His Gly Arg Ser Leu Asn Pro Asn Arg Val Thr Phe
385                 390                 395                 400
Lys Ala Asn Arg Pro Phe Leu Val Phe Ile Arg Glu Val Pro Leu Asn
                405                 410                 415
Thr Ile Ile Phe Met Gly Arg Val Ala Asn Pro Cys Val Lys
            420                 425                 430

<210> SEQ ID NO 79
<211> LENGTH: 1293
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 79
agccctgtgg acatctgcac agccaagccg cgggacattc ccatgaatcc catgtgcatt      60
taccgctccc cggagaagaa ggcaactgag gatgagggct cagaacagaa gatcccggag     120
gccaccaacc ggcgtgtctg ggaactgtcc aaggccaatt cccgctttgc taccactttc     180
```

```
tatcagcacc tggcagattc caagaatgac aatgataaca ttttcctgtc accccctgagt    240 atctccacgg cttttgctat gaccaagctg ggtgcctgta atgacaccct ccagcaactg    300
atggaggtat ttaagtttga caccatatct gagaaaacat ctgatcagat ccacttcttc    360
tttgccaaac tgaactgccg actctatcga aaagccaaca aagcctccaa gttagtatca    420
gccaatcgcc ttttggaga caaatcccctt accttcaatg agacctacca ggacatcagt    480
gagttggtat atggagccaa gctccagccc ctggacttca ggaaaatgc agagcaatcc    540 agagcggcca tcaacaaatg ggtgtccaat aagaccgaag gccgaatcac cgatgtcatt    600
ccctcggaag ccatcaatga gctcactgtt ctggtgctgg ttaacaccat ttacttcaag    660
ggcctgtgga agtcaaagtt cagccctgag aacacaagga aggaactgtt ctacaaggct    720
gatggagagt cgtgttcagc atctatgatg taccaggaag gcaagttccg ttatcggcgc    780
gtggctgaag gcacccaggt gcttgagttg cccttcaaag gtgatgacat caccatggtc    840
ctcatcttgc ccaagcctga aagagcctg gccaaggtgg agaaggaact caccccagag    900
gtgctgcagg agtggctgga tgaattggag agatgatgc tggtggtcca catgccccgc    960
ttccgcattg aggacggctt cagtttgaag gagcagctgc aagacatggg ccttgtcgat   1020
ctgttcagcc ctgaaaagtc caaactccca ggtattgttg cagaaggccg agatgacctc   1080
tatgtctcag atgcattcca taaggcattt cttgaggtaa atgaagaagg cagtgaagcg   1140
gccgcaagta ccgctctaga ggctcagggc cgttcgctaa accccaacag ggtgactttc   1200
aaggccaaca ggcctttcct ggttttttata agagaagttc ctctgaacac tattatcttc   1260
atgggcagag tagccaaccc ttgtgttaag taa                                 1293

<210> SEQ ID NO 80
<211> LENGTH: 1293
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 80
agtcccgtag atatatgcac agccaagccg cgggacattc ccatgaatcc catgtgcatt     60
taccgctccc cggagaagaa ggcaactgag gatgagggct cagaacagaa gatcccggag    120
gccaccaacc ggcgtgtctg ggaactgtcc aaggccaatt cccgctttgc taccactttc    180
tatcagcacc tggcagattc caagaatgac aatgataaca ttttcctgtc accccctgagt    240 atctccacgg cttttgctat gaccaagctg ggtgcctgta atgacaccct ccagcaactg    300
atggaggtat ttaagtttga caccatatct gagaaaacat ctgatcagat ccacttcttc    360
tttgccaaac tgaactgccg actctatcga aaagccaaca aagcctccaa gttagtatca    420
gccaatcgcc ttttggaga caaatcccctt accttcaatg agacctacca ggacatcagt    480
gagttggtat atggagccaa gctccagccc ctggacttca ggaaaatgc agagcaatcc    540 agagcggcca tcaacaaatg ggtgtccaat aagaccgaag gccgaatcac cgatgtcatt    600
ccctcggaag ccatcaatga gctcactgtt ctggtgctgg ttaacaccat ttacttcaag    660
ggcctgtgga agtcaaagtt cagccctgag aacacaagga aggaactgtt ctacaaggct    720
gatggagagt cgtgttcagc atctatgatg taccaggaag gcaagttccg ttatcggcgc    780
gtggctgaag gcacccaggt gcttgagttg cccttcaaag gtgatgacat caccatggtc    840
ctcatcttgc ccaagcctga aagagcctg gccaaggtgg agaaggaact caccccagag    900
```

```
gtgctgcagg agtggctgga tgaattggag gagatgatgc tggtggtcca catgccccgc      960
ttccgcattg aggacggctt cagtttgaag gagcagctgc aagacatggg ccttgtcgat     1020
ctgttcagcc ctgaaaagtc caaactccca ggtattgttg cagaaggccg agatgacctc     1080
tatgtctcag atgcattcca taaggcattt cttgaggtaa atgaagaagg cagtgaagcg     1140
gccgcaagta ccgctctaga ggctcagggc cgttcgctaa accccaacag ggtgactttc     1200
aaggccaaca ggcctttcct ggttttttata agagaagttc ctctgaacac tattatcttc     1260
atgggcagag tagccaaccc ttgtgttaag taa                                   1293
```

<210> SEQ ID NO 81
<211> LENGTH: 430
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 81

```
Ser Pro Val Asp Val Cys Thr Ala Lys Pro Arg Asp Ile Pro Met Asn
  1               5                  10                  15

Pro Met Cys Ile Tyr Arg Ser Pro Glu Lys Lys Ala Thr Glu Asp Glu
             20                  25                  30

Gly Ser Glu Gln Lys Ile Pro Glu Ala Thr Asn Arg Arg Val Trp Glu
         35                  40                  45

Leu Ser Lys Ala Asn Ser Arg Phe Ala Thr Thr Phe Tyr Gln His Leu
     50                  55                  60

Ala Asp Ser Lys Asn Asp Asn Asp Asn Ile Phe Leu Ser Pro Leu Ser
 65                  70                  75                  80

Ile Ser Thr Ala Phe Ala Met Thr Lys Leu Gly Ala Cys Asn Asp Thr
                 85                  90                  95

Leu Gln Gln Leu Met Glu Val Phe Lys Phe Asp Thr Ile Ser Glu Lys
            100                 105                 110

Thr Ser Asp Gln Ile His Phe Phe Phe Ala Lys Leu Asn Cys Arg Leu
        115                 120                 125

Tyr Arg Lys Ala Asn Lys Ala Ser Lys Leu Val Ser Ala Asn Arg Leu
    130                 135                 140

Phe Gly Asp Lys Ser Leu Thr Phe Asn Glu Thr Tyr Gln Asp Ile Ser
145                 150                 155                 160

Glu Leu Val Tyr Gly Ala Lys Leu Gln Pro Leu Asp Phe Lys Glu Asn
                165                 170                 175

Ala Glu Gln Ser Arg Ala Ala Ile Asn Lys Trp Val Ser Asn Lys Thr
            180                 185                 190

Glu Gly Arg Ile Thr Asp Val Ile Pro Ser Glu Ala Ile Asn Glu Leu
        195                 200                 205

Thr Val Leu Val Leu Val Asn Thr Ile Tyr Phe Lys Gly Leu Trp Lys
    210                 215                 220

Ser Lys Phe Ser Pro Glu Asn Thr Arg Lys Glu Leu Phe Tyr Lys Ala
225                 230                 235                 240

Asp Gly Glu Ser Cys Ser Ala Ser Met Met Tyr Gln Glu Gly Lys Phe
                245                 250                 255

Arg Tyr Arg Arg Val Ala Glu Gly Thr Gln Val Leu Glu Leu Pro Phe
            260                 265                 270

Lys Gly Asp Asp Ile Thr Met Val Leu Ile Leu Pro Lys Pro Glu Lys
        275                 280                 285
```

```
Ser Leu Ala Lys Val Glu Lys Glu Leu Thr Pro Glu Val Leu Gln Glu
    290                 295                 300

Trp Leu Asp Glu Leu Glu Glu Met Met Leu Val Val His Met Pro Arg
305                 310                 315                 320

Phe Arg Ile Glu Asp Gly Phe Ser Leu Lys Glu Gln Leu Gln Asp Met
                325                 330                 335

Gly Leu Val Asp Leu Phe Ser Pro Glu Lys Ser Lys Leu Pro Gly Ile
                340                 345                 350

Val Ala Glu Gly Arg Asp Asp Leu Tyr Val Ser Asp Ala Phe His Lys
                355                 360                 365

Ala Phe Leu Glu Val Asn Glu Gly Ser Glu Ala Ala Ala Ser Thr
    370                 375                 380

Ala Leu Glu Ala Gln Gly Arg Ser Leu Asn Pro Asn Arg Val Thr Phe
385                 390                 395                 400

Lys Ala Asn Arg Pro Phe Leu Val Phe Ile Arg Glu Val Pro Leu Asn
                405                 410                 415

Thr Ile Ile Phe Met Gly Arg Val Ala Asn Pro Cys Val Lys
                420                 425                 430

<210> SEQ ID NO 82
<211> LENGTH: 1293
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 82
agccctgtgg acgtatgcac agccaagccg cgggacattc ccatgaatcc catgtgcatt      60
taccgctccc cggagaagaa ggcaactgag gatgagggct cagaacagaa gatcccggag     120
gccaccaacc ggcgtgtctg gaactgtcc aaggccaatt cccgctttgc taccactttc      180
tatcagcacc tggcagattc caagaatgac aatgataaca tttttcctgtc acccctgagt    240 atctccacgg cttttgctat gaccaagctg ggtgcctgta atgacaccct ccagcaactg     300
atggaggtat ttaagtttga caccatatct gagaaaacat ctgatcagat ccacttcttc    360
tttgccaaac tgaactgccg actctatcga aaagccaaca aagcctccaa gttagtatca    420
gccaatcgcc ttttttggaga caaatccctt accttcaatg agacctacca ggacatcagt    480
gagttggtat atgagccaa gctccagccc ctggacttca ggaaaatgc agagcaatcc     540 agagcggcca tcaacaaatg ggtgtccaat aagaccgaag ccgaatcac cgatgtcatt    600 ccctcggaag ccatcaatga gctcactgtt ctggtgctgg ttaacaccat ttacttcaag    660
ggcctgtgga agtcaaagtt cagccctgag aacacaagga aggaactgtt ctacaaggct    720
gatggagagt cgtgttcagc atctatgatg taccaggaag gcaagttccg ttatcggcgc    780
gtggctgaag caccaggt gcttgagttg cccttcaaag tgatgacat caccatggtc       840 ctcatcttgc caagcctga aagagcctg gccaaggtgg agaaggaact caccccagag      900
gtgctgcagg agtggctgga tgaattggag gagatgatgc tggtggtcca catgccccgc    960
ttccgcattg aggacggctt cagtttgaag gagcagctgc aagacatggg ccttgtcgat   1020
ctgttcagcc tgaaaagtc caaactccca ggtattgttg cagaaggccg agatgacctc    1080
tatgtctcag atgcattcca taaggcattt cttgaggtaa atgaagaagg cagtgaagcg    1140
gccgcaagta ccgctctaga ggctcagggc cgttcgctaa cccccaacag ggtgactttc    1200
aaggccaaca ggccttttcct ggtttttata agagaagttc ctctgaacac tattatcttc    1260
```

```
atgggcagag tagccaaccc ttgtgttaag taa                                1293
```

<210> SEQ ID NO 83
<211> LENGTH: 1293
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 83

```
agtcccgtag atgtgtgcac agccaagccg cgggacattc ccatgaatcc catgtgcatt     60
taccgctccc cggagaagaa ggcaactgag gatgagggct cagaacagaa gatcccggag    120
gccaccaacc ggcgtgtctg ggaactgtcc aaggccaatt cccgctttgc taccactttc    180
tatcagcacc tggcagattc caagaatgac aatgataaca ttttcctgtc acccctgagt    240
atctccacgg cttttgctat gaccaagctg ggtgcctgta atgacaccct ccagcaactg    300
atggaggtat ttaagtttga caccatatct gagaaaacat ctgatcagat ccacttcttc    360
tttgccaaac tgaactgccg actctatcga aaagccaaca agcctccaa gttagtatca    420
gccaatcgcc ttttggaga caaatccctt accttcaatg agacctacca ggacatcagt    480
gagttggtat atgagccaa gctccagccc ctggacttca ggaaaatgc agagcaatcc    540
agagcggcca tcaacaaatg ggtgtccaat aagaccgaag ccgaatcac cgatgtcatt    600
ccctcggaag ccatcaatga gctcactgtt ctggtgctgg ttaacaccat ttacttcaag    660
ggcctgtgga agtcaaagtt cagccctgag aacacaagga aggaactgtt ctacaaggct    720
gatggagagt cgtgttcagc atctatgatg taccaggaag gcaagttccg ttatcggcgc    780
gtggctgaag gcacccaggt gcttgagttg cccttcaaag gtgatgacat caccatggtc    840
ctcatcttgc caagcctga aagagcctg gccaaggtgg agaaggaact caccccagag    900
gtgctgcagg agtggctgga tgaattggag gagatgatgc tggtggtcca catgccccgc    960
ttccgcattg aggacggctt cagtttgaag gagcagctgc aagacatggg ccttgtcgat   1020
ctgttcagcc ctgaaaagtc caaactccca ggtattgttg cagaaggccg agatgacctc   1080
tatgtctcag atgcattcca taggcattt cttgaggtaa atgaagaagg cagtgaagcg   1140
gccgcaagta ccgctctaga ggctcagggc cgttcgctaa accccaacag ggtgactttc   1200
aaggccaaca ggccttttcct ggtttttata agagaagttc ctctgaacac tattatcttc   1260
atgggcagag tagccaaccc ttgtgttaag taa                                1293
```

<210> SEQ ID NO 84
<211> LENGTH: 430
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 84

```
Ser Pro Val Asp Ile Cys Thr Ala Lys Pro Arg Asp Ile Pro Met Asn
 1               5                  10                  15

Pro Met Cys Ile Tyr Arg Ser Pro Glu Lys Lys Ala Thr Glu Asp Glu
                20                  25                  30

Gly Ser Glu Gln Lys Ile Pro Glu Ala Thr Asn Arg Arg Val Trp Glu
        35                  40                  45

Leu Ser Lys Ala Asn Ser Arg Phe Ala Thr Thr Phe Tyr Gln His Leu
```

```
            50                  55                  60
Ala Asp Ser Lys Asn Asp Asn Asp Asn Ile Phe Leu Ser Pro Leu Ser
 65                  70                  75                  80

Ile Ser Thr Ala Phe Ala Met Thr Lys Leu Gly Ala Cys Asn Asp Thr
                 85                  90                  95

Leu Gln Gln Leu Met Glu Val Phe Lys Phe Asp Thr Ile Ser Glu Lys
            100                 105                 110

Thr Ser Asp Gln Ile His Phe Phe Ala Lys Leu Asn Cys Arg Leu
            115                 120                 125

Tyr Arg Lys Ala Asn Lys Ala Ser Lys Leu Val Ser Ala Asn Arg Leu
        130                 135                 140

Phe Gly Asp Lys Ser Leu Thr Phe Asn Glu Thr Tyr Gln Asp Ile Ser
145                 150                 155                 160

Glu Leu Val Tyr Gly Ala Lys Leu Gln Pro Leu Asp Phe Lys Glu Asn
                165                 170                 175

Ala Glu Gln Ser Arg Ala Ala Ile Asn Lys Trp Val Ser Asn Lys Thr
            180                 185                 190

Glu Gly Arg Ile Thr Asp Val Ile Pro Ser Glu Ala Ile Asn Glu Leu
        195                 200                 205

Thr Val Leu Val Leu Val Asn Thr Ile Tyr Phe Lys Gly Leu Trp Lys
    210                 215                 220

Ser Lys Phe Ser Pro Glu Asn Thr Arg Lys Glu Leu Phe Tyr Lys Ala
225                 230                 235                 240

Asp Gly Glu Ser Cys Ser Ala Ser Met Met Tyr Gln Glu Gly Lys Phe
                245                 250                 255

Arg Tyr Arg Arg Val Ala Glu Gly Thr Gln Val Leu Glu Leu Pro Phe
            260                 265                 270

Lys Gly Asp Asp Ile Thr Met Val Leu Ile Leu Pro Lys Pro Glu Lys
        275                 280                 285

Ser Leu Ala Lys Val Glu Lys Glu Leu Thr Pro Glu Val Leu Gln Glu
    290                 295                 300

Trp Leu Asp Glu Leu Glu Glu Met Met Leu Val Val His Met Pro Arg
305                 310                 315                 320

Phe Arg Ile Glu Asp Gly Phe Ser Leu Lys Glu Gln Leu Gln Asp Met
                325                 330                 335

Gly Leu Val Asp Leu Phe Ser Pro Glu Lys Ser Lys Leu Pro Gly Ile
            340                 345                 350

Val Ala Glu Gly Arg Asp Asp Leu Tyr Val Ser Asp Ala Phe His Lys
        355                 360                 365

Ala Phe Leu Glu Val Asn Glu Glu Gly Ser Glu Ala Ala Ala Ser Thr
    370                 375                 380

Ala Leu Glu Ala Tyr Gly Arg Ser Leu Asn Pro Asn Arg Val Thr Phe
385                 390                 395                 400

Lys Ala Asn Arg Pro Phe Leu Val Phe Ile Arg Glu Val Pro Leu Asn
                405                 410                 415

Thr Ile Ile Phe Met Gly Arg Val Ala Asn Pro Cys Val Lys
            420                 425                 430

<210> SEQ ID NO 85
<211> LENGTH: 432
<212> TYPE: PRT
<213> ORGANISM: Artificial Sequence
<220> FEATURE:
<223> OTHER INFORMATION: Description of Artificial Sequence:/note =
      synthetic construct
```

```
<400> SEQUENCE: 85

His Gly Ser Pro Val Asp Ile Cys Thr Ala Lys Pro Arg Asp Ile Pro
  1               5                  10                  15

Met Asn Pro Met Cys Ile Tyr Arg Ser Pro Glu Lys Lys Ala Thr Glu
             20                  25                  30

Asp Glu Gly Ser Glu Gln Lys Ile Pro Glu Ala Thr Asn Arg Arg Val
         35                  40                  45

Trp Glu Leu Ser Lys Ala Asn Ser Arg Phe Ala Thr Thr Phe Tyr Gln
     50                  55                  60

His Leu Ala Asp Ser Lys Asn Asp Asn Asp Asn Ile Phe Leu Ser Pro
 65                  70                  75                  80

Leu Ser Ile Ser Thr Ala Phe Ala Met Thr Lys Leu Gly Ala Cys Asn
                 85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Ala Lys Leu Asn Cys
            115                 120                 125

Arg Leu Tyr Arg Lys Ala Asn Lys Ser Ser Lys Leu Val Ser Ala Asn
            130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
            195                 200                 205

Glu Leu Thr Val Leu Val Leu Val Asn Thr Ile Tyr Phe Lys Gly Leu
            210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
            275                 280                 285

Glu Lys Ser Leu Ala Lys Val Glu Lys Glu Leu Thr Pro Glu Val Leu
            290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
            355                 360                 365

His Lys Ala Phe Leu Glu Val Asn Glu Glu Gly Ser Glu Ala Ala Ala
            370                 375                 380

Ser Thr Ala Leu Glu Ala Gln Gly Arg Ser Leu Asn Pro Asn Arg Val
385                 390                 395                 400

Thr Phe Lys Ala Asn Arg Pro Phe Leu Val Phe Ile Arg Glu Val Pro
```

```
                   405                 410                 415

Leu Asn Thr Ile Ile Phe Met Gly Arg Val Ala Asn Pro Cys Val Lys
            420                 425                 430

<210> SEQ ID NO 86
<211> LENGTH: 432
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 86

His Gly Ser Pro Val Asp Ile Cys Thr Ala Lys Pro Arg Asp Ile Pro
  1               5                  10                  15

Met Asn Pro Met Cys Ile Tyr Arg Ser Pro Glu Lys Lys Ala Thr Glu
             20                  25                  30

Asp Glu Gly Ser Glu Gln Lys Ile Pro Glu Ala Thr Asn Arg Arg Val
         35                  40                  45

Trp Glu Leu Ser Lys Ala Asn Ser Arg Phe Ala Thr Thr Phe Tyr Gln
     50                  55                  60

His Leu Ala Asp Ser Lys Asn Asp Asn Asp Asn Ile Phe Leu Ser Pro
 65                  70                  75                  80

Leu Ser Ile Ser Thr Ala Phe Ala Met Thr Lys Leu Gly Ala Cys Asn
                 85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335
```

```
Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
            355                 360                 365

His Lys Ala Phe Leu Glu Val Asn Glu Glu Gly Ser Glu Ala Ala Ala
            370                 375                 380

Ser Thr Ala Leu Glu Ala His Gly Arg Ser Leu Asn Pro Asn Arg Val
385                 390                 395                 400

Thr Phe Lys Ala Asn Arg Pro Phe Leu Val Phe Ile Arg Glu Val Pro
                405                 410                 415

Leu Asn Thr Ile Ile Phe Met Gly Arg Val Ala Asn Pro Cys Val Lys
                420                 425                 430

<210> SEQ ID NO 87
<211> LENGTH: 432
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 87

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270
```

```
Pro Phe Lys Gly Asp Asp Ile Thr Met Val Leu Ile Leu Pro Lys Pro
            275                 280                 285
Glu Lys Ser Leu Ala Lys Val Glu Lys Glu Leu Thr Pro Glu Val Leu
        290                 295                 300
Gln Glu Trp Leu Asp Glu Leu Glu Glu Met Met Leu Val Val His Met
305                 310                 315                 320
Pro Arg Phe Arg Ile Glu Asp Gly Phe Ser Leu Lys Glu Gln Leu Gln
                325                 330                 335
Asp Met Gly Leu Val Asp Leu Phe Ser Pro Glu Lys Ser Lys Leu Pro
            340                 345                 350
Gly Ile Val Ala Glu Gly Arg Asp Asp Leu Tyr Val Ser Asp Ala Phe
        355                 360                 365
His Lys Ala Phe Leu Glu Val Asn Glu Glu Gly Ser Glu Ala Ala Ala
    370                 375                 380
Ser Thr Ala Leu Glu Ala Tyr Gly Arg Ser Leu Asn Pro Asn Arg Val
385                 390                 395                 400
Thr Phe Lys Ala Asn Arg Pro Phe Leu Val Phe Ile Arg Glu Val Pro
                405                 410                 415
Leu Asn Thr Ile Ile Phe Met Gly Arg Val Ala Asn Pro Cys Val Lys
            420                 425                 430

<210> SEQ ID NO 88
<211> LENGTH: 423
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 88

Arg Asp Ile Pro Val Asn Pro Ile Cys Ile Tyr Arg Asn Pro Glu Lys
1               5                   10                  15
Lys Pro Gln Glu Arg Arg Gly Ala Gly Ala Gly Glu Gly Gln Asp Pro
            20                  25                  30
Gly Val His Lys Pro Pro Val Trp Glu Leu Ser Arg Ala Asn Ser Arg
        35                  40                  45
Phe Ala Val Val Phe Tyr Lys His Leu Ala Asp Ser Lys Asp Asn Glu
    50                  55                  60
Glu Asn Ile Phe Leu Ser Pro Leu Ser Ile Ser Thr Ala Phe Ala Met
65                  70                  75                  80
Thr Lys Leu Gly Ala Cys Gly Asp Thr Leu Gln Gln Leu Met Glu Val
                85                  90                  95
Phe Gln Phe Asp Thr Ile Ser Glu Lys Thr Ser Asp Gln Val His Phe
            100                 105                 110
Phe Phe Ala Lys Leu Asn Cys Arg Leu Tyr Lys Lys Ala Asn Lys Ser
        115                 120                 125
Ser Glu Leu Ile Ser Ala Asn Arg Leu Phe Gly Glu Lys Ser Leu Val
    130                 135                 140
Phe Asn Glu Thr Tyr Gln Asn Ile Ser Glu Ile Val Tyr Gly Ala Lys
145                 150                 155                 160
Leu Trp Pro Leu Asn Phe Lys Glu Lys Pro Glu Leu Ser Arg Lys Ile
                165                 170                 175
Ile Asn Glu Trp Val Ala Asn Lys Thr Glu Arg Arg Ile Thr Glu Val
            180                 185                 190
Ile Pro Glu Lys Gly Ile Asp Asp Leu Thr Val Leu Val Leu Val Asn
```

-continued

```
                195                 200                 205
Thr Ile Tyr Phe Lys Gly His Trp Lys Ser Gln Phe Pro Ala Pro Asn
    210                 215                 220

Thr Arg Leu Asp Leu Phe His Lys Ala Asn Gly Glu Thr Cys Asn Val
225                 230                 235                 240

Pro Ile Met Tyr Gln Glu Ser Arg Phe Pro Tyr Ala Phe Ile Gln Glu
                245                 250                 255

Asp Lys Val Gln Val Leu Glu Leu Pro Tyr Lys Gly Asp Asp Ile Thr
                260                 265                 270

Met Val Leu Val Leu Pro Lys Ala Gly Thr Pro Leu Val Glu Val Glu
                275                 280                 285

Arg Asp Leu Thr Ser Asp Lys Leu Gln Asp Trp Ile Asp Ser Met Met
    290                 295                 300

Glu Val Ser Leu Thr Val Ser Phe Pro Arg Phe Arg Val Glu Asp Ser
305                 310                 315                 320

Phe Ser Val Lys Glu Lys Leu Arg Lys Met Gly Leu Glu Asp Leu Phe
                325                 330                 335

Ser Pro Glu Asn Ala Lys Leu Pro Gly Ile Val Ala Gly Asp Arg Thr
                340                 345                 350

Asp Leu Tyr Val Ser Glu Ala Phe His Lys Ala Phe Leu Glu Val Asn
                355                 360                 365

Glu Glu Gly Ser Glu Ala Ser Ala Ala Thr Ala Val Val Ile Ser Gly
    370                 375                 380

Arg Ser Phe Pro Met Asn Arg Ile Ile Phe Glu Ala Asn Arg Pro Phe
385                 390                 395                 400

Leu Leu Phe Ile Arg Glu Ala Thr Leu Asn Thr Ile Ile Phe Met Gly
                405                 410                 415

Arg Ile Ser Asp Pro Cys Ser
                420

<210> SEQ ID NO 89
<211> LENGTH: 456
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 89

Met Tyr Leu Leu Ser Leu Leu Leu Ser Leu Leu Gly Ser Ala Tyr
1               5                   10                  15

Leu Gln Pro Gln His Ala Asp Ile Cys Leu Ala Lys Pro Lys Asp Ile
                20                  25                  30

Pro Leu Thr Pro Met Cys Val Tyr Arg Lys Pro Leu Glu Val Val Glu
                35                  40                  45

Thr Glu Glu Lys Glu Lys Glu Pro Thr Thr Gln Glu Gln Lys Val Pro
                50                  55                  60

Glu Ser Thr Asn Pro Arg Val Tyr Glu Leu Ser Gln Ala Asn Ala Lys
65                  70                  75                  80

Phe Ala Ile Ala Phe Tyr Lys Asn Leu Ala Asp Ser Lys Arg Asp Lys
                85                  90                  95

Glu Asn Ile Phe Met Ser Pro Leu Ser Ile Ser Gln Ala Phe Thr Met
                100                 105                 110

Ala Lys Leu Gly Ala Cys Asn Asn Thr Leu Lys Gln Leu Met Glu Val
                115                 120                 125
```

Phe His Phe Asp Thr Val Ser Glu Arg Ala Ser Asp Gln Ile His Tyr
            130                 135                 140

Phe Phe Ala Lys Leu Asn Cys Arg Leu Phe Arg Lys Ala Asn Lys Ser
145                 150                 155                 160

Ser Glu Leu Val Ser Val Asn Arg Leu Phe Gly Glu Lys Ser Leu Thr
                165                 170                 175

Phe Asn Glu Thr Tyr Gln Asp Ile Ser Glu Ile Val Tyr Gly Ala Lys
            180                 185                 190

Leu Trp Pro Leu Asn Phe Arg Asp Lys Pro Glu Leu Ser Arg Glu Ile
        195                 200                 205

Ile Asn Asn Trp Val Ser Asn Lys Thr Glu Lys Arg Ile Thr Asp Val
    210                 215                 220

Ile Pro Lys Asp Ala Ile Thr Pro Asp Thr Val Leu Val Leu Ile Asn
225                 230                 235                 240

Ala Ile Tyr Phe Lys Gly Leu Trp Lys Ser Lys Phe Asn Ser Glu Asn
                245                 250                 255

Thr Lys Met Asp Gln Phe His Pro Ala Lys Asn Ser Asn Cys Leu Thr
            260                 265                 270

Ala Thr Met Tyr Gln Glu Gly Thr Phe Arg Tyr Gly Ser Phe Lys Asp
        275                 280                 285

Asp Gly Val Gln Val Leu Glu Leu Pro Tyr Lys Gly Asp Asp Ile Thr
    290                 295                 300

Met Val Leu Val Leu Pro Ser Gln Glu Thr Pro Leu Thr Thr Val Glu
305                 310                 315                 320

Gln Asn Leu Thr Leu Glu Lys Leu Gly Asn Trp Leu Gln Lys Ser Arg
                325                 330                 335

Glu Leu Gln Leu Ser Val Tyr Leu Pro Arg Phe Arg Val Glu Asp Ser
            340                 345                 350

Phe Ser Val Lys Glu Lys Leu Gln Glu Met Gly Leu Val Asp Leu Phe
        355                 360                 365

Asp Pro Asn Ser Ala Lys Leu Pro Gly Ile Ile Ala Gly Gly Arg Thr
    370                 375                 380

Asp Leu Tyr Val Ser Asp Ala Phe His Lys Ala Phe Leu Glu Val Asn
385                 390                 395                 400

Glu Glu Gly Ser Glu Ala Ala Ala Ser Thr Ala Val Ile Leu Thr Gly
                405                 410                 415

Arg Ser Leu Asn Leu Asn Arg Ile Ile Phe Arg Ala Asn Arg Pro Phe
            420                 425                 430

Leu Val Phe Ile Arg Glu Val Ala Ile Asn Ala Ile Leu Phe Met Gly
        435                 440                 445

Arg Val Ala Asn Pro Cys Thr Glu
    450                 455

<210> SEQ ID NO 90
<211> LENGTH: 465
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 90

Met Tyr Ser Pro Gly Ala Gly Ser Gly Ala Ala Gly Glu Arg Lys Leu
1               5                   10                  15

Cys Leu Leu Ser Leu Leu Leu Ile Gly Ala Leu Gly Cys Ala Ile Cys
            20                  25                  30

```
His Gly Asn Pro Val Asp Asp Ile Cys Ile Ala Lys Pro Arg Asp Ile
        35                  40                  45

Pro Val Asn Pro Leu Cys Ile Tyr Arg Ser Pro Gly Lys Lys Ala Thr
 50                  55                  60

Glu Glu Asp Gly Ser Glu Gln Lys Val Pro Glu Ala Thr Asn Arg Arg
 65                  70                  75                  80

Val Trp Glu Leu Ser Lys Ala Asn Ser Arg Phe Ala Thr Asn Phe Tyr
                85                  90                  95

Gln His Leu Ala Asp Ser Lys Asn Asp Asn Asp Ile Phe Leu Ser
                    100                 105                 110

Pro Leu Ser Ile Ser Thr Ala Phe Ala Met Thr Lys Leu Gly Ala Cys
                115                 120                 125

Asn Asp Thr Leu Lys Gln Leu Met Glu Val Phe Lys Phe Asp Thr Ile
 130                 135                 140

Ser Glu Lys Thr Ser Asp Gln Ile His Phe Phe Phe Ala Lys Leu Asn
145                 150                 155                 160

Cys Arg Leu Tyr Arg Lys Ala Asn Lys Ser Ser Asp Leu Val Ser Ala
                165                 170                 175

Asn Arg Leu Phe Gly Asp Lys Ser Leu Thr Phe Asn Glu Ser Tyr Gln
                180                 185                 190

Asp Val Ser Glu Val Val Tyr Gly Ala Lys Leu Gln Pro Leu Asp Phe
            195                 200                 205

Lys Glu Asn Pro Glu Gln Ser Arg Val Thr Ile Asn Asn Trp Val Ala
 210                 215                 220

Asn Lys Thr Glu Gly Arg Ile Lys Asp Val Ile Pro Gln Gly Ala Ile
225                 230                 235                 240

Asn Glu Leu Thr Ala Leu Val Leu Val Asn Thr Ile Tyr Phe Lys Gly
                245                 250                 255

Leu Trp Lys Ser Lys Phe Ser Pro Glu Asn Thr Arg Lys Glu Pro Phe
                260                 265                 270

Tyr Lys Val Asp Gly Gln Ser Cys Pro Val Pro Met Met Tyr Gln Glu
            275                 280                 285

Gly Lys Phe Lys Tyr Arg Arg Val Ala Glu Gly Thr Gln Val Leu Glu
 290                 295                 300

Leu Pro Phe Lys Gly Asp Asp Ile Thr Met Val Leu Ile Leu Pro Lys
305                 310                 315                 320

Pro Glu Lys Ser Leu Ala Lys Val Glu Gln Glu Leu Thr Pro Glu Leu
                325                 330                 335

Leu Gln Glu Trp Leu Asp Glu Leu Ser Glu Thr Met Leu Val Val His
                340                 345                 350

Met Pro Arg Phe Arg Thr Glu Asp Gly Phe Ser Leu Lys Glu Gln Leu
            355                 360                 365

Gln Asp Met Gly Leu Ile Asp Leu Phe Ser Pro Glu Lys Ser Gln Leu
            370                 375                 380

Pro Gly Ile Val Ala Gly Gly Arg Asp Asp Leu Tyr Val Ser Asp Ala
385                 390                 395                 400

Phe His Lys Ala Phe Leu Glu Val Asn Glu Glu Gly Ser Glu Ala Ala
                405                 410                 415

Ala Ser Thr Ser Val Val Ile Thr Gly Arg Ser Leu Asn Pro Asn Arg
            420                 425                 430

Val Thr Phe Lys Ala Asn Arg Pro Phe Leu Val Leu Ile Arg Glu Val
                435                 440                 445
```

```
Ala Leu Asn Thr Ile Ile Phe Met Gly Arg Val Ala Asn Pro Cys Val
    450                 455                 460

Asn
465

<210> SEQ ID NO 91
<211> LENGTH: 1599
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 91
caccagcatc atctcctcca attcatccag ctactctgcc catgaagata atagttttca      60
ggcggattgc ctcagatcac actatctcca cttgcccagc cctgtggaag attagcggcc    120
atgtattcca atgtgatagg aactgtaacc tctggaaaaa ggaaggttta tcttttgtcc    180
ttgctgctca ttggcttctg ggactgcgtg acctgtcacg ggagccctgt ggacatctgc    240
acagccaagc cgcgggacat tcccatgaat cccatgtgca tttaccgctc cccggagaag    300
aaggcaactg aggatgaggg ctcagaacag aagatcccgg aggccaccaa ccggcgtgtc    360
tgggaactgt ccaaggccaa ttcccgcttt gctaccactt tctatcagca cctggcagat    420
tccaagaatg acaatgataa cattttcctg tcaccactga gtatctccac ggcttttgct    480
atgaccaagc tgggtgcctg taatgacacc ctccagcaac tgatggaggt atttaagttt    540
gacaccatat ctgagaaaac atctgatcag atccacttct tctttgccaa actgaactgc    600
cgactctatc gaaaagccaa caaatcctcc aagttagtat cagccaatcg ccttttgga     660 gacaaatccc ttaccttcaa tgagacctac caggacatca gtgagttggt atatggagcc    720
aagctccagc ccctggactt caaggaaaat gcagagcaat ccagagcggc catcaacaaa    780
tgggtgtcca ataagaccga aggccgaatc accgatgtca ttccctcgga agccatcaat    840
gagctcactg ttctggtgct ggttaacacc atttacttca agggcctgtg aagtcaaag     900 ttcagccctg agaacacaag gaaggaactg ttctacaagg ctgatggaga gtcgtgttca    960
gcatctatga tgtaccagga aggcaagttc cgttatcggc gcgtggctga aggcacccag   1020
gtgcttgagt tgcccttcaa aggtgatgac atcaccatgg tcctcatctt gcccaagcct   1080
gagaagagcc tggccaaggt ggagaaggaa ctcacccag aggtgctgca ggagtggctg    1140
gatgaattgg aggagatgat gctggtggtt cacatgcccc gcttccgcat tgaggacggc   1200
ttcagtttga aggagcagct gcaagacatg ggccttgtcg atctgttcag ccctgaaaag   1260
tccaaactcc caggtattgt tgcagaaggc cgagatgacc tctatgtctc agatgcattc   1320
cataaggcat ttcttgaggt aaatgaagaa ggcagtgaag cagctgcaag taccgctgtt   1380
gtgattgctg ccgttcgct aaaccccaac agggtgactt tcaaggccaa caggcccttc    1440
ctggttttta taagagaagt tcctctgaac actattatct tcatgggcag agtagccaac   1500
ccttgtgtta agtaaaatgt tcttattctt tgcacctctt cctattttg gtttgtgaac     1560 agaagtaaaa ataaatacaa actacttcca tctcacatt                           1599

<210> SEQ ID NO 92
<211> LENGTH: 430
<212> TYPE: PRT
<213> ORGANISM: Artificial Sequence
<220> FEATURE:
<223> OTHER INFORMATION: Description of Artificial Sequence:/note =
      synthetic construct
```

-continued

```
<220> FEATURE:
<221> NAME/KEY: VARIANT
<222> LOCATION: (386)...(389)
<223> OTHER INFORMATION: Xaa = any amino acid

<400> SEQUENCE: 92
```

Ser Pro Val Asp Ile Cys Thr Ala Lys Pro Arg Asp Ile Pro Met Asn
1               5                   10                  15

Pro Met Cys Ile Tyr Arg Ser Pro Glu Lys Lys Ala Thr Glu Asp Glu
            20                  25                  30

Gly Ser Glu Gln Lys Ile Pro Glu Ala Thr Asn Arg Arg Val Trp Glu
        35                  40                  45

Leu Ser Lys Ala Asn Ser Arg Phe Ala Thr Thr Phe Tyr Gln His Leu
50                  55                  60

Ala Asp Ser Lys Asn Asp Asn Ile Phe Leu Ser Pro Leu Ser
65                  70                  75                  80

Ile Ser Thr Ala Phe Ala Met Thr Lys Leu Gly Ala Cys Asn Asp Thr
                85                  90                  95

Leu Gln Gln Leu Met Glu Val Phe Lys Phe Asp Thr Ile Ser Glu Lys
            100                 105                 110

Thr Ser Asp Gln Ile His Phe Phe Ala Lys Leu Asn Cys Arg Leu
        115                 120                 125

Tyr Arg Lys Ala Asn Lys Ala Ser Lys Leu Val Ser Ala Asn Arg Leu
130                 135                 140

Phe Gly Asp Lys Ser Leu Thr Phe Asn Glu Thr Tyr Gln Asp Ile Ser
145                 150                 155                 160

Glu Leu Val Tyr Gly Ala Lys Leu Gln Pro Leu Asp Phe Lys Glu Asn
                165                 170                 175

Ala Glu Gln Ser Arg Ala Ala Ile Asn Lys Trp Val Ser Asn Lys Thr
            180                 185                 190

Glu Gly Arg Ile Thr Asp Val Ile Pro Ser Glu Ala Ile Asn Glu Leu
        195                 200                 205

Thr Val Leu Val Leu Val Asn Thr Ile Tyr Phe Lys Gly Leu Trp Lys
210                 215                 220

Ser Lys Phe Ser Pro Glu Asn Thr Arg Lys Glu Leu Phe Tyr Lys Ala
225                 230                 235                 240

Asp Gly Glu Ser Cys Ser Ala Ser Met Met Tyr Gln Glu Gly Lys Phe
                245                 250                 255

Arg Tyr Arg Arg Val Ala Glu Gly Thr Gln Val Leu Glu Leu Pro Phe
            260                 265                 270

Lys Gly Asp Asp Ile Thr Met Val Leu Ile Leu Pro Lys Pro Glu Lys
        275                 280                 285

Ser Leu Ala Lys Val Glu Lys Glu Leu Thr Pro Glu Val Leu Gln Glu
290                 295                 300

Trp Leu Asp Glu Leu Glu Glu Met Met Leu Val Val His Met Pro Arg
305                 310                 315                 320

Phe Arg Ile Glu Asp Gly Phe Ser Leu Lys Glu Gln Leu Gln Asp Met
                325                 330                 335

Gly Leu Val Asp Leu Phe Ser Pro Glu Lys Ser Lys Leu Pro Gly Ile
            340                 345                 350

Val Ala Glu Gly Arg Asp Asp Leu Tyr Val Ser Asp Ala Phe His Lys
        355                 360                 365

Ala Phe Leu Glu Val Asn Glu Glu Gly Ser Glu Ala Ala Ala Ser Thr
370                 375                 380

```
Ala Xaa Xaa Xaa Xaa Gly Arg Ser Leu Asn Pro Asn Arg Val Thr Phe
385                 390                 395                 400

Lys Ala Asn Arg Pro Phe Leu Val Phe Ile Arg Glu Val Pro Leu Asn
                405                 410                 415

Thr Ile Ile Phe Met Gly Arg Val Ala Asn Pro Cys Val Lys
            420                 425                 430

<210> SEQ ID NO 93
<211> LENGTH: 430
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 93

Ser Pro Val Asp Ile Cys Thr Ala Lys Pro Arg Asp Ile Pro Met Asn
1               5                   10                  15

Pro Met Cys Ile Tyr Arg Ser Pro Glu Lys Lys Ala Thr Glu Asp Glu
            20                  25                  30

Gly Ser Glu Gln Lys Ile Pro Glu Ala Thr Asn Arg Arg Val Trp Glu
        35                  40                  45

Leu Ser Lys Ala Asn Ser Arg Phe Ala Thr Thr Phe Tyr Gln His Leu
50                  55                  60

Ala Asp Ser Lys Asn Asp Asn Asp Asn Ile Phe Leu Ser Pro Leu Ser
65                  70                  75                  80

Ile Ser Thr Ala Phe Ala Met Thr Lys Leu Gly Ala Cys Asn Asp Thr
                85                  90                  95

Leu Gln Gln Leu Met Glu Val Phe Lys Phe Asp Thr Ile Ser Glu Lys
            100                 105                 110

Thr Ser Asp Gln Ile His Phe Phe Phe Ala Lys Leu Asn Cys Arg Leu
        115                 120                 125

Tyr Arg Lys Ala Asn Lys Ala Ser Lys Leu Val Ser Ala Asn Arg Leu
130                 135                 140

Phe Gly Asp Lys Ser Leu Thr Phe Asn Glu Thr Tyr Gln Asp Ile Ser
145                 150                 155                 160

Glu Leu Val Tyr Gly Ala Lys Leu Gln Pro Leu Asp Phe Lys Glu Asn
                165                 170                 175

Ala Glu Gln Ser Arg Ala Ala Ile Asn Lys Trp Val Ser Asn Lys Thr
            180                 185                 190

Glu Gly Arg Ile Thr Asp Val Ile Pro Ser Glu Ala Ile Asn Glu Leu
        195                 200                 205

Thr Val Leu Val Leu Val Asn Thr Ile Tyr Phe Lys Gly Leu Trp Lys
210                 215                 220

Ser Lys Phe Ser Pro Glu Asn Thr Arg Lys Glu Leu Phe Tyr Lys Ala
225                 230                 235                 240

Asp Gly Glu Ser Cys Ser Ala Ser Met Met Tyr Gln Glu Gly Lys Phe
                245                 250                 255

Arg Tyr Arg Arg Val Ala Glu Gly Thr Gln Val Leu Glu Leu Pro Phe
            260                 265                 270

Lys Gly Asp Asp Ile Thr Met Val Leu Ile Leu Pro Lys Pro Glu Lys
        275                 280                 285

Ser Leu Ala Lys Val Glu Lys Glu Leu Thr Pro Glu Val Leu Gln Glu
290                 295                 300

Trp Leu Asp Glu Leu Glu Glu Met Met Leu Val Val His Met Pro Arg
305                 310                 315                 320
```

-continued

```
Phe Arg Ile Glu Asp Gly Phe Ser Leu Lys Glu Gln Leu Gln Asp Met
                325                 330                 335
Gly Leu Val Asp Leu Phe Ser Pro Glu Lys Ser Lys Leu Pro Gly Ile
            340                 345                 350
Val Ala Glu Gly Arg Asp Asp Leu Tyr Val Ser Asp Ala Phe His Lys
        355                 360                 365
Ala Phe Leu Glu Val Asn Glu Glu Gly Ser Glu Ala Ala Ala Ser Thr
    370                 375                 380
Ala Val Val Ile Ala Gly Arg Ser Leu Asn Pro Asn Arg Val Thr Phe
385                 390                 395                 400
Lys Ala Asn Arg Pro Phe Leu Val Phe Ile Arg Glu Val Pro Leu Asn
                405                 410                 415
Thr Ile Ile Phe Met Gly Arg Val Ala Asn Pro Cys Val Lys
            420                 425                 430
```